US011797158B2

(12) United States Patent
Ebler et al.

(10) Patent No.: US 11,797,158 B2
(45) Date of Patent: Oct. 24, 2023

(54) USER INTERFACE SYSTEM FOR A MEDICAL DEVICE

(71) Applicant: MAQUET Cardiopulmonary GmbH, Rastatt (DE)

(72) Inventors: Ralph J. Ebler, Warwick, NY (US); Daniel Medart, Stahnsdorf (DE); Aidan Hyde, Collingswood, NJ (US); Dwayne Kenneth Jones, Gloucester (CA); Wesley Scott Ashton, Bloomingdale, NJ (US)

(73) Assignee: MAQUET CARDIOPULMONARY GMBH, Rastatt (DE)

( * ) Notice: Subject to any disclaimer, the term of this patent is extended or adjusted under 35 U.S.C. 154(b) by 0 days.

(21) Appl. No.: 15/287,258

(22) Filed: Oct. 6, 2016

(65) Prior Publication Data

US 2017/0102846 A1    Apr. 13, 2017

Related U.S. Application Data

(60) Provisional application No. 62/238,358, filed on Oct. 7, 2015.

(51) Int. Cl.
*G06F 3/0483* (2013.01)
*A61M 1/14* (2006.01)
(Continued)

(52) U.S. Cl.
CPC ............ *G06F 3/0483* (2013.01); *A61M 1/14* (2013.01); *A61M 1/3626* (2013.01);
(Continued)

(58) Field of Classification Search
CPC ............... G06F 3/0483; G06F 3/04847; G06F 3/04886; A61M 1/3666; A61M 1/3626;
(Continued)

(56) References Cited

U.S. PATENT DOCUMENTS 4,092,641 A * 5/1978 Bellinghausen ..... G08B 29/046
                                                        200/61.03
4,712,191 A   12/1987 Penna
(Continued)

FOREIGN PATENT DOCUMENTS

CN    1946440 A    4/2007
CN    101341489 A  1/2009
(Continued)

OTHER PUBLICATIONS

Final Official Action issued in JP Application No. 2018-001824 (Year: 2018).*

(Continued)

*Primary Examiner* — Justin R. Blaufeld

(57) ABSTRACT

A customizable and intuitive user interface for medical systems and devices, such as cardiopulmonary bypass systems, perfusion systems, extracorporeal circulation apparatuses, and heart-lung machines, is provided, which allows for ease of access to critical patient data to facilitate blood perfusion and to monitor and regulate various physiological parameters of a patient and an extracorporeal blood flow circuit during surgical procedures, such as cardiopulmonary bypass and extracorporeal membrane oxygenation (ECMO).

19 Claims, 45 Drawing Sheets
(42 of 45 Drawing Sheet(s) Filed in Color)

(51) Int. Cl.
*G16H 40/67* (2018.01)
*G16H 20/40* (2018.01)
*A61M 1/36* (2006.01)
*G06F 3/04847* (2022.01)
*G06F 3/04886* (2022.01)

(52) U.S. Cl.
CPC ....... *A61M 1/3666* (2013.01); *G06F 3/04847* (2013.01); *G06F 3/04886* (2013.01); *G16H 20/40* (2018.01); *G16H 40/67* (2018.01); *A61M 2205/18* (2013.01); *A61M 2205/3331* (2013.01); *A61M 2205/3368* (2013.01); *A61M 2205/3379* (2013.01); *A61M 2205/505* (2013.01)

(58) Field of Classification Search
CPC ................ A61M 1/14; A61M 2205/18; A61M 2205/3331; A61M 2205/3368; A61M 2205/3379; A61M 2205/505; G16H 20/40; G16H 40/67
See application file for complete search history.

(56) References Cited

U.S. PATENT DOCUMENTS

| | | | |
|---|---|---|---|
| 5,216,579 A | 6/1993 | Basara et al. | |
| 5,931,160 A | 8/1999 | Gilmore et al. | |
| 6,037,538 A | 3/2000 | Brooks | |
| 6,322,502 B1* | 11/2001 | Schoenberg | G16H 80/00 |
| | | | 600/300 |
| 6,475,186 B1 | 11/2002 | Safar et al. | |
| D510,582 S | 10/2005 | Hoang et al. | |
| 6,979,423 B2 | 12/2005 | Moll | |
| D545,829 S | 7/2007 | Fletcher | |
| D565,627 S | 4/2008 | Kase | |
| D570,363 S | 6/2008 | Ulm et al. | |
| D575,792 S | 8/2008 | Benson | |
| 7,435,220 B2 | 10/2008 | Ranucci | |
| D586,818 S | 2/2009 | Luck | |
| D594,018 S | 6/2009 | Ball et al. | |
| D611,055 S | 3/2010 | Jonasson et al. | |
| D626,140 S | 10/2010 | McLaughlin et al. | |
| D629,005 S | 12/2010 | Jewitt et al. | |
| D632,698 S | 2/2011 | Judy et al. | |
| D632,699 S | 2/2011 | Judy et al. | |
| D633,919 S | 3/2011 | Chen | |
| 7,927,286 B2 | 4/2011 | Ranucci | |
| 7,931,601 B2 | 4/2011 | Ranucci | |
| D640,264 S | 6/2011 | Fujii et al. | |
| 8,105,265 B2 | 1/2012 | Demers et al. | |
| D653,672 S | 2/2012 | Friedlander | |
| D655,301 S | 3/2012 | Ray et al. | |
| D655,710 S | 3/2012 | Inada et al. | |
| 8,138,419 B2 | 3/2012 | Garza et al. | |
| D656,946 S | 4/2012 | Judy et al. | |
| D657,369 S | 4/2012 | Hecht et al. | |
| D658,196 S | 4/2012 | Wood et al. | |
| D660,864 S | 5/2012 | Anzures et al. | |
| D662,507 S | 6/2012 | Mori et al. | |
| D664,152 S | 7/2012 | Ray et al. | |
| D665,414 S | 8/2012 | Lee et al. | |
| D667,419 S | 9/2012 | Rai et al. | |
| D675,224 S | 1/2013 | Lee et al. | |
| 8,382,678 B2 | 2/2013 | Steffens et al. | |
| D678,895 S | 3/2013 | Ebler et al. | |
| 8,409,124 B2 | 4/2013 | Steffens et al. | |
| D682,288 S | 5/2013 | Donahue et al. | |
| D684,177 S | 6/2013 | Winther | |
| 8,521,556 B2 | 8/2013 | Chbat et al. | |
| 8,576,191 B2 | 11/2013 | Knott et al. | |
| D701,236 S | 3/2014 | Hatta | |
| 8,672,867 B2 | 3/2014 | Myklebust | |
| D702,247 S | 4/2014 | d'Amore et al. | |
| D703,681 S | 4/2014 | d'Amore et al. | |
| 8,690,784 B2 | 4/2014 | Ranucci | |
| D709,901 S | 7/2014 | Landis et al. | |
| D709,906 S | 7/2014 | Jonasson et al. | |
| D712,908 S | 9/2014 | Rodenhouse et al. | |
| D722,318 S | 2/2015 | Moore | |
| D722,319 S | 2/2015 | Moore | |
| D722,322 S | 2/2015 | Strayle | |
| D722,611 S | 2/2015 | Moore | |
| D728,586 S | 5/2015 | Konno et al. | |
| D728,601 S | 5/2015 | Angelides | |
| D729,267 S | 5/2015 | Yoo et al. | |
| D731,507 S | 6/2015 | Kyakuno | |
| D732,549 S | 6/2015 | Kim | |
| D733,172 S | 6/2015 | Angelides | |
| 9,047,787 B2* | 6/2015 | Pybus | G09B 23/285 |
| D735,743 S | 8/2015 | Kanenari et al. | |
| D737,304 S | 8/2015 | Urdan et al. | |
| D742,892 S | 11/2015 | Mitchell | |
| D746,310 S | 12/2015 | Ta | |
| D750,099 S | 2/2016 | Seo et al. | |
| D751,088 S | 3/2016 | Seo et al. | |
| 9,293,110 B2 | 3/2016 | Dolgos et al. | |
| D753,169 S | 4/2016 | Kim | |
| D754,143 S | 4/2016 | Sugimoto | |
| D754,161 S | 4/2016 | Wilder et al. | |
| D754,163 S | 4/2016 | Park | |
| D754,172 S | 4/2016 | Ferreira et al. | |
| D754,680 S | 4/2016 | Lee et al. | |
| D754,701 S | 4/2016 | Seo et al. | |
| D754,703 S | 4/2016 | Moon et al. | |
| D755,821 S | 5/2016 | Lee et al. | |
| D757,059 S | 5/2016 | Gray et al. | |
| D763,274 S | 8/2016 | Edwards et al. | |
| D764,488 S | 8/2016 | Bae et al. | |
| D768,166 S | 10/2016 | Kim | |
| D768,174 S | 10/2016 | Kim et al. | |
| D769,290 S | 10/2016 | Choi et al. | |
| D769,291 S | 10/2016 | Kim et al. | |
| D772,887 S | 11/2016 | Frew et al. | |
| D776,701 S | 1/2017 | Huang et al. | |
| D780,189 S | 2/2017 | Yang | |
| D781,308 S | 3/2017 | Austin et al. | |
| D783,039 S | 4/2017 | Park et al. | |
| D786,279 S | 5/2017 | McKim et al. | |
| D786,910 S | 5/2017 | Higuchi et al. | |
| D787,543 S | 5/2017 | Qiu et al. | |
| D788,134 S | 5/2017 | Wong | |
| 9,654,739 B1* | 5/2017 | Mitchell | A61B 8/56 |
| D791,810 S | 7/2017 | Hatzikostas | |
| D810,108 S | 2/2018 | Tuthill et al. | |
| D812,628 S | 3/2018 | Okado | |
| D819,042 S | 5/2018 | Ebler et al. | |
| D824,941 S | 8/2018 | Cooperman | |
| D829,234 S | 9/2018 | Yuguchi | |
| D829,736 S | 10/2018 | Jochetz et al. | |
| D842,869 S | 3/2019 | Ebler | |
| D843,387 S | 3/2019 | Yuguchi | |
| D847,846 S | 5/2019 | Peloquin | |
| D847,847 S | 5/2019 | Peloquin | |
| D852,828 S | 7/2019 | Guesnon, Jr. | |
| D872,753 S | 1/2020 | Ebler | |
| D886,142 S | 6/2020 | Lynne | |
| D920,999 S | 6/2021 | Sharp | |
| D958,172 S | 7/2022 | Lindberg | |
| 2002/0085952 A1* | 7/2002 | Ellingboe | A61M 1/3621 |
| | | | 604/4.01 |
| 2002/0177758 A1* | 11/2002 | Schoenberg | G16H 40/63 |
| | | | 600/300 |
| 2003/0135087 A1 | 7/2003 | Hickle et al. | |
| 2005/0149877 A1* | 7/2005 | Rice | G06F 3/0481 |
| | | | 382/280 |
| 2006/0009728 A1 | 1/2006 | Litzie et al. | |
| 2006/0053384 A1 | 3/2006 | La Fetra, Jr. | |
| 2006/0122551 A1 | 6/2006 | Brieske | |
| 2006/0229557 A1* | 10/2006 | Fathallah | G16H 40/63 |
| | | | 705/2 |
| 2006/0257283 A1 | 11/2006 | Ranucci | |
| 2007/0011702 A1 | 1/2007 | Vaysman | |
| 2007/0288868 A1 | 12/2007 | Rhee et al. | |

(56) References Cited

U.S. PATENT DOCUMENTS

| | | | |
|---|---|---|---|
| 2008/0017194 | A1 | 1/2008 | Hassanein et al. |
| 2008/0027368 | A1* | 1/2008 | Kollar ................. A61M 1/3621 604/6.14 |
| 2008/0028393 | A1* | 1/2008 | Yoshizawa ............ G09B 23/28 717/176 |
| 2008/0221495 | A1* | 9/2008 | Steffens ............... A61M 60/113 604/4.01 |
| 2008/0300572 | A1* | 12/2008 | Rankers ............. A61B 5/14532 604/504 |
| 2008/0307353 | A1* | 12/2008 | Molducci ............ A61M 1/1613 715/802 |
| 2009/0043173 | A1 | 2/2009 | Ranucci |
| 2009/0043219 | A1 | 2/2009 | Ranucci |
| 2009/0099498 | A1 | 4/2009 | Demers et al. |
| 2009/0177477 | A1* | 7/2009 | Nenov ................... G16H 10/60 704/E15.04 |
| 2011/0132371 | A1 | 6/2011 | Sanchez et al. |
| 2011/0154241 | A1* | 6/2011 | Skidmore ............ G06F 3/0484 715/771 |
| 2011/0208107 | A1 | 8/2011 | Müller-Spanka et al. |
| 2012/0029304 | A1 | 2/2012 | Medina et al. |
| 2012/0030611 | A1 | 2/2012 | Skidmore |
| 2012/0096381 | A1 | 4/2012 | Milne et al. |
| 2012/0137249 | A1 | 5/2012 | Milne et al. |
| 2012/0232428 | A1* | 9/2012 | Itzel ........................ G16H 40/63 600/588 |
| 2013/0041242 | A1* | 2/2013 | Karlsson ................ A61B 5/412 600/365 |
| 2013/0055167 | A1 | 2/2013 | Leong |
| 2013/0139090 | A1 | 5/2013 | Steffens et al. |
| 2013/0187780 | A1 | 7/2013 | Angelides |
| 2013/0190717 | A1* | 7/2013 | Dollar ................... A61M 5/172 604/505 |
| 2013/0283197 | A1* | 10/2013 | Skidmore ......... A61M 16/0051 715/771 |
| 2014/0039833 | A1 | 2/2014 | Sharpe, Jr. |
| 2014/0043271 | A1 | 2/2014 | Knott et al. |
| 2014/0050616 | A1 | 2/2014 | Ranucci |
| 2014/0073900 | A1 | 3/2014 | Wood et al. |
| 2014/0099617 | A1 | 4/2014 | Tallman, Jr. |
| 2014/0127063 | A1 | 5/2014 | Petersen et al. |
| 2014/0275819 | A1* | 9/2014 | Kassem ................ A61B 5/743 600/301 |
| 2014/0296676 | A1 | 10/2014 | Ranucci |
| 2014/0359452 | A1 | 12/2014 | Roach et al. |
| 2015/0067611 | A1 | 3/2015 | Spohr |
| 2015/0100009 | A1 | 4/2015 | Bearss |
| 2015/0105642 | A1 | 4/2015 | Rossi et al. |
| 2017/0100082 | A1* | 4/2017 | Mckeown ............... G16Z 99/00 |
| 2018/0344919 | A1 | 12/2018 | Jones et al. |
| 2019/0302981 | A1 | 10/2019 | Storr |

FOREIGN PATENT DOCUMENTS

| | | | | |
|---|---|---|---|---|
| EP | 2058017 | A2 * | 5/2009 | ............ A61M 1/101 |
| EP | 2058017 | A2 | 5/2009 | |
| EP | 2581846 | A1 | 4/2013 | |
| JP | 2006314800 | | 11/2006 | |
| JP | 1294399 | | 1/2007 | |
| JP | 1437253 | | 3/2012 | |
| JP | 2012101101 | | 5/2012 | |
| JP | 01458638 | | 1/2013 | |
| JP | 1484744 | | 10/2013 | |
| JP | 201446026 | A | 3/2014 | |
| NZ | 569268 | A | 12/2009 | |
| WO | 2015047927 | A1 | 4/2015 | |
| WO | 2016180953 | A1 | 11/2016 | |
| WO | 2017062549 | A1 | 4/2017 | |

OTHER PUBLICATIONS

Official Action issued in counterpart JP Application No. 2018-000284, dated Jul. 2, 2018.
Product Brochure—CS300 IABP—Product Features—2009 Publication—Maquet Cardiovascular LLC. U.S.A.
Product Brochure—CS100 IABP—Intelligent Counterpulsation—2010 Publication—Maquet Cardiovascular LLC. U.S.A.
Operators Guide—The CS100/CS100i Abbreviated Operator's Guide—2009 Publication—Maquet Cardiovascular LLC. U.S.A.
Operators Guide—Datascope Abbreviated Operator's Guide for the System 97 Intra-Aortic Balloon Pump—Published prior to 2009—Datascope Corp. U.S.A.
Brochure—Sensation and CS300 IABP System Smaller Meets Faster—Published in 2009—Maquet Cardiovascular LLC. U.S.A.
Brochure—CS300 IABP Product Features—Published in 2009—Maquet Cardiovascular LLC. U.S.A.
Sorin article, http://www.sorin.com/products/cardiac-surgery/perfusion/hlm/s5, printed on Jun. 13, 2015, 11 pages.
SORIN | S5 Brochure, Sorin Group USA, Inc., 2010.
MetaVision PerfusionTM, A point-of-care clinical information system for perfusionists, MAQUET Getinge Group 2015 <http://www.maquet.com/int/products/metavision-perfusion/>.
Heart-Lung Machine HL20 Brochure, MAQUET Cardiopulmonary AG 2012.
Heart Lung Machine Fundraising. Aug. 18, 2015. Web. Nov. 6, 2015. <http://www.heartcentreforchildren.com.au/heart-lung-machine-fundraising.html>.
Heart-lung machines, surgeryencyclopedia.com. Advameg, Inc. 2015. Web. Nov. 5, 2015. <http://www.surgeryencyclopedia.com/Fi-La/Heart-Lung-Machines.html>.
Machine coeur-poumon HL30. Feb. 21, 2013. Web. Nov. 18, 2015. <file:///C:/Users/u2002449/Downloads/mes-130225-MachineCoeurPoumonHL30-Maquet.pdf>.
Terumo Advanced Perfusion System 1. Terumo Cardiovascular Group. Nov. 2014. Web. Nov. 18, 2015. <http://www.terumo-cvs.com/doc/848594_Terumo-System1_Brochure%20_Nov2013_LowRes_Pgs.pdf>.
Product Catalog Jostra HL 20. MAQUET Cardiopulmonary AG. Web. Nov. 18, 2015. <http://glavm.ru/upload/information_system_18/2/8/7/item_287/information_itemsjproperty_343.pdf>.
SORIN | S5 System Operating Instructions, Sorin Group Deutschland GmbH, 2006, 2007.
Hessel, Eugene A., "Circuitry and Cannulation Techniques", Chapter 5, Cardiopulmonary Bypass: Principles and Practices, edited by Glenn P. Gravlee, 3rd edition, 2008, pp. 63-65.
Maquet Critical Care AB, User's Manual FLOW-i 3.0 Anesthesia System, 2012.
Maquet Critical Care AB, User's Manual SERVO-U Ventilator System v1.1, 2015.
International Search Report and Written Opinion issued in counterpart International Application No. PCT/US16/55645, dated Feb. 6, 2017.
International Preliminary Report on Patentability issued in counterpart International Application No. PCT/JS2016/055645, dated Apr. 19, 2018.
Official Action issued in JP Application No. 2017-012102, dated Apr. 17, 2018.
Official Action issued in JP Application No. 2018-000284, dated Jul. 2, 2018.
Image shown in the design publication of Design Registration No. 1458638 issued by Japanese Patent Office (the aricle to the design: Cash register).
Image shown in Electronic loading device on p. 1 of "Multi-function DC electronic load device PLZ-5W Series", which was received on Jul. 17, 2015 by National Center for Industrial Property Information and Training. (Patent Office Design Division Known Document No. HC27010355).
Office Action issued in U.S. Appl. No. 29/541,759, dated Aug. 1, 2016.
Office Action issued in U.S. Appl. No. 29/541,759, dated Nov. 17, 2016.
Office Action issued in U.S. Appl. No. 29/541,759, dated Mar. 31, 2017.
Office Action issued in U.S. Appl. No. 29/541,759, dated Sep. 7, 2017.

(56) References Cited

OTHER PUBLICATIONS

Office Action issued in U.S. Appl. No. 29/601,985, dated Jan. 26, 2018.
Karkouti et al., Hemodilution during cardiopulmonary bypass is an independent risk factor for acute renal failure in adult cardiac surgery, Abstract, J Thorac Cardiovasc Surg., Feb. 2005, 391-400, 129(2).
Ranucci, Marco, Invited Commentary, Ann Thorac Surg, 2011, 1118-1119, 91, available at http://ats.ctsnetjournals.org/cgi/content/full/91/4/1118.
Ranucci, Marco et al., Oxygen Delivery During Cardiopulmonary Bypass and Acute Renal Failure After Coronary Dperations, Ann Thorac Surg, 2005, 2213-2220, 80, available at http://ats.ctsnetjournals.org/cgi/content/full/80/6/2213.
Orpheus™ Perfusion Simulator, 2013, Terumo Cardiovascular Systems Corporation, Ann Arbor, MI, USA.
BMU 40—MAQUET, PDF Catalogue, Technical Documentation, downloaded from http://pdf.medicalexpo.com/pdf/maquet/bmu-40/69182-63791.html on Jan. 10, 2014.
Handy, Jonathan, The origin and interpretation of hyperlactataemia during low oxygen delivery states, Critical Dare, Jan. 12, 2007, 1-2, available at http://ccforum.com/content/11/1/104.
Lazzara, Elizabeth H., et al., Eight Critical Factors in Creating and Implementing a Successful Simulation Program, The Joint Commission Journal on Quality and Patient Safety, Jan. 2014, 21-29, vol. 40, No. 1.
Funkhouser, Robert K., et al., Change in Relationship of Blood vol. to Weight in Congestive Heart Failure, Circulation, Oct. 1957, 548-557, vol. XVI, American Heart Association, Dallas, TX, USA.
Kost, Gerald J., et al., Continuous Noninvasive Hemoglobin Monitoring: The Standard of Care and Future mpact, Crit Care Med., Oct. 1, 2012, 1-6, National Institutes of Health.
Ninomiya, Shinji, et al., Virtual Patient Simulator for the Perfusion Resource Management Drill, J. Extra Corpor Fechnol., Jul. 2009, 206-212, 41(4).
Ranucci, Marco et al., Anaerobic Metabolism During Cardiopulmonary Bypass: Predictive Value of Carbon Dioxide Derived Parameters, Ann Thorac Surg, 2006, 2189-95, 81, Elsevier Inc.
Trehan, Kanika et al., Simulation in cardiothoracic surgical training: Where do we stand?, The Journal of Thoracic and Cardiovascular Surgery, Jan. 2014, 18-24e2, vol. 147, No. 1.
International Search Report and Written Opinion issued in International Application No. PCT/EP2016/060786, dated Sep. 16, 2016.
International Preliminary Report on Patentability issued in International Application No. PCT/EP2016/060786, dated Nov. 23, 2017.
Office Action issued in EP Application No. 16722661.2, dated Jan. 3, 2018.
Search Report and Written Opinion of International Application No. PCT/US2016/056195, dated Dec. 30, 2016.
International Preliminary Report on Patentability of International Application No. PCT/US2016/056195, dated Apr. 19, 2018.
Sprinter Cart XL, Ready to Move When You Are, Maquet Getinge Group, Mar. 2013.
EP Office Action dated Feb. 5, 2020 for corresponding EP patent application No. 16854280.1, 10 pages.
Japanese Office Action dated Feb. 22, 2019 during the prosecution of Japanese Design Patent Application No. 2018-000284, 5 pages.
Japanese Decision on Appeal dated Mar. 6, 2019 during the prosecution of Japanese Design Patent Application No. 2017-012102, 59 pages.
EP Office Action dated May 8, 2019 during the prosecution of EP Patent Application No. 16722661.2, 6 pages.
Extended European Search Report dated May 9, 2019 during the prosecution of EP Patent Application No. 16854280.1, 11 pages.
Demers, Philippe, "Outcome With High Blood Lactate Levels During Cardiopulmonary Bypass in Adult Cardiac Dperation", The Annals of Thoracic Surgery, vol. 70, No. 6, pp. 2082-2086.
The American Heritage Desk Dictionary 940 (1981).
Examination Report issued in AU Application No. 2016336420 dated Sep. 1, 2020, 7 pages.

Official Action dated Aug. 28, 2020 in JP Application No. 2018-538055, 5 pages.
Official Action issued in Japanese Application No. 2017-558654 dated Mar. 27, 2020, 11 pages.
Office Action and Search Report issued in counterpart Chinese Application No. 201680071905.5 dated Apr. 28, 2020, 29 pages. (only English Translation of Office Action provided).
Notice of Allowance dated Aug. 12, 2020, issued in corresponding U.S. Appl. No. 29/645,640, 9 pages.
Notice of Allowance dated Feb. 20, 2020, issued in corresponding U.S. Appl. No. 29/645,640, 12 pages.
Office Action issued in JP Application No. 2019-182989 dated Dec. 22, 2020 (2 pages).
MetaVision Perfusion User Guide, iMDsoft, 2016, 93 pages.
Office Action issued in Chinese Application No. 201680027801.4 dated Oct. 10, 2020, 3 pages.
Notice of Allowance dated Feb. 12, 2021 in Japanese Patent Application No. 2017-558654, 3 pages.
Office Action and Search Report issued in Chinese Application No. 201680027801.4 dated Dec. 18, 2019, 22 pages.
Summons to attend oral proceedings issued in EP Application No. 16722661.2 on Feb. 6, 2020, 10 pages.
Rees, S. E., et al., Using Physiological Models and Decision Theory for Selecting Appropriate Ventilator Settings, Journal of Clinical Monitoring and Computing, 2006, 421-429, 20.
Extended European Search Report dated Mar. 12, 2021 in European Patent Application No. 20211741.2, 9 pages.
Richard W. Morris et al: "Original Articles: "Orpheus" Cardiopulmonary Bypass Simulation System", JECT 2007, No. 39, pp. 228-233.
Summons to Attend Oral Proceedings Pursuant to Rule 115(1) EPC for European Patent Application 16854280.1, European Patent Office, dated Jan. 12, 2021 (12 pages).
Second Office Action and Search Report issued in Chinese Patent Application No. 201680071905.5 dated Feb. 19, 2021, 6 pages.
Slenn P. Gravlee, Cardiopulmonary Bypass: Principles and Practices 3RD Edition 63-65 (Lippencott Williams & Wilkins 2008), Chapter 5, Eugene A. Hessel II, Circuitry and Cannulation Techniques, ISBN 378-0-7817-6815-3.
Ranucci MD, et al., Anaerobic Metabolism During Cardiopulmonary Bypass: Predictive Value of Carbon Dioxide Derived Parameters, The Annals of Thoracic Surgery, vol. 81, pp. 2189-2195, 2006.
Third Office Action dated Sep. 3, 2021 in Chinese Patent Application No. 201680071905.5, 15 pages.
Stockert S5 (an article of design: a cardiopulmonary device), S5 Perfusion System, Sorin Group Deutschland GMBH, 2010.
"We introduced "Stockert artificial cardiopulmonary device S5" in 2013" in an item "an artificial cardiopulmonary device", and it is recognized that this "Stockert artificial cardiopulmonary device S5" is same as the above "Stocked S5", downloaded from https://web.archive.org/web/20140321232731/www.nho-kumamoto.jp/about/hardwares.html on Nov. 20, 2018.
Official Action issued in JP Application No. 2017-12102, dated Oct. 30, 2018.
Image shown in the design publication of Design Registration No. 1458638 issued by Japanese Patent Office (the article to the design: Cash register).
An operation image of a multifunction machine on p. 3 of "image Runner Advance C7270/C7260", which was received on Oct. 3, 2014 by National Center for Industrial Property Infonnation and Training. (JP Patent Office Design Division Known Document No. HC26013857).
Image shown in Electronic loading device on p. 1 of "Multifunction DC electronic load device PLZ-5W Series", which was received on Jul. 17, 2015 by National Center for Industrial Property Information and Training. (JP Patent Office Design Division Known Document No. HC27010355).
Office Action issued in U.S. Appl. No. 29/646,368, dated Dec. 14, 2018.
Official Action—dated Dec. 6, 2017—for Japanese Patent Application No. 2017-12102, which corresponds to this pending application.

(56) References Cited

OTHER PUBLICATIONS

Image—Runner Advance C7270/C7260 (image cited in Officiai Action for Japanese Patent Application No. 2017-12102).
Image—1 Urbano L 02—http://www.kyocera.co.jp/prdct/telecom/consumer/102/function1/index.html (image and website cited in Official Action for Japanese Patent Application No. 2017-12102).
Final Office Action issued in Japanese Application No. 2019-182989 dated Nov. 8, 2021, 2 pages.
Office Action issued in Japanese Application No. 2020-154329 dated Dec. 1, 2021, 3 pages.
Non-Final Office Action dated Aug. 29, 2022, issued in U.S. Appl. No. 29/716,158, 8 pages.
Examination Report dated May 6, 2022 in corresponding Australian Application No. 2021206919, 4 pages.
Office Action dated Feb. 2, 2023 in corresponding Canadian Patent Application No. 3,001,213, 6 pages.
Office Action dated Dec. 19, 2022 in corresponding Japanese Patent Application No. 2022-035110, 2 pages (English language machine translation is provided).
Office Action dated Apr. 21, 2023 in corresponding Korean Patent Application No. 10-2018-7012878 (English language machine translation is provided), 4 pages.
Office Action dated Jan. 11, 2023 in European Patent Application No. 20211741.2, 8 pages.
Office Action dated Jan. 7, 2022 in Japanese Patent Application No. 2021-039960, 1 page (English language ranslation is provided).
Office Action dated Mar. 22, 2023 in Japanese Patent Application No. 2022-084415, 1 page (English language machine translation is provided).
Office Action dated Dec. 8, 2022 in U.S. Appl. No. 15/571,023, 15 pages.
Final Office Action dated Mar. 7, 2023 in U.S. Appl. No. 29/716,158, 8 pages.

\* cited by examiner

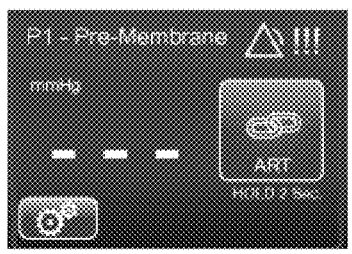
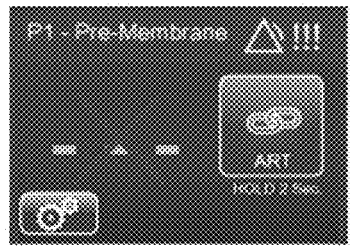
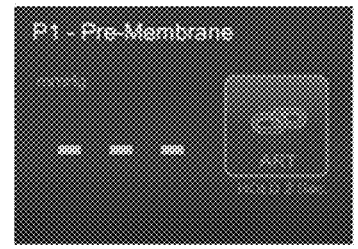
FIG. 10f    FIG. 10g    FIG. 10h
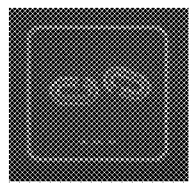
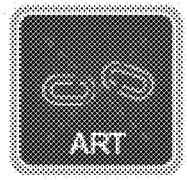
FIG. 11a    FIG. 11b
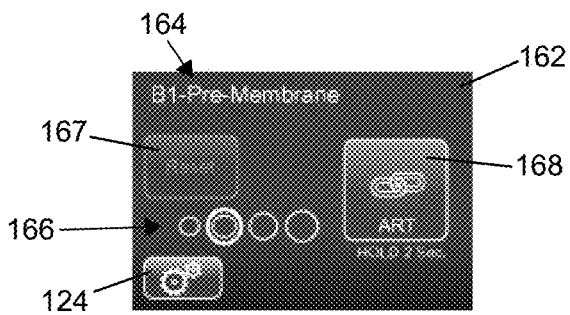
FIG. 12    FIG. 13a
FIG. 13b    FIG. 13c    FIG. 13d

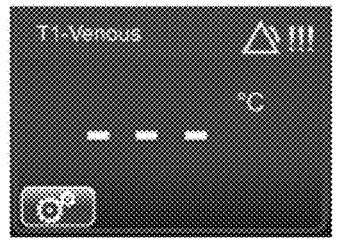
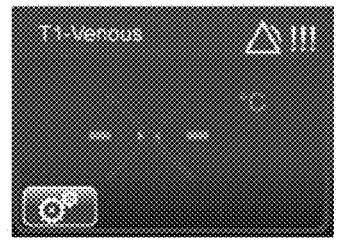
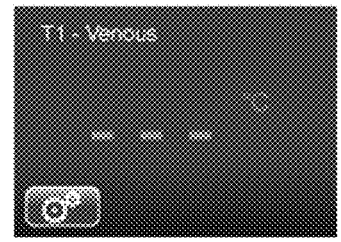
FIG. 19c             FIG. 19d             FIG. 19e
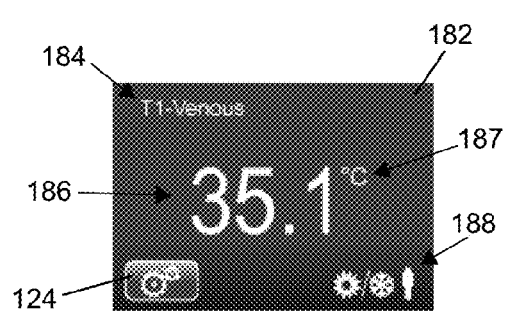
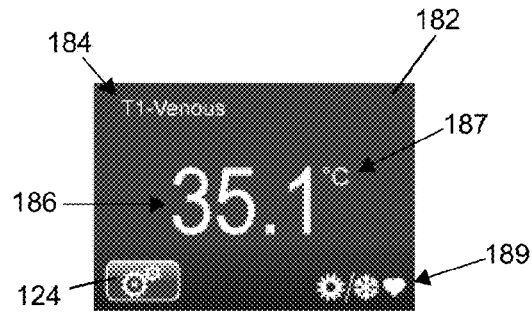
FIG. 19f             FIG. 19g
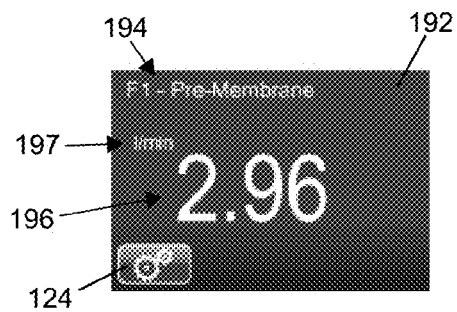
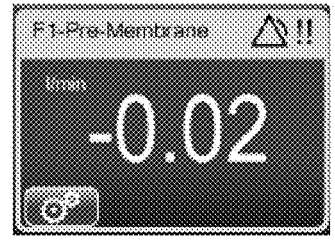
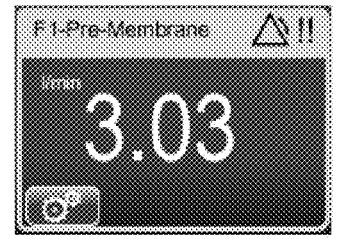
FIG. 20a             FIG. 20b             FIG. 20c

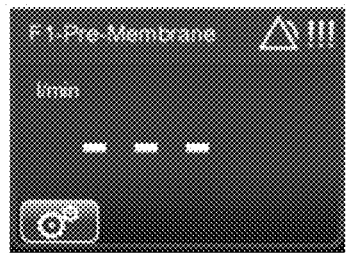 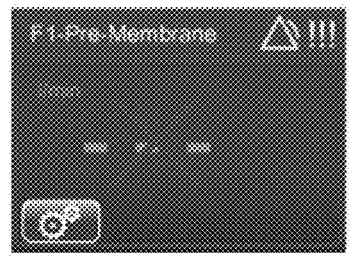 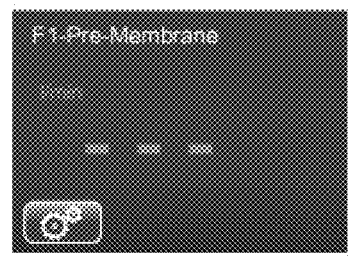
FIG. 20d FIG. 20e FIG. 20f
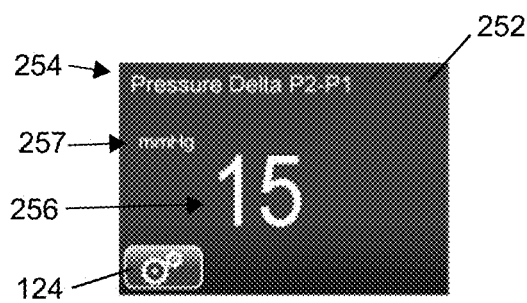 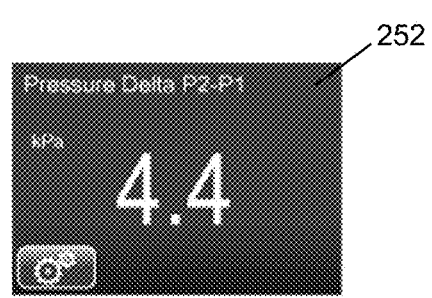
FIG. 21a FIG. 21b
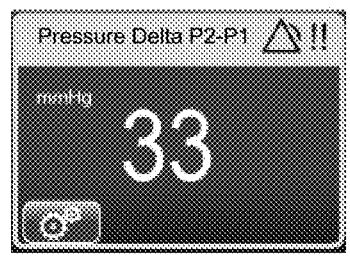 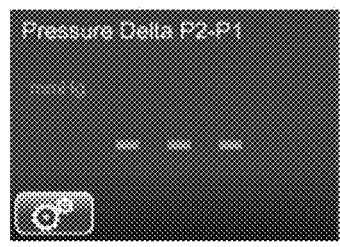
FIG. 21c FIG. 21d

| Scenario | No. 1 | No. 2 | No. 3 |
|---|---|---|---|
| IV Fluids (ml) | 0 | | |
| pRBCs (ml) | 0 | | |
| expCO2 (mmHg) | 32.1 | | |
| Flow (l/min) | 5.00 | | |
| SaO2 (%) | 99 | | |
| PaO2 (mmHg) | 250 | | |
| SvO2 (%) | 74 | | |
| PvO2 (mmHg) | 37 | | |
| Hb (g/dl) | | | |
| DO2I | | | |
| VO2I | | | |
| DO2I/VO2I | | | |
| DO2I/VCO2I | | | |

FIG. 30a

| Scenario | No. 1 | No. 2 | No. 3 |
|---|---|---|---|
| IV Fluids (ml) | 0 | 0 | |
| pRBCs (ml) | 0 | 0 | |
| expCO2 (mmHg) | 32.1 | 32.1 | |
| Flow (l/min) | 5.00 | 5.00 | |
| SaO2 (%) | 99 | 99 | |
| PaO2 (mmHg) | 250 | 250 | |
| SvO2 (%) | 74 | 74 | |
| PvO2 (mmHg) | 37 | 37 | |
| Hb (g/dl) | | | |
| DO2I | | | |
| VO2I | | | |
| DO2I/VO2I | | | |
| DO2I/VCO2I | | | |

FIG. 30b

| Scenario | No. 1 | No. 2 | No. 3 |
|---|---|---|---|
| IV Fluids (ml) | 0 | 0 | 0 |
| pRBCs (ml) | 250 | 500 | 750 |
| expCO2 (mmHg) | 33.7 | 33.7 | 33.7 |
| Flow (l/min) | 5.00 | 5.00 | 5.00 |
| SaO2 (%) | 99 | 99 | 99 |
| PaO2 (mmHg) | 250 | 250 | 250 |
| SvO2 (%) | 60 | 60 | 60 |
| PvO2 (mmHg) | 35 | 35 | 35 |
| Hb (g/dl) | 8.8 | 9.5 | 10.1 |
| DO2I | 311 | 417 | 442 |
| VO2I | 131 | 175 | 185 |
| DO2I/VO2I | 2.37 | 2.38 | 2.39 |
| DO2I/VCO2I | 3.74 | 5.02 | 5.32 |

FIG. 30c

| Scenario | No. 1 | No. 2 | No. 3 |
|---|---|---|---|
| IV Fluids (ml) | 250 | 250 | |
| pRBCs (ml) | 500 | 750 | |
| expCO2 (mmHg) | 32.1 | 32.1 | |
| Flow (l/min) | 5.00 | 5.00 | |
| SaO2 (%) | 99 | 99 | |
| PaO2 (mmHg) | 250 | 250 | |
| SvO2 (%) | 73 | 81 | |
| PvO2 (mmHg) | 36 | 40 | |
| Hb (g/dl) | 9.1 | 9.7 | |
| DO2I | 401 | 425 | |
| VO2I | 119 | 93 | |
| DO2I/VO2I | 3.36 | 4.58 | |
| DO2I/VCO2I | 5.06 | 5.37 | |

FIG. 30d

USER INTERFACE SYSTEM FOR A MEDICAL DEVICE

This application claims benefit of priority to U.S. Provisional Patent Application No. 62/238,358, filed Oct. 7, 2015, and the disclosure of this provisional application is herein incorporated by reference in its entirety.

FIELD OF THE DISCLOSURE

This disclosure pertains to a user interface for medical systems and devices, particularly for cardiopulmonary bypass systems, perfusion systems, extracorporeal circulation apparatuses and heart-lung machines, and the like. The application of such a user interface may be particularly useful for facilitating blood perfusion during medical and/or surgical procedures, as well as monitoring and regulating various physiological parameters of a patient necessary for sustaining life during medical and/or surgical procedures, such as cardiopulmonary bypass, extracorporeal membrane oxygenation (ECMO), and other extracorporeal circulation bypass procedures.

DESCRIPTION OF RELATED TECHNOLOGY (BACKGROUND OF THE DISCLOSURE)

Conventional heart-lung machines have static push button user interfaces that are hardwired into the machine and are not conveniently customizable, ergonomic, easy to use or allow for rapid access to patient data and/or menus for monitoring, regulating and/or adjusting patient parameters. These cumbersome interfaces are rigid in design and construction, and do not allow for flexibility for user customization of the interface for a particular clinical application, and/or for a particular patient and/or for a user's particular preferences. Furthermore, typical multi-level, nested menu layers employed by conventional heart-lung machine user interfaces may actually impede rapid access to critical patient data as well as obstruct access to such critical information due to the sequential opening-closing steps required of nested menus, which creates patient safety concerns.

Thus, conventional heart-lung machine user interfaces, such as those using nested menus, create, as a result of their design, obstacles to rapid user access to certain data fields, and disadvantageously prevent a user's rapid access, adjustment, and continuous monitoring of critical patient data without obstruction. These disadvantages may increase the likelihood of morbidity during complicated medical and/or surgical procedures involving extracorporeal circulation, such as is encountered with cardiopulmonary bypass procedures, in which a patient's physiological parameters must be closely monitored and regulated to sustain the patient's life during the procedure.

Moreover, conventional heart-lung machine user interfaces also have no, or only poorly integrated, alarm systems that are inadequate to timely notify, coordinate and advise a user of system errors during a cardiopulmonary bypass procedure.

In view of the deficiencies discussed above, there is a need to develop an intuitive, ergonomical, customizable and efficient user interface system and display for machines providing extracorporeal bypass circulation, such as a heart-lung machine and other cardiopulmonary bypass machines, so that rapid and continuous unobstructed access to patient critical data is facilitated during extracorporeal bypass procedures. There is also a need to develop a user interface system and display in this environment that facilitates the monitoring, regulation and adjustment of system parameters, and that further provides an integrated system wide alarm mechanism so that a user of the cardiopulmonary bypass machine is promptly notified, in a coordinated manner, of any system errors so that corrective measures may be taken immediately, thereby decreasing patient morbidity and improving patient outcomes.

SUMMARY OF THE DISCLOSURE

Thus, some embodiments of this disclosure pertain generally to a user interface, such as may be employed with a cardiopulmonary bypass system or other system involving an extracorporeal blood flow circuit. Such embodiments are constructed to be customizable by one or more users, flexible, and to possess a convenient modularity. Such embodiments may also be constructed to possess an intuitive design, be easy to use, and improve patient safety. In some such embodiments, the user interface is provided with intimately integrated alarms and other integrated safety measures so as to enhance safety during operation of the cardiopulmonary bypass system, or other systems involving an extracorporeal blood flow circuit. The following overview of non-limiting illustrative embodiments of this disclosure is provided to highlight various features of certain embodiments; however, this overview should not be construed as comprehensive or as limiting this disclosure in any substantial way. In other words, this summary highlights various advantageous features of apparatus and method embodiments of this disclosure; however, this summary should not be construed as a catalog of preferred embodiments.

In accordance with a first non-limiting illustrative embodiment of this disclosure, a cardiopulmonary bypass system is provided that includes: (a) a processor; and (b) a touchscreen comprising a graphical user interface operably connected to provide user input to the processor and to display measured data pertaining to one or more parameters outputted from the processor, wherein the graphical user interface is provided with a central portion divided into a plurality of sections, wherein at least one section displays an untabbed display page and at least one section displays a plurality of tabbed display pages, and wherein the untabbed display page comprises a plurality of sensor modules and at least one tabbed page comprises a plurality of sensor modules. In accordance with a second non-limiting illustrative embodiment of this disclosure, the first non-limiting embodiment is modified so that each sensor module of the untabbed display page is individually selected from the group consisting of a pressure sensor module, a bubble detection sensor module, a level sensor module, a flow sensor module, a pressure delta data sensor module, and a temperature sensor module. In accordance with a third non-limiting illustrative embodiment of this disclosure, the first and second non-limiting embodiments are modified so that the untabbed display page includes at least one pressure sensor module, at least one bubble detection sensor module, and at least one level sensor module.

In accordance with a fourth non-limiting illustrative embodiment of this disclosure, the first, second and third non-limiting embodiments are further modified so that each of the at least one pressure sensor module, the at least one bubble detection sensor module, and the at least one level sensor module is capable of displaying a plurality of alarm states selected from at least two of a high priority alarm state, a medium priority alarm state, and a low priority alarm state. In accordance with a fifth non-limiting illustrative embodiment of this disclosure, the first, second, third and fourth non-limiting embodiments are further modified so that the at least one pressure sensor module comprises a pressure value data field and a touch or pressure activated intervention button, wherein activation of the intervention button by touch or pressure causes operation of a pump of the cardiopulmonary bypass system to be temporarily modified.

In accordance with a sixth non-limiting illustrative embodiment of this disclosure, the first, second, third, fourth and fifth non-limiting embodiments are further modified so that the at least one bubble detection sensor module comprises a bubble detection data field and a touch or pressure activated reset button, wherein the bubble detection data field displays bubble detection data obtained from a bubble detection sensor. In accordance with a seventh non-limiting illustrative embodiment of this disclosure, the first, second, third, fourth, fifth, sixth and seventh non-limiting embodiments are further modified so that the at least one bubble detection sensor module displays a high priority alarm state when the bubble detection sensor detects bubbles exceeding a preset bubble detection size value, and the bubble detection sensor module continues to display the high priority alarm state until the reset button is activated by touch or pressure and the bubbles detected by the bubble detection sensor concurrently do not exceed the preset bubble detection size value. In accordance with an eighth non-limiting illustrative embodiment of this disclosure, the first, second, third, fourth, fifth, sixth and seventh non-limiting embodiments are further modified so that the at least one bubble detection sensor module further comprises a touch or pressure activated intervention button, wherein activation of the intervention by touch or pressure causes operation of a pump of the cardiopulmonary bypass system to be temporarily modified.

In accordance with a ninth non-limiting illustrative embodiment of this disclosure, the first, second, third, fourth, fifth, sixth, seventh and eighth non-limiting embodiments are further modified so that the at least one level sensor module comprises a level data field and a touch or pressure activated intervention button, wherein the intervention button is only enabled when a blood fluid level of a blood reservoir of the cardiopulmonary bypass system is at or below a predetermined low blood fluid level. In accordance with a tenth non-limiting illustrative embodiment of this disclosure, the first, second, third, fourth, fifth, sixth, seventh, eighth and ninth non-limiting embodiments are further modified so that activation of the intervention button by touch or pressure causes operation of a pump of the cardiopulmonary bypass system to be temporarily modified so as to interrupt an automatic blood fluid level correction mechanism initiated by the processor.

In accordance with an eleventh non-limiting illustrative embodiment of this disclosure, the first, second, third, fourth, fifth, sixth, seventh, eighth, ninth and tenth non-limiting embodiments are further modified so that each tabbed display page comprises a tab, and wherein each tabbed display page is displayable in a displayed mode and in an overlaid mode. In accordance with a twelfth non-limiting illustrative embodiment of this disclosure, the first, second, third, fourth, fifth, sixth, seventh, eighth, ninth, tenth and eleventh non-limiting embodiments are further modified so that when displayed in the displayed mode substantially all of the tabbed display page is viewable, and when displayed in the overlaid mode only the tab of the tabbed display page is viewable. In accordance with a thirteenth non-limiting illustrative embodiment of this disclosure, the first, second, third, fourth, fifth, sixth, seventh, eighth, ninth, tenth, eleventh and twelfth non-limiting embodiments are further modified so that only one tabbed display page of the at least one section that displays the plurality of tabbed display pages is displayed in the displayed mode at a time, and the rest of the tabbed display pages are displayed in the overlaid mode. In accordance with a fourteenth non-limiting illustrative embodiment of this disclosure, the first, second, third, fourth, fifth, sixth, seventh, eighth, ninth, tenth, eleventh, twelfth and thirteenth non-limiting embodiments are further modified so that each tab is activatable by touch or pressure exerted on the touch screen by the user, wherein activation of the tab by touch or pressure causes the associated tabbed display page to be displayed in the displayed mode and the rest of the tabbed display pages to be displayed in the overlaid mode. In accordance with a fifteenth non-limiting illustrative embodiment of this disclosure, the first, second, third, fourth, fifth, sixth, seventh, eighth, ninth, tenth, eleventh, twelfth, thirteenth and fourteenth non-limiting embodiments are further modified so that each tab is capable of transitioning to an alarm state so that when the corresponding tabbed display page is displayed in the overlaid mode and any sensor module of the corresponding tabbed display page transitions to an alarm state, the tab transitions to an alarm state that is viewable.

In accordance with a sixteenth non-limiting illustrative embodiment of this disclosure, the first, second, third, fourth, fifth, sixth, seventh, eighth, ninth, tenth, eleventh, twelfth, thirteenth, fourteenth and fifteenth non-limiting embodiments are further modified so that the graphical user interface includes a header portion and a footer portion, wherein the central portion is disposed between the header portion and the footer portion. In accordance with a seventeenth non-limiting illustrative embodiment of this disclosure, the first, second, third, fourth, fifth, sixth, seventh, eighth, ninth, tenth, eleventh, twelfth, thirteenth, fourteenth, fifteenth and sixteenth non-limiting embodiments are further modified so that the cardiopulmonary bypass system further includes (c) a plurality of sensors disposed to measure one or more parameters of an extracorporeal blood flow circuit, wherein the plurality of sensors are operably connected to input measured data pertaining to the one or more parameters to the processor, and wherein each sensor is linked to one of the sensor modules of either the untabbed display page or one of the tabbed display pages so that data measured by the sensor is displayed by the one sensor module.

In accordance with an eighteenth non-limiting illustrative embodiment of this disclosure, the first, second, third, fourth, fifth, sixth, seventh, eighth, ninth, tenth, eleventh, twelfth, thirteenth, fourteenth, fifteenth, sixteenth and seventeenth non-limiting embodiments are further modified so that the plurality of tabbed display pages include a patient monitor tabbed display page having a patient monitor configuration. In accordance with a nineteenth non-limiting embodiment of this disclosure, the first, second, third, fourth, fifth, sixth, seventh, eighth, ninth, tenth, eleventh, twelfth, thirteenth, fourteenth, fifteenth, sixteenth, seventeenth and eighteenth non-limiting embodiments are modified so that the cardiopulmonary bypass system further includes (d) a third section and a fourth section, wherein the third section includes a simulator keypad tabbed display page having a simulator keypad configuration and the fourth section includes a simulator screen tabbed display page having a simulator screen configuration, wherein when the patient monitor tabbed display page, the simulator keypad tabbed display page and the simulator screen tabbed display page are displayed simultaneously, the patient monitor tabbed display page, the simulator keypad tabbed display page and the simulator screen tabbed display page are operable together as a clinical parameter monitoring and simulation user interface. In accordance with a twentieth non-limiting illustrative embodiment of this disclosure, the first, second, third, fourth, fifth, sixth, seventh, eighth, ninth, tenth, eleventh, twelfth, thirteenth, fourteenth, fifteenth, sixteenth, seventeenth, eighteenth and nineteenth non-limiting embodiments are further modified so that the patient monitoring configuration includes a data value field that displays blood lactate level, and optionally the untabbed display page includes a timer module.

In accordance with a twenty-first non-limiting illustrative embodiment of this disclosure, a touchscreen is provided that includes a graphical user interface, wherein the graphical user interface includes: (a) a header portion; and (b) a central portion adjacent to the header portion, wherein the central portion is divided into a plurality of sections, wherein at least one section displays an untabbed page and at least one section displays a plurality of tabbed pages, and wherein the untabbed page comprises a plurality of sensor modules and the at least one tabbed page comprises a plurality of sensor modules. In accordance with a twenty-second non-limiting illustrative embodiment of this disclosure, the twenty-first non-limiting embodiment is modified so that each sensor module of the untabbed page is individually selected from the group consisting of a pressure sensor module, a bubble detection sensor module, a level sensor module, a flow sensor module, a pressure delta data sensor module and a temperature sensor module. In accordance with a twenty-third non-limiting illustrative embodiment of this disclosure, the twenty-first and twenty-second non-limiting embodiments are further modified so that the untabbed page includes at least one pressure sensor module, at least one bubble detection sensor module, and at least one level sensor module. In accordance with a twenty-fourth non-limiting illustrative embodiment of this disclosure, the twenty-first, twenty-second and twenty-third non-limiting embodiments are further modified so that each of the at least one pressure sensor module, the at least one bubble detection sensor module, and the at least one level sensor module is capable of displaying a plurality of alarm states selected from at least two of a high priority alarm state, a medium priority alarm state, and a low priority alarm state.

In accordance with a twenty-fifth non-limiting illustrative embodiment of this disclosure, the twenty-first, twenty-second, twenty-third and twenty-fourth non-limiting embodiments are further modified so that the at least one pressure sensor module comprises a pressure value data field and a touch or pressure activated intervention button, wherein activation of the intervention button by touch or pressure causes operation of a pump of a cardiopulmonary bypass system to be temporarily modified. In accordance with a twenty-sixth non-limiting illustrative embodiment of this disclosure, the twenty-first, twenty-second, twenty-third, twenty-fourth and twenty-fifth non-limiting embodiments are further modified so that the at least one bubble detection sensor module comprises a bubble detection data field and a touch or pressure activated reset button, wherein the bubble detection data field displays bubble detection data obtained from a bubble detection sensor. In accordance with a twenty-seventh non-limiting illustrative embodiment of this disclosure, the twenty-first, twenty-second, twenty-third, twenty-fourth, twenty-fifth and twenty-sixth non-limiting embodiments are further modified so that the at least one bubble detection sensor module displays a high priority alarm state when the bubble detection sensor detects bubbles exceeding a preset bubble detection size value, and the bubble detection sensor module continues to display the high priority alarm state until the reset button is activated by touch or pressure and the bubbles detected by the bubble detection sensor concurrently do not exceed the preset bubble detection size value. In accordance with a twenty-eighth non-limiting illustrative embodiment of this disclosure, the twenty-first, twenty-second, twenty-third, twenty-fourth, twenty-fifth, twenty-sixth and twenty-seventh non-limiting embodiments are further modified so that at least one bubble detection sensor module further comprises a touch or pressure activated intervention button, wherein activation of the intervention button by touch or pressure causes operation of a pump of a cardiopulmonary bypass system to be temporarily modified.

In accordance with a twenty-ninth non-limiting illustrative embodiment of this disclosure, the twenty-first, twenty-second, twenty-third, twenty-fourth, twenty-fifth, twenty-sixth, twenty-seventh and twenty-eighth non-limiting embodiments are further modified so that the at least one level sensor module comprises a level data field and a touch or pressure activated intervention button, wherein the intervention button is only enabled when a blood fluid level of a blood reservoir of the cardiopulmonary bypass system is at or below a predetermined low blood fluid level. In accordance with a thirtieth non-limiting illustrative embodiment of this disclosure, the twenty-first, twenty-second, twenty-third, twenty-fourth, twenty-fifth, twenty-sixth, twenty-seventh, twenty-eighth and twenty-ninth non-limiting embodiments are further modified so that activation of the intervention button by touch or pressure causes operation of a pump of the cardiopulmonary bypass system to be temporarily modified so as to interrupt an automatic blood fluid level correction mechanism initiated by the processor.

In accordance with a thirty-first non-limiting illustrative embodiment of this disclosure, the twenty-first, twenty-second, twenty-third, twenty-fourth, twenty-fifth, twenty-sixth, twenty-seventh, twenty-eighth, twenty-ninth and thirtieth non-limiting embodiments are further modified so that each tabbed page comprises a tab, and wherein each tabbed page is displayable in a displayed mode and in an overlaid mode. In accordance with a thirty-second non-limiting illustrative embodiment of this disclosure, the twenty-first, twenty-second, twenty-third, twenty-fourth, twenty-fifth, twenty-sixth, twenty-seventh, twenty-eighth, twenty-ninth, thirtieth and thirty-first non-limiting embodiments are further modified so that when displayed in the displayed mode substantially all of the tabbed page is viewable, and when displayed in the overlaid mode only the tab of the tabbed page is viewable. In accordance with a thirty-third non-limiting embodiment of this disclosure, the twenty-first, twenty-second, twenty-third, twenty-fourth, twenty-fifth, twenty-sixth, twenty-seventh, twenty-eighth, twenty-ninth, thirtieth, thirty-first and thirty-second non-limiting embodiments are further modified so that only one tabbed page of the at least one section that displays the plurality of tabbed pages is displayed in the displayed mode at a time, and the rest of the tabbed pages are displayed in the overlaid mode. In accordance with a thirty-fourth non-limiting illustrative embodiment of this disclosure, the twenty-first, twenty-second, twenty-third, twenty-fourth, twenty-fifth, twenty-sixth, twenty-seventh, twenty-eighth, twenty-ninth, thirtieth, thirty-first, thirty-second and thirty-third non-limiting embodiments are further modified so that each tab is activatable by touch or pressure exerted on the touchscreen by the user, wherein activation of the tab by touch or pressure causes the associated tabbed page to be displayed in the displayed mode and the rest of the tabbed pages to be displayed in the overlaid mode. In accordance with a thirty-fifth non-limiting illustrative embodiment of this disclosure, the twenty-first, twenty-second, twenty-third, twenty-fourth, twenty-fifth, twenty-sixth, twenty-seventh, twenty-eighth, twenty-ninth, thirtieth, thirty-first, thirty-second, thirty-third and thirty-fourth non-limiting embodiments are further modified so that each tab is capable of transitioning to an alarm state so that when the corresponding tabbed page is displayed in the overlaid mode and any sensor module of the corresponding tabbed page transitions to an alarm state, the tab transitions to an alarm state that is viewable. In accordance with a thirty-sixth non-limiting illustrative embodiment of this disclosure, the twenty-first, twenty-second, twenty-third, twenty-fourth, twenty-fifth, twenty-sixth, twenty-seventh, twenty-eighth, twenty-ninth, thirtieth, thirty-first, thirty-second, thirty-third, thirty-fourth and thirty-fifth non-limiting embodiments are further modified so that the graphical user interface includes a header portion and a footer portion, wherein the central portion is disposed between the header portion and the footer portion.

In accordance with a thirty-seventh non-limiting illustrative embodiment of this disclosure, a touchscreen is provided with a graphical user interface, wherein the graphical user interface includes a central portion divided into a plurality of sections, wherein one section displays an untabbed display page and a plurality of other sections each displays a plurality of tabbed display pages, wherein each tabbed display page is displayable in a display mode and in an overlaid mode, wherein only one tabbed display page of each of the other sections is displayable in the display mode at one time and each remaining tabbed display page is displayed in the overlaid mode. In accordance with a thirty-eighth non-limiting illustrative embodiment of this disclosure, the thirty-seventh non-limiting embodiment is modified so that each tabbed display page comprises a touch or pressure activatable tab so that touch or pressure applied to the tab activates display of the tabbed display page in the display mode. In accordance with a thirty-ninth non-limiting illustrative embodiment of this disclosure, the thirty-seventh and thirty-eighth non-limiting embodiments are modified so that the plurality of other sections include a first section and a second section, wherein a tabbed display page of the first section is displayed in the displayed mode at the same time as a tabbed display page of the second section in order to form a themed user interface comprising a doublet pair of tabbed display pages. In accordance with a fortieth non-limiting illustrative embodiment of this disclosure, the thirty-seventh, thirty-eighth and thirty-ninth non-limiting embodiments are further modified so that the plurality of other sections include a first section, a second section and a third section, wherein a tabbed display page of the first section is displayed in the displayed mode at the same time as one tabbed display page of the second section or the third section in order to form a themed user interface comprising a doublet pair of tabbed display pages. In accordance with a forty-first non-limiting illustrative embodiment of this disclosure, the thirty-seventh, thirty-eighth, thirty-ninth and fortieth non-limiting embodiments are further modified so that the plurality of other sections include a first section, a second section and a third section, wherein a tabbed display page of the first section is displayed in the displayed mode at the same time as one tabbed display page of the second section and one tabbed display page of the third section in order to form a themed user interface comprising a triplet pair of tabbed display pages.

In accordance with a forty-second non-limiting illustrative embodiment of this disclosure, the thirty-seventh, thirty-eighth, thirty-ninth, fortieth and forty-first non-limiting embodiments are further modified so that the touchscreen further includes a header portion and a footer portion, wherein the central portion is adjacent each of the header portion and the footer portion. In accordance with a forty-third non-limiting illustrative embodiment of this disclosure, a medical apparatus is provided that includes the touchscreen according to any one of the thirty-seventh, thirty-eighth, thirty-ninth, fortieth, forty-first and forty-second non-limiting embodiments. In accordance with a forty-fourth non-limiting illustrative embodiment of this disclosure, the thirty-seventh, thirty-eighth, thirty-ninth, fortieth, forty-first, forty-second and forty-third non-limiting embodiments are further modified so that the untabbed display page comprises a plurality of sensor modules and at least some of the tabbed display pages comprise a plurality of sensor modules. In accordance with a forty-fifth non-limiting illustrative embodiment of this disclosure, the thirty-seventh, thirty-eighth, thirty-ninth, fortieth, forty-first, forty-second, forty-third and forty-fourth non-limiting embodiments are further modified so that the medical apparatus is an apparatus selected from the group consisting of a heart-lung machine and an extracorporeal membrane oxygenation machine.

In accordance with a forty-sixth non-limiting illustrative embodiment of this disclosure, a method of operating a graphical user interface of a medical apparatus is provided, which includes the steps of: (a) selectively configuring a plurality of sensor modules of an untabbed display page of the graphical user interface to display data collected by a first plurality of sensors and to display alarm states associated with the displayed data collected by the first plurality of sensors, wherein the first plurality of sensors are disposed to collect data from an extracorporeal blood flow circuit; and (b) selectively configuring a plurality of sensor modules of a plurality of tabbed display pages of the graphical user interface to display data collected by a second plurality of sensors and to display alarm states associated with the displayed data collected by the second plurality of sensors, wherein the second plurality of sensors are disposed to collect data from the extracorporeal blood flow circuit. In accordance with a forty-seventh non-limiting illustrative embodiment of this disclosure, the forty-sixth non-limiting embodiment is modified so that the alarm states associated with the data displayed by the first plurality of sensors include two or more states selected from the group consisting of a low priority alarm state, a medium priority alarm state and a high priority alarm state. In accordance with a forty-eighth non-limiting illustrative embodiment of this disclosure, the forty-six and forty-seventh non-limiting embodiments of this disclosure are further modified so that the alarm states associated with the data displayed by the second plurality of sensors include two or more states selected from the group consisting of a low priority alarm state, a medium priority alarm state and a high priority alarm state. In accordance with a forty-ninth non-limiting illustrative embodiment of this disclosure, the forty-sixth, forty-seventh and forty-eighth non-limiting embodiments are further modified so that the plurality of sensor modules of the untabbed display page include at least one pressure sensor module, at least one bubble detection sensor module, and at least one level sensor module.

In accordance with a fiftieth non-limiting illustrative embodiment of this disclosure, the methods according to the forty-sixth, forty-seventh, forty-eighth and forty-ninth non-limiting embodiments are further modified to further include the steps of (c) displaying pressure data collected by a pressure sensor operably linked to the at least one pressure sensor module; and (d) displaying a pressure high priority alarm state when the displayed pressure data is equal to or exceeds a stop limit value. In accordance with a fifty-first non-limiting illustrative embodiment of this disclosure, the forty-sixth, forty-seventh, forty-eighth, forty-ninth and fiftieth non-limiting embodiments are further modified to include the step of displaying a pressure medium priority alarm state when the pressure data is equal to or exceeds a threshold value and is lower than the stop limit value. In accordance with a fifty-second non-limiting illustrative embodiment of this disclosure, the forty-sixth, forty-seventh, forty-eighth, forty-ninth, fiftieth and fifty-first non-limiting embodiments are further modified to include the step of displaying a pressure low priority alarm state when the pressure data is equal to or exceeds an alarm limit value and is lower than the threshold value. In accordance with a fifty-third non-limiting embodiment of this disclosure, the forty-sixth, forty-seventh, forty-eighth, forty-ninth, fiftieth, fifty-first and fifty-second non-limiting embodiments are further modified to include the step of activating a touch or pressure sensitive intervention button of a touch screen while the pressure high priority alarm state is displayed, wherein activation of the touch or pressure sensitive intervention button reduces or interrupts operation of a blood pump.

In accordance with a fifty-fourth non-limiting embodiment of this disclosure, the forty-sixth, forty-seventh, forty-eighth, forty-ninth, fiftieth, fifty-first, fifty-second and fifty-third non-limiting embodiments are further modified to include the steps of displaying bubble detection data collected by a bubble detection sensor operably linked to the at least one bubble detection sensor module; and displaying a bubble detection low priority alarm state when the displayed bubble detection data indicates detection of bubbles in the extracorporeal blood flow circuit and the detected bubbles have a size that does not exceed a threshold size limit value. In accordance with a fifty-fifth non-limiting illustrative embodiment of this disclosure, the forty-sixth, forty-seventh, forty-eighth, forty-ninth, fiftieth, fifty-first, fifty-second, fifty-third and fifty-fourth non-limiting embodiments are further modified to include the step of displaying a bubble detection high priority alarm state when the displayed bubble detection data indicates detection of bubbles in the extracorporeal blood flow circuit that have a size exceeding the threshold size limit value, and continuing display of the bubble detection high priority alarm state until the size of detected bubbles do not exceed the threshold size limit value and a reset button has been activated. In accordance with a fifty-sixth non-limiting embodiment of this disclosure, the forty-sixth, forty-seventh, forty-eighth, forty-ninth, fiftieth, fifty-first, fifty-second, fifty-third, fifty-fourth and fifty-fifth non-limiting embodiments are further modified to include the step of activating a touch or pressure sensitive intervention button of a touch screen while the bubble detection high priority alarm state is displayed, wherein activation of the touch or pressure sensitive intervention button modifies operation of a blood pump for a set period of time.

In accordance with a fifth-seventh non-limiting illustrative embodiment of this disclosure, the forty-sixth, forty-seventh, forty-eighth, forty-ninth, fiftieth, fifty-first, fifty-second, fifty-third, fifty-fourth, fifty-fifth and fifty-sixth non-limiting embodiments are further modified to include the steps of displaying level data collected by a level sensor operably linked to the at least one level sensor module; and displaying a level low priority alarm state when the displayed level data indicates a level of blood fluid of a blood reservoir of the extracorporeal blood flow circuit that is at or below a regulation level and exceeds an unacceptably low level. In accordance with a fifty-eighth non-limiting illustrative embodiment of this disclosure, the forty-sixth, forty-seventh, forty-eighth, forty-ninth, fiftieth, fifty-first, fifty-second, fifty-third, fifty-fourth, fifty-fifth, fifty-sixth and fifty-seventh non-limiting embodiments are further modified to include the step of displaying a level high priority alarm state when the displayed level data indicates the level of blood fluid of the blood reservoir of the extracorporeal blood flow circuit is at or below the unacceptably low level. In accordance with a fifty-ninth non-limiting illustrative embodiment of this disclosure, the forty-sixth, forty-seventh, forty-eighth, forty-ninth, fiftieth, fifty-first, fifty-second, fifty-third, fifty-fourth, fifty-fifth, fifty-sixth, fifty-seventh and fifty-eighth non-limiting embodiments are further modified to include the step of activating a touch or pressure sensitive intervention button of a touch screen while the level high priority alarm state is displayed, wherein activation of the touch or pressure sensitive intervention button modifies either operation of an arterial blood pump for a set period of time or modifies operation of an air removal pump for a set period of time.

In accordance with a sixtieth non-limiting illustrative embodiment of this disclosure, the forty-sixth, forty-seventh, forty-eighth, forty-ninth, fiftieth, fifty-first, fifty-second, fifty-third, fifty-fourth, fifty-fifth, fifty-sixth, fifty-seventh, fifty-eighth and fifty-ninth non-limiting embodiments are further modified so that the plurality of sensor modules of the tabbed display page include at least one sensor module selected from the group consisting of a pressure sensor module, a bubble detection sensor module, a level sensor module, a temperature sensor module, and a flow sensor module. In accordance with a sixty-first non-limiting illustrative embodiment of this disclosure, the forty-sixth, forty-seventh, forty-eighth, forty-ninth, fiftieth, fifty-first, fifty-second, fifty-third, fifty-fourth, fifty-fifth, fifty-sixth, fifty-seventh, fifty-eighth, fifty-ninth and sixtieth non-limiting embodiments are further modified to include the steps of displaying pressure data collected by a pressure sensor operably linked to the pressure sensor module; and displaying a pressure high priority alarm state when the displayed pressure data is equal to or exceeds a stop limit value. In accordance with a sixty-second non-limiting illustrative embodiment of this disclosure, the forty-sixth, forty-seventh, forty-eighth, forty-ninth, fiftieth, fifty-first, fifty-second, fifty-third, fifty-fourth, fifty-fifth, fifty-sixth, fifty-seventh, fifty-eighth, fifty-ninth, sixtieth and sixty-first non-limiting embodiments are further modified to include the step of displaying a pressure medium priority alarm state when the pressure data is equal to or exceeds a threshold value and is lower than the stop limit value. In accordance with a sixty-third non-limiting illustrative embodiment of this disclosure, the forty-sixth, forty-seventh, forty-eighth, forty-ninth, fiftieth, fifty-first, fifty-second, fifty-third, fifty-fourth, fifty-fifth, fifty-sixth, fifty-seventh, fifty-eighth, fifty-ninth, sixtieth, sixty-first and sixty-second non-limiting embodiments are further modified to include the step of displaying a pressure low priority alarm state when the pressure data is equal to or exceeds an alarm limit value and is lower than the threshold value. In accordance with a sixty-fourth non-limiting illustrative embodiment of this disclosure, the forty-sixth, forty-seventh, forty-eighth, forty-ninth, fiftieth, fifty-first, fifty-second, fifty-third, fifty-fourth, fifty-fifth, fifty-sixth, fifty-seventh, fifty-eighth, fifty-ninth, sixtieth, sixty-first, sixty-second and sixty-third non-limiting embodiments are further modified to include the step of activating a touch or pressure sensitive intervention button of a touch screen while the pressure high priority alarm state is displayed, wherein activation of the touch or pressure sensitive intervention button reduces or interrupts operation of a blood pump.

In accordance with a sixty-fifth non-limiting illustrative embodiment of this disclosure, the forty-sixth, forty-seventh, forty-eighth, forty-ninth, fiftieth, fifty-first, fifty-second, fifty-third, fifty-fourth, fifty-fifth, fifty-sixth, fifty-seventh, fifty-eighth, fifty-ninth, sixtieth, sixty-first, sixty-second, sixty-third and sixty-fourth non-limiting embodiments are further modified to include the steps of displaying bubble detection data collected by a bubble detection sensor operably linked to the bubble detection sensor module; and displaying a bubble detection low priority alarm state when the displayed bubble detection data indicates detection of bubbles in the extracorporeal blood flow circuit and the detected bubbles have a size that does not exceed a threshold size limit value. In accordance with a sixty-sixth non-limiting illustrative embodiment of this disclosure, the forty-sixth, forty-seventh, forty-eighth, forty-ninth, fiftieth, fifty-first, fifty-second, fifty-third, fifty-fourth, fifty-fifth, fifty-sixth, fifty-seventh, fifty-eighth, fifty-ninth, sixtieth, sixty-first, sixty-second, sixty-third, sixty-fourth and sixty-fifth non-limiting embodiments are further modified to include the step of displaying a bubble detection high priority alarm state when the displayed bubble detection data indicates detection of bubbles in the extracorporeal blood flow circuit that have a size exceeding the threshold size limit value, and continuing display of the bubble detection high priority alarm state until the size of detected bubbles do not exceed the threshold size limit value and a reset button has been activated. In accordance with a sixty-seventh non-limiting illustrative embodiment of this disclosure, the forty-sixth, forty-seventh, forty-eighth, forty-ninth, fiftieth, fifty-first, fifty-second, fifty-third, fifty-fourth, fifty-fifth, fifty-sixth, fifty-seventh, fifty-eighth, fifty-ninth, sixtieth, sixty-first, sixty-second, sixty-third, sixty-fourth, sixty-fifth and sixty-sixth non-limiting embodiments are further modified to include the step of activating a touch or pressure sensitive intervention button of a touch screen while the bubble detection high priority alarm state is displayed, wherein activation of the touch or pressure sensitive intervention button modifies operation of a blood pump for a set period of time.

In accordance with a sixty-eighth non-limiting illustrative embodiment of this disclosure, the forty-sixth, forty-seventh, forty-eighth, forty-ninth, fiftieth, fifty-first, fifty-second, fifty-third, fifty-fourth, fifty-fifth, fifty-sixth, fifty-seventh, fifty-eighth, fifty-ninth, sixtieth, sixty-first, sixty-second, sixty-third, sixty-fourth, sixty-fifth, sixty-sixth and sixty-seventh non-limiting embodiments are further modified to include the steps of displaying level data collected by a level sensor operably linked to the level sensor module; and displaying a level low priority alarm state when the displayed level data indicates a level of blood fluid of a blood reservoir of the extracorporeal blood flow circuit that is at or below a regulation level and exceeds an unacceptably low level. In accordance with a sixty-ninth non-limiting illustrative embodiment of this disclosure, the forty-sixth, forty-seventh, forty-eighth, forty-ninth, fiftieth, fifty-first, fifty-second, fifty-third, fifty-fourth, fifty-fifth, fifty-sixth, fifty-seventh, fifty-eighth, fifty-ninth, sixtieth, sixty-first, sixty-second, sixty-third, sixty-fourth, sixty-fifth, sixty-sixth, sixty-seventh and sixty-eighth non-limiting embodiments are further modified to include the step of displaying a level high priority alarm state when the displayed level data indicates the level of the blood fluid of the blood reservoir of the extracorporeal blood flow circuit is at or below the unacceptably low level. In accordance with a seventieth non-limiting illustrative embodiment of this disclosure, the forty-sixth, forty-seventh, forty-eighth, forty-ninth, fiftieth, fifty-first, fifty-second, fifty-third, fifty-fourth, fifty-fifth, fifty-sixth, fifty-seventh, fifty-eighth, fifty-ninth, sixtieth, sixty-first, sixty-second, sixty-third, sixty-fourth, sixty-fifth, sixty-sixth, sixty-seventh, sixty-eighth and sixty-ninth non-limiting embodiments are further modified to include the step of activating a touch or pressure sensitive intervention button of a touch screen while the level high priority alarm state is displayed, wherein activation of the touch or pressure sensitive intervention button modifies either operation of an arterial blood pump for a set period of time or modifies operation of an air removal pump for a set period of time.

In accordance with a seventy-first non-limiting illustrative embodiment of this disclosure, the forty-sixth, forty-seventh, forty-eighth, forty-ninth, fiftieth, fifty-first, fifty-second, fifty-third, fifty-fourth, fifty-fifth, fifty-sixth, fifty-seventh, fifty-eighth, fifty-ninth, sixtieth, sixty-first, sixty-second, sixty-third, sixty-fourth, sixty-fifth, sixty-sixth, sixty-seventh, sixty-eighth, sixty-ninth and seventieth non-limiting embodiments are further modified so that multiple tabbed display pages are displayed within a first section of the graphical user interface and the untabbed display page is displayed within a second section of the graphical user interface, and each tabbed display page is displayable in a display mode and in an overlaid mode, and the method further includes the step of activating a tab of a tabbed display page of the first section so that the tabbed display page is displayed in the display mode and so that every other tabbed display page of the first section is displayed in the overlaid mode. In accordance with a seventy-second non-limiting illustrative embodiment of this disclosure, the forty-sixth, forty-seventh, forty-eighth, forty-ninth, fiftieth, fifty-first, fifty-second, fifty-third, fifty-fourth, fifty-fifth, fifty-sixth, fifty-seventh, fifty-eighth, fifty-ninth, sixtieth, sixty-first, sixty-second, sixty-third, sixty-fourth, sixty-fifth, sixty-sixth, sixty-seventh, sixty-eighth, sixty-ninth, seventieth and seventy-first non-limiting embodiments are further modified so that, when in the display mode, substantially all of the tabbed display page is displayed and in the overlaid mode substantially only all of the tab of the tabbed display page is displayed. In accordance with a seventy-third non-limiting embodiment of this disclosure, the forty-sixth, forty-seventh, forty-eighth, forty-ninth, fiftieth, fifty-first, fifty-second, fifty-third, fifty-fourth, fifty-fifth, fifty-sixth, fifty-seventh, fifty-eighth, fifty-ninth, sixtieth, sixty-first, sixty-second, sixty-third, sixty-fourth, sixty-fifth, sixty-sixth, sixty-seventh, sixty-eighth, sixty-ninth, seventieth, seventy-first and seventy-second non-limiting embodiments are further modified so that while displayed in the overlaid mode, alarm states of the overlaid tabbed display pages are signaled by the tabs of the overlaid tabbed display pages.

In accordance with a seventy-fourth non-limiting illustrative embodiment of this disclosure, a method of configuring a graphical user interface of a touchscreen prior to operation in a clinical operation mode is provided, wherein the method includes the steps of: (a) in response to a first signal, displaying a sensor module configuration menu interface associated with a tabbed display page of the graphical user interface displayed by the touchscreen; and (b) in response to a second signal, setting at least one alarm limit for a sensor module associated with the sensor module configuration menu interface associated with the tabbed display page. In accordance with a seventy-fifth non-limiting illustrative embodiment of this disclosure, the seventy-fourth non-limiting embodiment is modified so that the first signal is generated as a result of activation of a touch or pressure activatable module settings menu button of the sensor module of the tabbed display page. In accordance with a seventy-sixth non-limiting illustrative embodiment of this disclosure, the seventy-fourth and seventy-fifth non-limiting embodiments are modified so that the second signal is generated as a result of activation of a touch or pressure activatable button of the sensor module configuration menu interface of the tabbed display page. In accordance with a seventy-seventh non-limiting illustrative embodiment of this disclosure, the seventy-fourth, seventy-fifth and seventy-sixth non-limiting embodiments are further modified so the method includes the step of, in response to a third signal, overlaying a pump association menu interface on a portion of the sensor module configuration menu interface of the tabbed display page in order to enable a selective association of a pump function with the sensor module of the tabbed display page.

In accordance with a seventy-eighth non-limiting embodiment of this disclosure, the seventy-fourth, seventy-fifth, seventy-sixth and seventy-seventh non-limiting embodiments are further modified so, in response to a third signal, a sensor module configuration menu interface is displayed on a portion of an untabbed display page of the graphical user interface displayed by the touchscreen; and, in response to a fourth signal, at least one alarm limit is set for a sensor module associated with the sensor module configuration menu interface associated with the untabbed display page. In accordance with a seventy-ninth non-limiting illustrative embodiment of this disclosure, the seventy-fourth, seventy-fifth, seventy-sixth, seventy-seventh and seventy-eighth non-limiting embodiments are further modified so the third signal is generated as a result of activation of a touch or pressure activatable module settings menu button of the sensor module of the untabbed display page. In accordance with an eightieth non-limiting illustrative embodiment of this disclosure, the seventy-fourth, seventy-fifth, seventy-sixth, seventy-seventh, seventy-eighth and seventy-ninth non-limiting embodiments are further modified so the fourth signal is generated as a result of activation of a touch or pressure activatable button of the sensor module configuration menu interface of the untabbed display page. In accordance with an eighty-first non-limiting embodiment of this disclosure, the seventy-fourth, seventy-fifth, seventy-sixth, seventy-seventh, seventy-eighth, seventy-ninth and eightieth non-limiting embodiments are further modified to include the step of, in response to a fifth signal, overlaying a pump association menu interface on a portion of the sensor module configuration menu interface of the untabbed display page in order to enable a selective association of a pump function with the sensor module of the untabbed display page.

In accordance with an eighty-second non-limiting illustrative embodiment of this disclosure, the seventy-fourth, seventy-fifth, seventy-sixth, seventy-seventh, seventy-eighth, seventy-ninth, eightieth and eighty-first non-limiting embodiments are further modified so that the sensor module associated with the sensor module configuration menu interface is a pressure sensor module associated with a pressure sensor module configuration menu interface, or a bubble detection sensor module associated with a bubble detection sensor module configuration menu interface, or a level sensor module associated with a level sensor module configuration menu interface, or a temperature sensor module associated with a temperature sensor module configuration menu interface, or a flow sensor module associated with a flow sensor module configuration menu interface, or a pressure delta sensor module associated with a pressure delta sensor module configuration menu interface. In accordance with an eighty-third non-limiting illustrative embodiment of this disclosure, the seventy-eighth non-limiting embodiment is further modified so that each sensor module associated with the corresponding sensor module configuration menu interface is independently selected from the group consisting of a pressure sensor module associated with a pressure sensor module configuration menu interface, a bubble detection sensor module associated with a bubble detection sensor module configuration menu interface, a level sensor module associated with a level module configuration menu interface, a temperature sensor module associated with a temperature sensor module configuration menu interface, a flow sensor module associated with a flow sensor module configuration menu interface, and a pressure delta sensor module associated with a pressure delta sensor module configuration menu interface.

In accordance with an eighty-fourth non-limiting illustrative embodiment of this disclosure, the seventy-fourth, seventy-fifth, seventy-sixth, seventy-seventh, seventy-eighth, seventy-ninth, eightieth, eighty-first, eighty-second and eighty-third non-limiting embodiments are further modified to include the step of activating a system configuration menu interface in order to select a predefined graphical user interface configuration, or configure at least one selectable alarm setting selected from the group consisting of brightness and alarm volume, or display an external device menu. In accordance with an eighty-fifth non-limiting illustrative embodiment of this disclosure, the seventy-fourth, seventy-fifth, seventy-sixth, seventy-seventh, seventy-eighth, seventy-ninth, eightieth, eighty-first, eighty-second, eighty-third and eighty-fourth non-limiting embodiments are further modified to include the step of closing the sensor module configuration menu interface of the tabbed display page so as to accept and enable the at least one alarm limit of the sensor module of the tabbed display page. In accordance with an eighty-sixth non-limiting illustrative embodiment of this disclosure, the seventy-fourth, seventy-fifth, seventy-sixth, seventy-seventh, seventy-eighth, seventy-ninth, eightieth, eighty-first, eighty-second, eighty-third, eighty-fourth and eighty-fifth non-limiting embodiments are further modified to include the step of closing the sensor module configuration menu interface of the untabbed display page in order to accept and enable the at least one alarm limit of the sensor module of the untabbed display page. In accordance with an eighty-seventh non-limiting illustrative embodiment of this disclosure, the seventy-fourth, seventy-fifth, seventy-sixth, seventy-seventh, seventy-eighth, seventy-ninth, eightieth, eighty-first, eighty-second, eighty-third, eighty-fourth, eighty-fifth and eighty-sixth non-limiting embodiments are further modified to include the step of closing the sensor module configuration menu interface of the tabbed display page in order to accept and enable the at least one alarm limit of the sensor module of the tabbed display page.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

FIG. 10a, 10b, 10c, 10d, 10e, 10f, 10g and 10h (which may be collectively referred to as "FIG. 10") illustrate exemplary, non-limiting configurations of a pressure sensor module in accordance with an embodiment of this disclosure.

FIGS. 11a and 11b illustrate exemplary, non-limiting configurations for an intervention button of a pressure sensor module in accordance with an embodiment of this disclosure.

FIG. 12 illustrates an exemplary, non-limiting configuration of a bubble detection sensor module in accordance with an embodiment of this disclosure.

FIGS. 13a, 13b, 13c and 13d (which may be collectively referred to as "FIG. 13") illustrate various bubble level icons in accordance with an embodiment of this disclosure.

FIGS. 19a, 19b, 19c, 19d, 19e, 19f and 19g illustrate several exemplary non-limiting configurations of a temperature sensor module, and/or alarm states thereof, in accordance with an embodiment of this disclosure.

FIGS. 20a, 20b, 20c, 20d, 20e and 20f illustrate several non-limiting configurations of a flow sensor module, and/or alarm states thereof, in accordance with an embodiment of this disclosure.

FIGS. 21a, 21b, 21c and 21d illustrate several non-limiting configurations of a pressure delta sensor module, and/or alarms states thereof, in accordance with an embodiment of this disclosure.

FIGS. 30a, 30b, 30c and 30d (which may be collectively referred to as "FIG. 30") illustrate an exemplary, non-limiting embodiment of a tabbed display page directed to a simulator screen interface of a clinical parameter monitor-simulation user interface in accordance with an embodiment of this disclosure.

DETAILED DESCRIPTION OF THE ILLUSTRATIVE EMBODIMENTS

Figure 1:
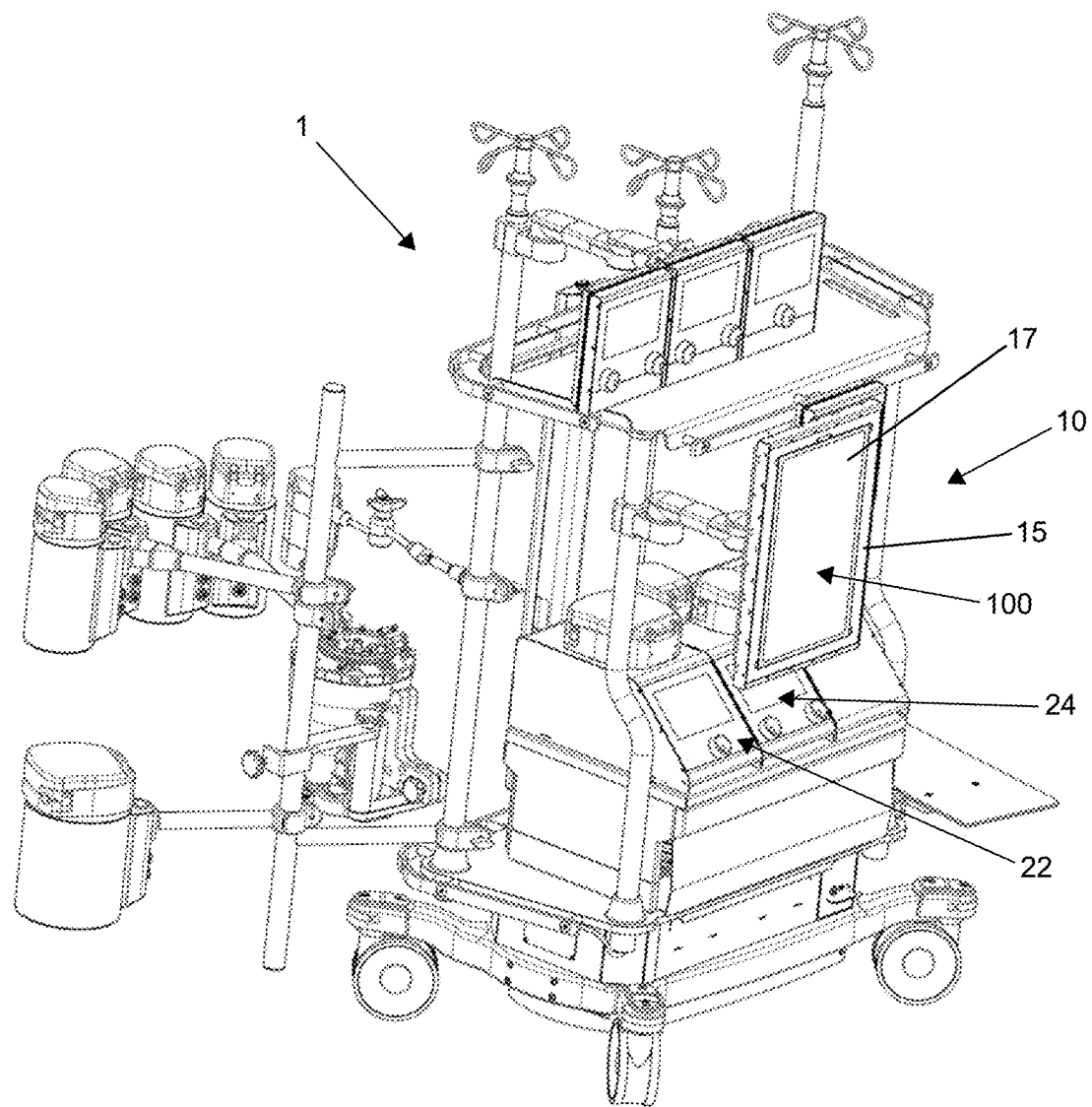
FIG. 1 is a perspective view of an exemplary heart-lung machine including an embodiment of the user interface system of the present disclosure.

For illustrative purposes, the principles of the present disclosure are described by referencing various exemplary, non-limiting embodiments. Thus, although certain embodiments are specifically described herein, one of ordinary skill in the art will readily recognize that the same principles are equally applicable to, and can be employed in other systems and methods. Before explaining the disclosed embodiments in detail, it is to be understood that this disclosure is not limited in its application to the details of any particular embodiment shown. Additionally, the terminology used herein is for the purpose of description and not of limitation. Furthermore, although certain methods are described with reference to steps that are presented herein in a certain order, in many instances, these steps may be performed in any order as may be appreciated by one skilled in the art. The novel method(s) disclosed herein are, therefore, not limited to the particular arrangement of steps disclosed herein.

For purposes of the present application, "display field" as used herein, refers to a field configured to display information on a user interface, and "data field" as used herein refers to a field configured to both display information on a user interface and to enter information into a computer system via the user interface. The term "interface," in accordance with this disclosure, should be construed to refer to a component of a machine that itself is also a machine. Thus, the term "interface" in accordance with this disclosure should not be construed solely as a software application; however, it may be construed as a machine and related embedded software operating as a component of the machine. The term "mechanism" in accordance with this disclosure should be construed to refer to a machine, which may include electromechanical devices and components thereof that are also machines.

In accordance with some embodiments of this disclosure, the term "user interface" pertains to a machine that includes at least two or more of the following features: (i) a set of dials, knobs, and/or touch or pressure operated buttons, (ii) operating system commands, (iii) graphical display formats, and (iv) other devices provided by a computer to allow the user to communicate and use the computer or program operating on the computer. A graphical user interface (GUI) provides its user a more or less "picture-oriented" way to interact with computer technology.

The present disclosure is directed to a user interface system and display configured for use in association with medical apparatuses and systems to facilitate blood perfusion as well as monitoring and/or regulation of various physiological parameters of a patient, corresponding methods for customization, and uses thereof. The user interface system may be part of, integrated in, used in association with and/or supported by the hardware of a cardiopulmonary bypass system, perfusion system, extracorporeal circulation apparatus or heart-lung machine. In an exemplary embodiment, the user interface is a flexible, ergonomic system allowing for user, patient and/or clinical application, with related customizations provided to facilitate intuitive use and ease of use. The user interface system may further facilitate the rapid, efficient and continuous unobstructed access to physiological data and system parameters, and allow for rapid and efficient monitoring, regulation and/or adjustment of system parameters, in part, by minimizing and/or eliminating nesting and nesting depth of menu layers, which otherwise impede data access. On the contrary, the user interface system of this disclosure provides unobstructed placement of menus once opened, which minimizes risks to patient safety caused by obstructed data access. Furthermore, the user interface of this disclosure may include, in accordance with some embodiments, an integrated alarm system with multiple corresponding alarm notices that quickly directs a user's attention to system failures and/or patient parameters that have exceeded threshold values and/or have reached dangerous values, without distracting or preventing the user from operating the medical apparatus and system. In accordance with this disclosure, some embodiments further provide high level and more detailed information regarding each alarm as well as a help menu for explaining and resolving the underlying situation that created the alarm, and assist in alarm prioritization.

To facilitate ease of understanding of the embodiments of this disclosure, a graphical user interface of a user interface system is described, followed by a disclosure of the customizable features of the user interface system.

Graphical User Interface

Figure 2A:
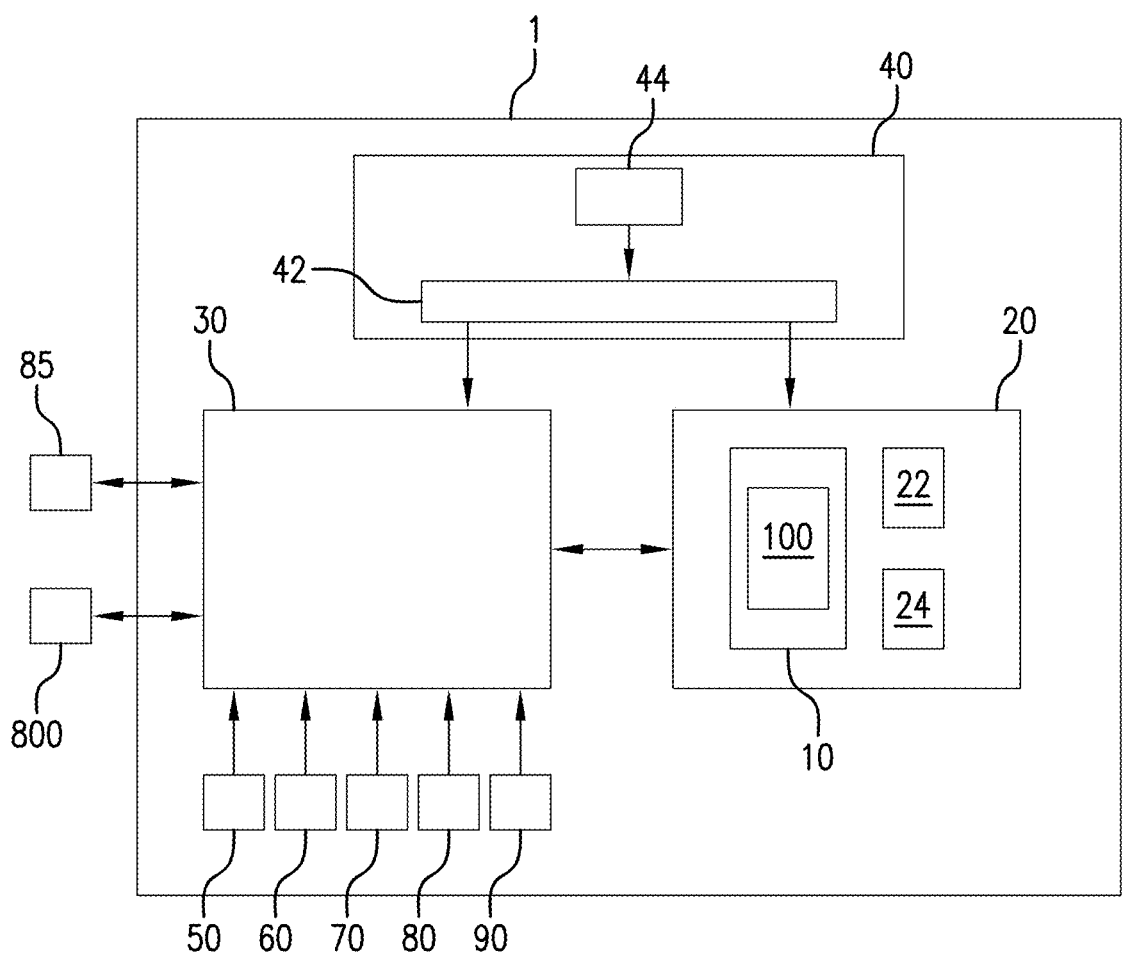
FIG. 2a is a schematic diagram of a user interface system in accordance with an embodiment of this disclosure and its operative connections to various components of the heart-lung machine of FIG. 1.

In accordance with this disclosure, a graphical user interface 100 is a component of the display apparatus 10 of a cardio-pulmonary bypass machine 1, as shown by FIG. 1. The graphical user interface 100 is also a component of a user interface system 20 of the cardio-pulmonary bypass machine 1, as shown by FIG. 2a, which may be integrated with the display apparatus 10. In other words, the display apparatus 10 may incorporate some portion, or all of, the user interface system 20. However, other portions 22, 24 of user interface system 20 may be remote from the display apparatus 10. According to FIG. 2a, the user interface system 20 of the cardio-pulmonary bypass machine 1 is operably connected to send signal inputs to a processor 30 of the cardio-pulmonary bypass machine 1, and to receive signal inputs from the processor 30. Processor 30 may preferably be an embedded system and not a general use computer. Components of the cardiopulmonary bypass machine 1, and its extracorporeal blood flow circuit, may be similar to those of the extracorporeal circulation system disclosed by U.S. Provisional Patent Application No. 62/160,689, filed on May 13, 2015, and it corresponding U.S. Patent Application Publication No. US XXXX/YYYYYYY, both of which are incorporated herein by reference in their entirety for all they disclose.

Figure 2B:
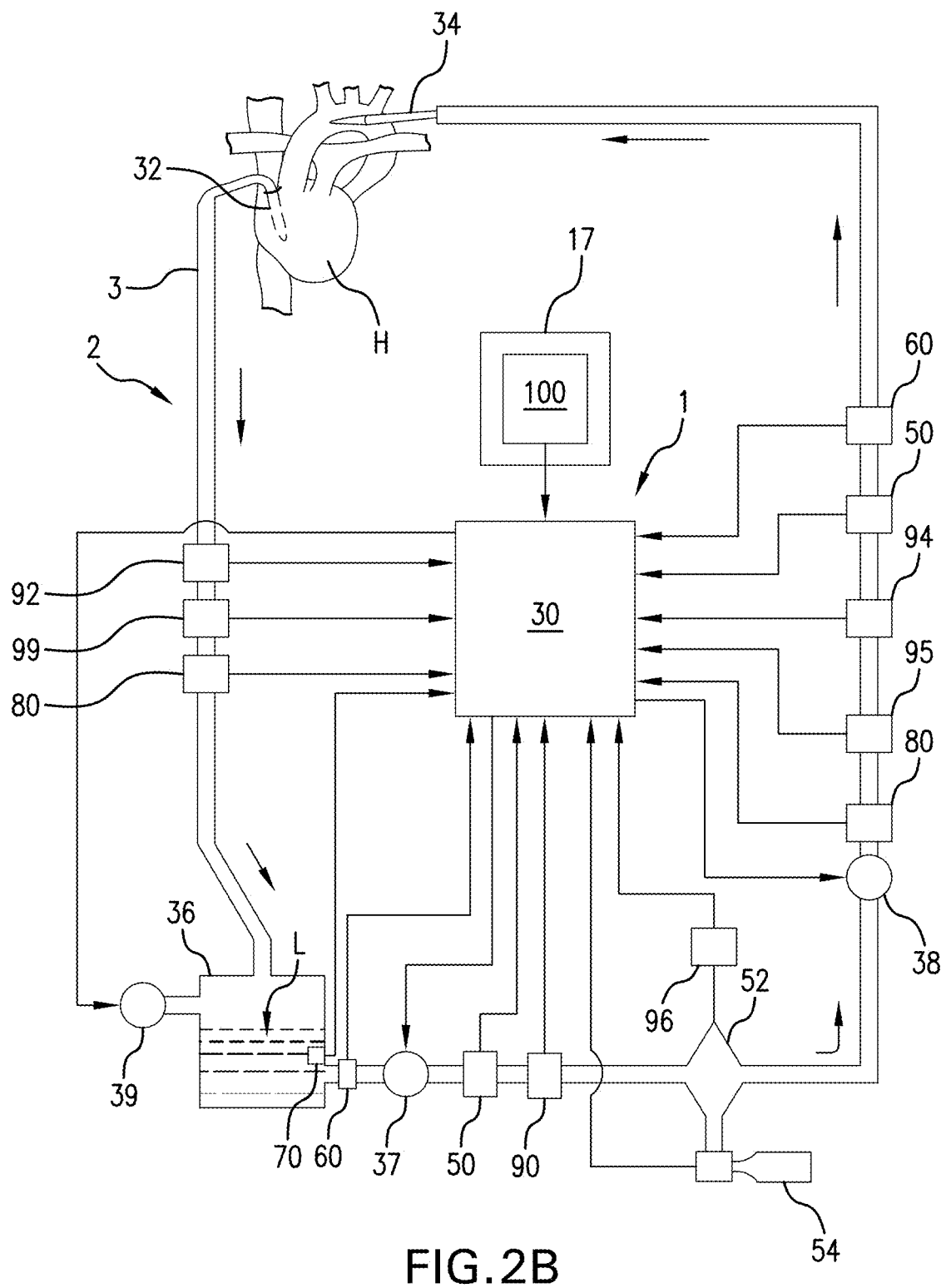
FIG. 2b is a schematic diagram of a cardiopulmonary bypass system that incorporates a heart-lung machine that includes a user interface system of the present disclosure.

FIG. 2b illustrates a graphical user interface 100 of this disclosure as it is integrated with components of a cardio-pulmonary bypass system 2, which incorporates a cardio-pulmonary bypass machine 1 and its extracorporeal blood flow circuit 3, generally constructed of various blood compatible tubing. FIG. 2b is a schematic illustration of the more relevant portions of a cardiopulmonary bypass system 2, so less relevant portions of such a system 2 have been omitted from the drawing. For a non-limiting example of a more detailed illustration of a cardiopulmonary bypass system, one may consult FIG. 1 of Chapter 5 of Glenn P. Gravlee et al., CARDIOPULMONARY BYPASS PRINCIPLES AND PRACTICE ($3^{rd}$ Edition) 63-65 (Lippincott Williams & Wilkins 2008).

With reference to FIG. 2b, venous blood is drawn from the vena cava or right atrium of the heart H through venous catheter 32 into the extracorporeal blood flow circuit 3, travels through the circuit 3, and then enters the aorta through an arterial catheter 34. Venous blood from the heart H traveling through the extracorporeal blood flow circuit 3 passes through a venous blood reservoir 36 and is pumped via one or more venous blood pumps 37 to an oxygenator 52 connected to an oxygen gas source 54, which oxygenates the venous blood, and the oxygenated blood may be pumped via one or more arterial pumps 38 before it returns to the aorta as oxygenated arterial blood via arterial catheter 34. The extracorporeal blood flow circuit 3 may be provided with a number of sensors 50, 60, 70, 80, 90 connected to send data input to the processor 30. Such sensors may include pressure sensors 50, bubble detection sensors 60, temperature sensors 80, and blood flow/pump sensors 90, such as operate to collect pressure data, bubble detection data, temperature data and blood flow data, respectfully, at various points along the extracorporeal blood flow circuit 3. The venous blood reservoir 36 may be provided with one or more level sensors 70 to measure the level of blood fluid collected in the venous blood reservoir 36. The processor 30 may be connected to send control signals to various components of the cardiopulmonary bypass machine 1, such as blood pumps 37, 38 and vacuum pump 39.

In accordance with an embodiment of this disclosure, the processor 30 is optionally connected to receive data input from a venous blood gas sensor assembly 92 and an arterial blood gas sensor assembly 94, which provide data input regarding venous and arterial oxygen saturations ($SvO_2$, $SaO_2$) and corresponding arterial and venous partial pressures ($PvO_2$, $PaO_2$), respectively. The processor 30 may also be connected to receive HCT data input from a HCT sensor 95 and expired carbon dioxide data from a capnograph 96. The processor 30 may also be connected to send control signals to a vacuum pump 39 that is connected to draw a vacuum in the air space of the blood fluid reservoir 36 above the blood fluid level L.

The display apparatus 10 includes a liquid crystal display (LCD) touch-screen monitor 15, and may employ a capacitive touch-screen system, or a resistive touch-screen system, or a surface acoustic touch-screen wave system, or an infrared touch screen system. The graphical user interface 100 of the touch-screen monitor 15 is divided into a header portion 102, a footer portion 104, and a central monitoring portion 106, as shown in FIG. 3. Each of the portions 102, 104 and 106 may be framed by a distinct border 107 in accordance with an embodiment of this disclosure and, therefore, may be construed as panels. However, in accordance with other embodiments of this disclosure, the portions 102, 104 and 106 may have non-descript borders.

Header Portion of the Graphical User Interface

Figure 4:
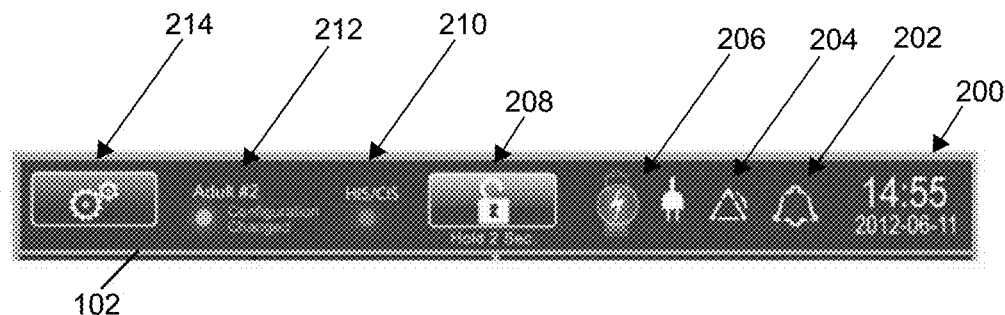
FIG. 4 illustrates an exemplary, non-limiting configuration of a header portion of the graphical user interface of FIG. 3.

The header portion 102 displays various information in one or more display fields that are generally useful for those individuals monitoring the touch-screen monitor 15 of the cardio-pulmonary bypass machine 1. In accordance with an embodiment of this disclosure, as illustrated by FIG. 4, the header portion 102 may include a date and time display field 200 that continuously displays the current date and time. The header portion 102 also includes an audio alarm cancel icon 202 that, when displayed, indicates some audio alarm of the cardio-pulmonary bypass machine 1 has been turned off or inactivated in some way. The audio alarm cancel icon 202 has two states, namely, displayed or blanked (i.e., not fully displayed). When the audio alarm cancel icon 202 is blanked (i.e., is not fully visible), then no audio alarm of the cardio-pulmonary bypass machine 1 has been inactivated, or compromised in any way.

The header portion 102 may also include an alarm cancel icon 204 that, when displayed, indicates some audiovisual alarm of the cardio-pulmonary bypass machine 1 has been turned off or inactivated in some way. The alarm cancel icon 204 has two states, namely, displayed or blanked (i.e., not fully displayed). When the alarm cancel icon 204 is blanked (i.e., is not fully visible), then no viewable non-audio alarm of the cardio-pulmonary bypass machine 1 has been inactivated, or compromised in any way. The audiovisual alarm of the cardio-pulmonary bypass machine 1 has a selectable silent mode in which the audio portion of the audiovisual alarm may be silenced.

Figure 5A:
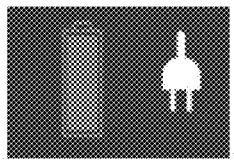
FIGS. 5a, 5b, 5c, 5d, 5e and 5f (which may be collectively referred to as "FIG. 5") illustrate various displayed states for a battery icon of the graphical user interface in accordance with an embodiment of this disclosure.
Figure 5B:
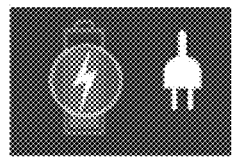
Figure 5C:
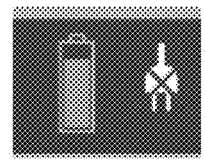
Figure 5D:
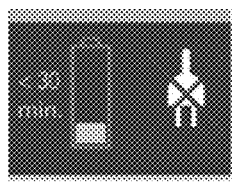
Figure 5E:
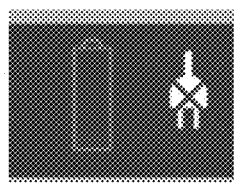
Figure 5F:
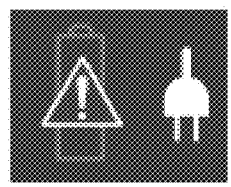

In accordance with an embodiment of this disclosure, the header portion 102 includes a battery icon 206, which displays information regarding the power management system 40 of the cardio-pulmonary bypass machine 1. For example, the battery icon 206 may have substantially different displayed states corresponding to whether the battery 42 of the power management system 40 of the cardiopulmonary bypass machine 1 is (i) fully charged (FIG. 5a), (ii) is charging via a battery recharger 44 of the power management system 40 (FIG. 5b), (iii) is not charging and has an estimated remaining charge sufficient to operate the cardio-pulmonary bypass machine 1 for greater than 30 minutes (FIG. 5c), (iv) is not charging and has an estimated remaining charge sufficient to operate the cardio-pulmonary bypass machine 1 for more than 10 minutes and less than 30 minutes (FIG. 5d), (v) is not charging and has an estimated remaining charge sufficient to operate the cardio-pulmonary bypass machine 1 for less than 10 minutes (FIG. 5e), or (vi) is not useable (FIG. 5f).

Figure 6A:
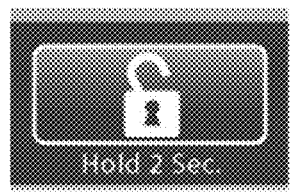
FIGS. 6a and 6b (which may be collectively referred to as "FIG. 6") illustrate various displays corresponding to different operative states of a lock screen button of the graphical user interface in accordance with an embodiment of this disclosure.
Figure 6B:
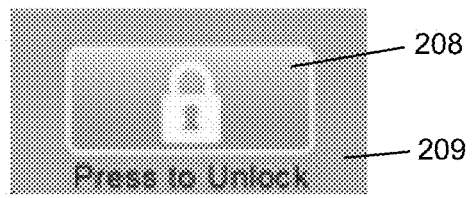

In accordance with an embodiment of this disclosure, the header portion 102 includes a lock screen button 208, which is a touch or pressure activated button of the touch screen 17. In its default mode, the lock screen button 208 indicates that the touch screen 17 of the touch-screen monitor 15 is unlocked, which means that the touch screen modality of the touch screen is operational and active. In this state, the lock screen button 208 manifests as a button displaying an unlocked padlock icon, for example, as shown in FIG. 6a. However, by pressing and holding the lock screen button 208 for a prescribed period of time (e.g., at least 2 seconds), the touch screen 17 transitions into a "locked" state in which keypad mechanisms are displayed in a "greyed out" mode, and items displayed on such keypad mechanisms may be closed or otherwise unaffected by touching the touch screen 17. When the touch screen 17 has been so locked out, then lock screen button 208 may change its display mode so at to indicate the locked-out state of the touch screen 17, such as, for example, by displaying a locked padlock icon as shown in FIG. 6b. In addition, during the locked-out state, the lock screen button 208 may be surrounded and bordered by a unlock screen key 209. Touching any portion of the unlock screen key 209 of the touch screen 17 immediately unlocks the touch screen, which transitions back to the unlocked state in which the touch screen is once fully again operational and active. The touch screen 17 also automatically unlocks and/or remains unlocked in the presence of any technical, high-priority, medium-priority, or low-priority alarm. The touch screen 17 may also automatically transition to the locked out state following a period of no touch activity and as long as no alarm is present in accordance with an auto-lock feature.

In accordance with an embodiment of this disclosure, the header portion 102 may include a connectivity status indicator 210, which when lit or glowing, possibly in a color such as green or some other suitable color, indicates network connectivity status with respect to the system touch-screen monitor 15 and a Hospital Information System/Computer Information System (HIS/CIS) network. When the connectivity status indicator 210 is not lit or glowing, or is lit or glowing in a different color such as red, then the absence of network connectivity with an HIS/CIS network is indicated.

Figure 3A:
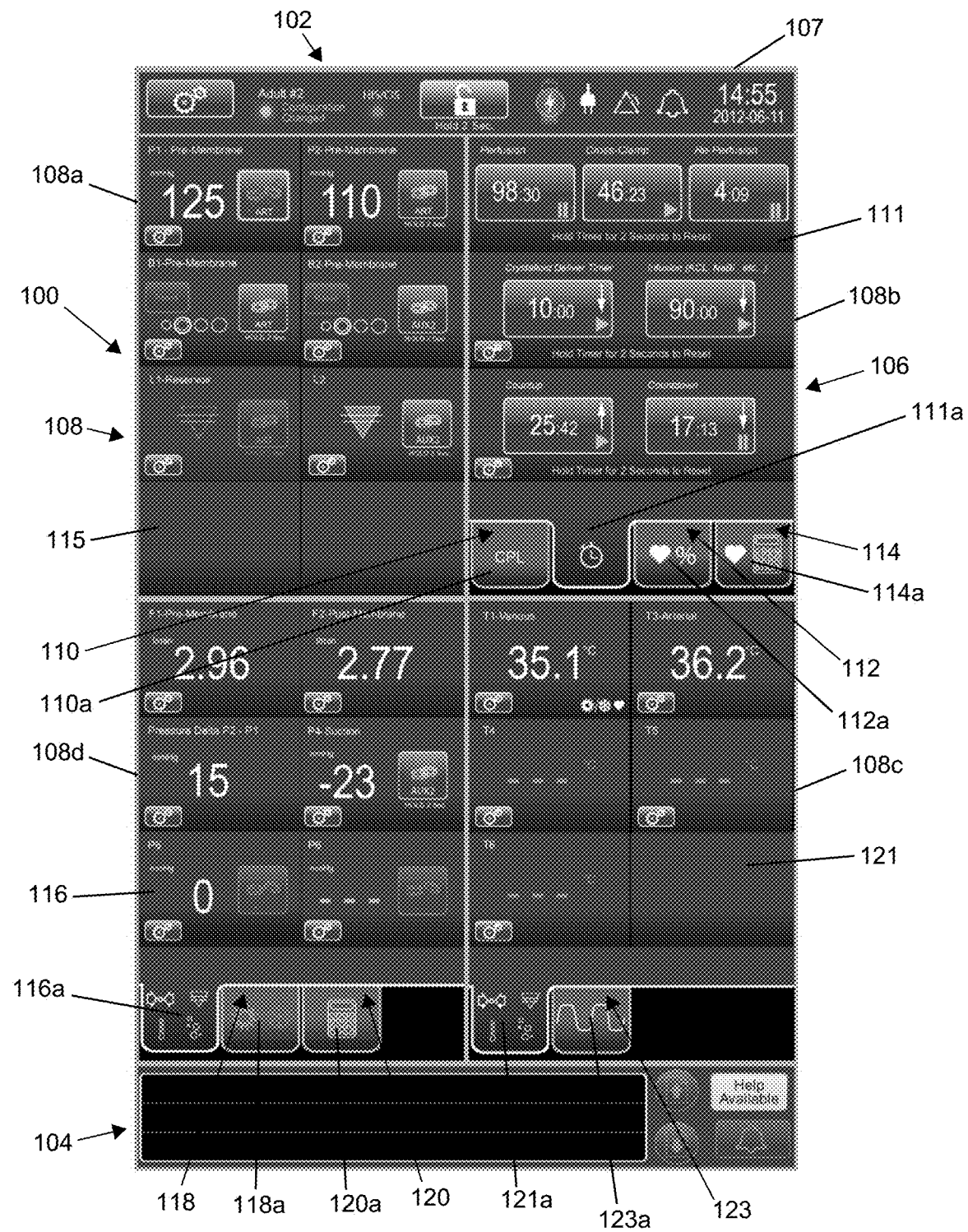
FIGS. 3a and 3b (which may be collectively referred to as "FIG. 3") illustrate an exemplary, non-limiting configuration of a graphical user interface of a touch screen monitor in accordance with an embodiment of this disclosure.
Figure 3B:
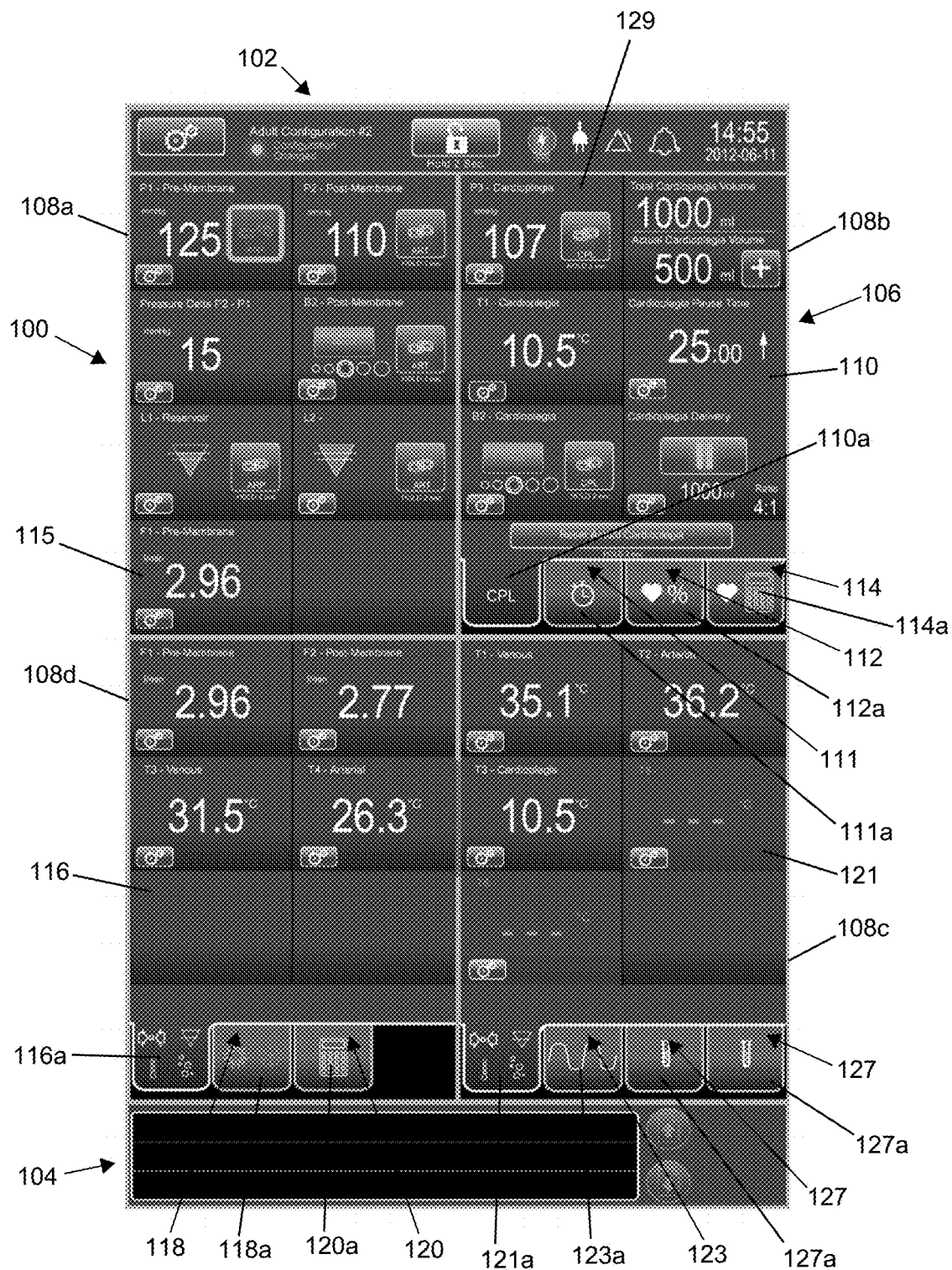

In accordance with an embodiment of this disclosure the header portion 102 may include a configuration indicator 212, which indicates a particular user configuration of the graphical user interface 100 that has been configured and/or selected by a user of the touch-screen monitor 15 in accordance with the user's preferences. For example, the touch-screen monitor 15 may be operated to provide multiple different touch screen configurations that are selectable by a user depending upon user preference and depending upon programmed graphical user interface options. For example, the touch-screen monitor 15 may be operated to provide two, or three, or four, or five, or six, and so on, different selectable touch screen configurations that are selectable by the user. FIG. 3a, for example, constitutes one non-limiting selectable touch screen configuration. Other non-limiting selectable touch screen configurations, such as shown by FIG. 3b, for example, may be selectively arranged by a user of the graphical user interface 100 during a set-up mode that is described later in this disclosure.

Figure 7A:
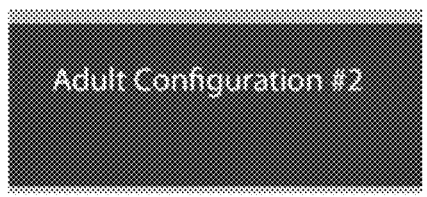
FIGS. 7a and 7b (which may be collectively referred to as "FIG. 7") illustrate various displays for a user configuration indicator of the graphical user interface in accordance with an embodiment of this disclosure.
Figure 7B:

FIG. 7a indicates that a second user configuration, identified as "Adult Configuration #2," has been selected and is displayed as the configuration indicator 212. As should be appreciated, there is a first user configuration, identified as "Adult Configuration #1," which may be selected but has not been selected in accordance with the non-limiting example. If it were selected, then the configuration indicator 212 would display "Adult Configuration #1." By extrapolation, other user configurations such as a third user configuration would be identified as "Adult Configuration #3" when selected, and so on. If the second user configuration is modified after selection, which is possible in accordance with this disclosure, then the configuration indicator 212 indicates that a modification has been made by an indicator that is lit or glowing, possibly in a yellow color or other color, accompanied by the phrase "Configuration Changed" as illustrated by FIG. 7b, for example.

Figure 8A:
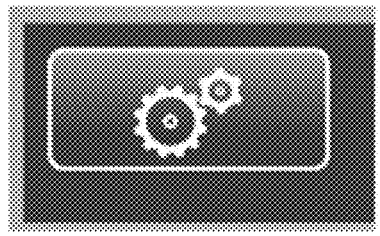
FIGS. 8a and 8b (which may be collectively referred to as "FIG. 8") illustrate a display for a system settings menu button, as shown by the icon of FIG. 8a in a first operational mode and as shown by the icon of FIG. 8b in a second operational mode, in accordance with an embodiment of this disclosure.
Figure 8B:
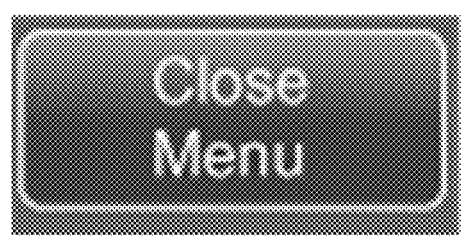

In accordance with an embodiment of this disclosure, the header portion 102 may include a system settings menu button 214, which is used to activate a system configuration menu interface 802. In accordance with this embodiment, the system settings menu button 214 may be represented by an icon as shown in FIG. 8a. The system configuration menu interface is used to configure the graphical user interface 100 of the cardio-pulmonary bypass machine 1 so that it is configured ergonomically per the preferences of one or more particular users. The system configuration menu interface 802 will be described later in this disclosure. When the system configuration menu interface is displayed upon activation of the system settings menu button 214, which may constitute a touch or pressure activatable single activation button, the icon shown in FIG. 8a is replaced by the "Close Menu" button illustrated by FIG. 8b.

In accordance with an embodiment of this disclosure, the header portion 102 may be provided with all of the features 200, 202, 204, 206, 208, 210, 212 and 214 described above, or with just some of the features 200, 202, 204, 206, 208, 210 and 214 in any combination.

Central Monitoring Portion of the Graphical User Interface

The central monitoring portion 106 is divided into one or more sections 108, which are used to display information pertaining to one or more sensor modules and/or to provide one or more functionalities (i.e., user modules) useful in operating, or facilitating the operation, of cardio-pulmonary bypass machine 1. For application to a heart-lung machine environment, or other cardio-pulmonary bypass machine, dividing the central monitoring portion 106 into four sections 108, which may be referred to as "quadrants," provides optimal efficient use of space and provides an ergonomic user-centric and configurable monitoring interface. However, for other applications, other numbers of sections 108 may be preferred. For example, the central monitoring portion may be divided into two sections, or three sections, or five sections, or six sections, or seven sections, or eight sections. Each of the sections of the central monitoring portion may be substantially symmetrical (i.e., have the same size and shape) or they may be asymmetrical (i.e., some sections may have a different size and/or shape as other sections).

Each of the sections 108 may be individually configurable to include from one to four user configurable tabbed display pages, or each of the sections 108 may constitute a single untabbed display page, which is user configurable. In accordance with some embodiments of this disclosure, some of the sections 108 include one to four user configurable tabbed display pages and some of the sections 108 constitute a single untabbed display page. In accordance with an embodiment of this disclosure, the central monitoring portion 106 is provided with one untabbed display page for section 108a and three sections 108b, 108c and 108d including a plurality of tabbed display pages.

A display page, in accordance with this disclosure, is a graphical image displayed within the boundaries of the section 108 in which it is confined. A display page, when on display, either completely covers its section or covers a substantial majority of the display space of its section 108. A display page, in accordance with this disclosure, is not a pop-up image, and it does not overlap more than one section 108. Hence, a display page in accordance with this disclosure remains within the confines of the borders 107 of its section 108 and does not encroach upon any of its neighboring display pages located in another section 108. Limiting a display page in this way has the advantage that display pages from neighboring sections cannot overlap one another so they cannot cover or obscure images, including data and alarms, displayed by a display page of another section. A display page, in accordance with this disclosure, is constructed as either an untabbed display page or as a tabbed display page.

Untabbed Display Pages

Figure 9:
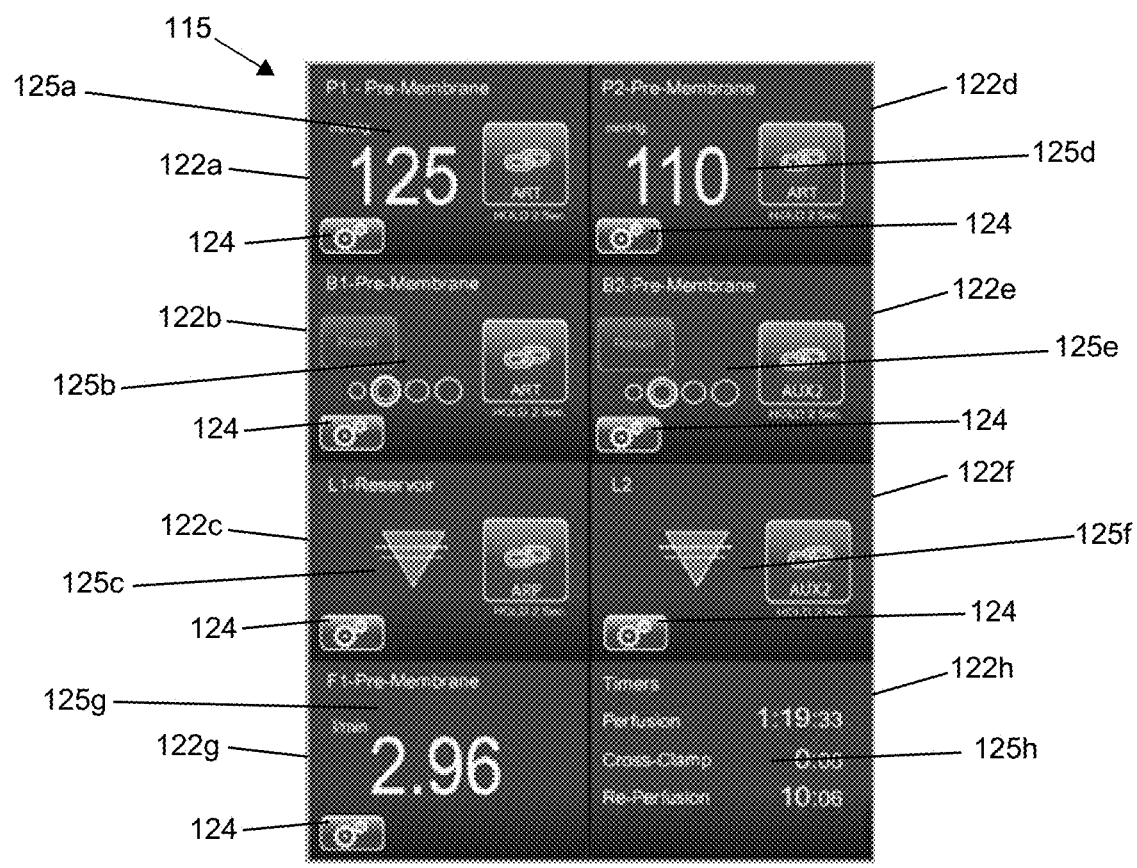
FIG. 9 illustrates an exemplary, non-limiting configuration of an untabbed display page of a central monitoring portion of a graphical user interface in accordance with an embodiment of this disclosure.

An untabbed display page, such as display page 115 of section 108a, has no tabs. An untabbed display page 115 may include one or more sectors 122a, 122b, 122c, 122d, 122e, 122g, 122f and 122h, such as shown by FIG. 9. In accordance with a non-limiting embodiment of this disclosure, the untabbed display page 115 is configured as a sensor module display page that displays primarily sensor data and optionally other information pertinent to the operation of the cardio-pulmonary bypass machine 1. In accordance with an embodiment of this disclosure, the untabbed display page 115 displays time-sensitive information critical to the operation of the cardio-pulmonary bypass machine 1 in a manner that requires the information to be continuously displayed so as to be continuously monitorable by those who operate the cardio-pulmonary bypass machine 1, such as a perfusionist. In this way, a person monitoring the graphical user interface 100 may have constant direct visual access to the information displayed by the untabbed display page 115.

As evident from FIG. 9, those sectors of the untabbed display page 115 that are configured to display sensor data include their own module settings menu button 124. Each module settings menu button 124 is similar to the system settings menu button 214, except that each module settings menu button 124 is used to activate a module configuration menu interface. In accordance with an embodiment of this disclosure, the module settings menu button 124 may be represented by an icon as shown in FIG. 8a. The module configuration menu interface is used to configure the corresponding module for a sector of the graphical user interface 100 so that it is configured to display sensor data per the preferences of a user who sets up the functionality of the module and who links the appropriate sensor to the sector via a sensor module, which is provided with an informational display. Various non-limiting informational displays 125a, 125b, 125c, 125d, 125f and 125g are illustrated in FIG. 9 for their corresponding sensor modules in their corresponding sectors. The configurations of various specific sensor module types are described in greater detail later in this disclosure.

Various module configuration menu interfaces will be described later in this disclosure in greater detail. When the module configuration menu interface is displayed upon activation of the module settings menu button 124, which may constitute a touch or pressure sensitive single activation button, the module configuration menu interface remains displayed in its quadrant until closed by activating a pressure or touch sensitive button designated for closing the module configuration menu interface. In an embodiment of this disclosure, when a module configuration menu interface is displayed it covers the entire quadrant in which the module is located, but does not cover any portion of any other quadrant of the graphical user interface 100.

As evident from FIG. 3, not every sector of an untabbed display page needs to be utilized in accordance with an embodiment of this disclosure. As evident from FIG. 9, in accordance with an embodiment of this disclosure, each sector of an untabbed display page may be selectively utilized, although some of the sectors may be configured for use with a sensor module and some of the sectors may be configured for use with a non-sensor module. In FIG. 9, for example, sector 122h is configured to display non-sensor data provided by a non-sensor module that is provided with an informational display 125h.

Tabbed Display Pages

A tabbed display page, such as tabbed display pages 110, 111, 112, 114, for example, of section 108b of FIG. 3 are characterized as tabbed because they each include a tab 110a, 111a, 112a, 114a, respectively, extending from a portion of the display page. In accordance with an embodiment of this disclosure, each tab 110a, 111a, 112a, 114a extends from a bottom portion of its display page 110, 111, 112, 114, respectively. However, in accordance with other embodiments, the tabs may all extend from the right side of the display pages, or they may all extend from the left side of the display pages, or they may all extend laterally towards the sides of the touch-screen monitor 15, or they may all extend towards the interior of the touch screen 17, or they all may extend from the top of the display pages.

The tabs 110a, 111a, 112a, 114a serve multiple functions. First, the tabs allow a user to see how many display pages a section 108 has. For example, in FIG. 3a, four sections 108 are shown in the non-limiting illustrative embodiment. Going clockwise, the four sections 108 include an upper left section 108a and an upper right section 108b, which each border the header portion 102, and a lower right section 108c and a lower left section 108d, which each border the footer portion 104. The upper right section 108b includes four tabbed display pages 110, 111, 112 and 114 with corresponding respective tabs 110a, 111a, 112a and 114a. The lower left section 108d includes three tabbed display pages 116, 118 and 120, and their corresponding tabs are tabs 116a, 118a and 120a, respectively. The lower right section 108c includes two tabbed display pages 121 and 123, respectively, and their corresponding tabs are tabs 121a and 123a. The upper left section displays a single untabbed display page 115 because the display page has no tabs.

Second, each tab provides one or more graphical display icons that display information regarding the nature of the display page corresponding to the displayed icon. For example, according to a non-limiting embodiment of this disclosure, tab 110a displays the abbreviation "CPL" identifying tabbed display page 110 as displaying modules monitoring data particularly related to cardioplegia, which pertains to an intentional and temporary cessation of cardiac activity of a patient on cardiopulmonary bypass during cardiac surgery. Thus, tab 110a may be referred to as a cardioplegia tab and tabbed display page 110 may be referred to as a cardioplegia display page.

Tab 111a displays a clock icon identifying tabbed display page 111 as displaying timer data. Thus, tab 111a may be referred to as a timer tab and tabbed display page 111 may be referred to as a timer display page.

Tab 112a displays a heart percentage icon identifying tabbed display page 112 as directed to a weight based target flow calculator, such as may be used to calculate out a target blood flow for a patient on cardiopulmonary bypass based on the patient's height, weight, and body surface area (BSA) calculated using one of the known BSA formulas by either DuBois, Boyd or Mosteller. Thus, tab 112a may be referred to as a target flow calculator tab and tabbed display page 112 may be referred to as a target flow calculator display page.

Tab 114a displays a BSA calculator icon identifying tabbed display page 114 as directed to a perfusion calculator, such as may be used to calculate various perfusion parameters prior to, and during, a cardiopulmonary bypass procedure. An example of a perfusion calculator, such as may be implemented by the embedded processor 30, is disclosed by U.S. Provisional Patent Application No. 62/160,689, filed on May 13, 2015, and its corresponding U.S. Patent Application Publication No. US XXXX/YYYYYYYY, both of which are incorporated herein by reference in their entirety for all they disclose. Tab 114a may be referred to as a perfusion calculator tab and tabbed display page 114 may be referred to as a perfusion calculator page.

Tabs 116a and 121a display a plurality of icons, such as are directed to pressure measurement, temperature measurement, bubble detection, and reservoir fluid level measurement, thereby identifying the respective tabbed display pages 116 and 121 as directed to displaying data from selected sensor modules pertaining to one or more types of sensors directed to pressure measurement, temperature measurement, bubble detection, and fluid level measurement for various portions of the extracorporeal blood flow circuit of the cardio-pulmonary bypass machine 1. Thus, tabs 116a and 121a may be referred to as sensor tabs and tabbed display pages 116 and 121 may be referred to as sensor data display pages.

Tab 118a displays a sun and snowflake icon identifying tabbed display page 118 as directed to remote monitoring and control of a separate heater-cooler unit 85 that is associated with the cardio-pulmonary bypass machine 1. The heater-cooler unit 85 is provided to help monitor and control a patient's temperature during cardiopulmonary bypass, and may be operably connected to provide patient temperature data to the processor 30 and to receive control signals from the processor 30. Thus, tab 118a may be referred to as a heater/cooler remote control tab and tabbed display page 118 may be referred to as a heater/cooler remote control page.

Tab 120a displays a calculator icon identifying tabbed display page 120 as directed to a basic calculator, such as may be used to perform basic mathematical operations (e.g., addition, subtraction, multiplication, division). Thus, tab 120a may be referred to as a calculator tab and tabbed display page 120 may be referred to as a calculator display page.

Tab 123a displays a pulsatile wave icon identifying tabbed display page 123 as directed to a pulsatile flow control module that is enabled when the cardiopulmonary bypass machine 1 employs an optional arterial pump capable of generating pulsatile flow in at least a portion of the extracorporeal blood flow circuit. Thus, tab 123a may be referred to as a pulsatile flow tab and tabbed display page 123 may be referred to as a pulsatile flow control display page.

FIG. 3b illustrates a different configuration for the graphical user interface 100 than in FIG. 3a. It should be appreciated that these two configurations represent just two possible configurations from a multitude of configurations available to a user of the graphical user interface 100. Each configuration may be selectably configured by the user of the graphical user interface 100 using set up functionalities available to enable the user to customize the graphical user interface 100 to the user's personal liking.

FIG. 3b illustrates two additional tabs 127a provided with another unique icon that represents the functionality of the corresponding tabbed display pages 127. In this case, the tabbed display page 127 constitutes a blood monitoring unit (BMU) interface display page and its tab 127a constitutes a BMU interface tab. As should be appreciated, other icons may be used to represent the functionalities of corresponding tabbed display pages. In other words, the scope of this disclosure should not be construed as limited to the particular icons and tabbed display pages explicitly disclosed herein.

Each tab performs a selection function when a user touches or presses the tab on the touch screen 17 of the touch-screen monitor 15. This feature is evident by comparing FIGS. 3a and 3b. In FIG. 3a, the displayed tabbed display page of section 108b is tabbed display page 111, which is the case because at some time previous the user had to press the tab 111a on the touch screen 17. Pressing tab 111a on the touch screen 17 results in the processor 30 causing the touch-screen monitor 15 to display tabbed page 111, which is a timer display page, so it appears foremost in section 108b of the graphical user interface 100. The other tabbed display pages 110, 112, 114 are not visible except for their respective tabs 110a, 112a, 114a. This creates a visual effect in which the displayed tabbed display page 111 appears to overlay the tabbed display pages 110, 112 and 114, which are not in view.

For the purposes of this disclosure, when a tabbed display page is displayed foremost in its section, then it may be said to be in a display mode. When a tabbed display page appears to be overlaid by the tabbed display page that is in the display mode, the visually overlaid tabbed display page is said to be in the overlaid mode. Thus, with respect to section 108b of FIG. 3a, the tabbed display page 111 is in the display mode and the tabbed display pages 110, 112 and 114 are in the overlaid mode. In accordance with an embodiment of this disclosure, the plurality of tabbed display pages within a section may default upon initialization to display the leftmost tabbed display page in the display mode and the rest of the tabbed display pages in the overlaid mode.

In FIG. 3b, the displayed tabbed display page of section 108b is tabbed display page 110, which is the case because at some time previous the user had to press the tab 110a on the touch screen 17 or the section 108b just initialized. Pressing tab 110a on the touch screen 17 results in the processor 30 causing the touch-screen monitor 15 to display tabbed page 110, which is a cardioplegia display page, so it appears foremost in section 108b of the graphical user interface 100. The other tabbed display pages 111, 112, 114 are not visible except for their respective tabs 111a, 112a, 114a. This creates a visual effect in which the displayed tabbed display page 110 appears to overlay the display pages 111, 112 and 114, which are not in view. Thus, with respect to section 108b of FIG. 3b, the tabbed display page 110 is in the display mode and the tabbed display pages 111, 112 and 114 are in the overlaid mode.

Although not explicitly shown in the drawings, by extrapolation it should be appreciated that touch or pressure to tab 112a on the touch screen 17 would result in processor 30 causing the touch-screen monitor 15 to display tabbed display page 112, which is the target flow calculator display page, via the graphical user interface 100 so it appears foremost in section 108b (i.e., in the display mode) while the other tabbed display pages 110, 111 and 114 appear overlaid (i.e., in the overlaid mode) and not in view except for their respective tabs 110a, 111a and 114a. Likewise, touch or pressure to tab 114a on the touch screen 17 would result in processor 30 causing the touch-screen monitor 15 to display tabbed display page 114, which is the perfusion calculator page, via the graphical user interface 100 so it appears foremost in section 108b (i.e., in the display mode) while the other tabbed display pages 110, 111 and 112 appear overlaid (i.e., in the overlaid mode) and not in view except for their respective tabs 110a, 111a and 112a.

This tab functionality of the tabs and tabbed display pages with respect to the display mode and the overlaid mode makes it possible for a user to move visually from one tabbed display page to another without having to move through a nested layered page structure. The structure of section 108b, with its tabs that are touch or pressure activatable to transition the corresponding tabbed display page to the display mode while simultaneously transitioning the remaining tabbed display pages to the overlaid mode, may be characterized as a tab selectable page structure, which is substantially different from conventional nested layered page structures such as those disclosed by U.S. Pat. No. 4,712,191, which is incorporated herein by reference in its entirety. As should be appreciated from FIGS. 3a and 3b, the sections 108b, 108c and 108d each possess its own tab selectable page structure.

An advantage of a tab selectable page structure is that a user can move directly from any one of the tabbed display pages within the section to any other one of the tabbed display pages within the same section with a single touch or push on the appropriate tab. For example, a user could move from tabbed display page 111 directly to tabbed display page 110 by activating tab 110a, or directly from tabbed display page 111 to tabbed display page 112 by activating tab 112a, or directly from tabbed display page 111 to tabbed display page 114 by activating tab 114a. Thus, a tab selectable page structure permits flexibility of movement from one tabbed display page to another tabbed display page that is not possible with nested page structures. For example, a user may move from tabbed display page 112 to tabbed display page 110 and then to tabbed display page 114 by first activating tab 110a, and after tabbed display page 110 is in the display mode then activating tab 114a. This example illustrating the flexibility of movement between tabbed display pages is non-limiting and for illustration purposes only, as any permutation of sequential movement between tabbed display pages within a section is within the scope of this disclosure.

Another advantage of a tab selectable page structure is that the tabs may be used to alert the user to the alarm status of various modules that may be configured as part of each tabbed display page. For example, in accordance with an embodiment of this disclosure, whenever a tabbed display page is in the overlaid mode and any sensor module or any non-sensor module that is a component of the overlaid tabbed display page transitions to an alarm state, then the corresponding tab of the overlaid tabbed display page may transition to an alarm mode and flash, or blink, and possibly change color, in order to bring the alarm state to the user's attention. In this way, the user would be placed on notice by the alarming tab to check the overlaid tabbed display page for its alarming module. In accordance with an embodiment of this disclosure, the alarm mode includes flashing between a normal color to an alarm color at a specified rate per a medical device standard.

As a non-limiting example, section 108b of FIG. 3b includes a pressure sensor module 129, which is displayed while tabbed display page 110 is in the display mode, and tabbed display pages 111, 112 and 114 are in the overlaid mode. In FIG. 3a, tabbed display page 110 of section 108b is in the overlaid mode and tabbed display page 111 is in the display mode. When in this state, the user would not be able to see directly alarms incorporated as part of the pressure sensor module 129 when they alarm, such as are described later in this disclosure. Such alarms may be triggered when measured pressure in a portion of the extracorporeal blood flow circuit exceeds a maximum threshold measured pressure or falls below a minimum threshold measured pressure.

Tab 110a may provide a notice of the alarming pressure sensor module 129 because tab 110a is still visible even though tabbed display page 110 is in the overlaid mode in FIG. 3a. In accordance with an embodiment of this disclosure, when the pressure sensor module 129 should be alarming and the tabbed display page 110 is in the overlaid mode, the processor 30 transitions tab 110a to an alarm mode in which tab 110a may flash and change color. In accordance with an embodiment of this disclosure, the alarm mode for each tab involves flashing between its background color and an appropriate alarm color, such as yellow for medium priority alarms, and red for high priority alarms.

Based on how the tab flashes, and/or changes color, the alarming tab may inform the user regarding the nature of the alarm, such as whether it constitutes a high priority alarm, a medium priority alarm, or a low priority alarm. For example, in accordance with an embodiment of this disclosure, a tab that flashes yellow may indicate a medium priority alarm and a tab that flashes red may indicate a high priority alarm. In accordance with an embodiment of this disclosure, low priority alarms constitute a color change from the tab's background color to cyan or to yellow without additional flashing. Thus, for example, a tab that transitions from its background color to a steady cyan color or a steady yellow color is indicating a low priority alarm state. On the other hand, a tab that begins flashing yellow indicates a medium priority alarm state and a tab that begins flashing red indicates a high priority alarm state. The rate of flash may also correspond to the degree of priority of the alarm. For example, the rate of flashing yellow in accordance with a medium priority alarm may be slower than the rate of flashing red in accordance with a high priority alarm. Low priority alarms, however, whether cyan or yellow in color, maintain a steady, non-flashing display of the alarm color.

Thus, in an embodiment of this disclosure, an alarming tab may transition to a colored state indicative of the severity of the alarming module of the overlaid tabbed display page. For example, an alarming tab may transition to possess a red color throughout, or to possess a red color on only a portion of the tab, in order to give notice of a high priority alarm, while the alarming tab may transition to possess a yellow color throughout, or to possess a yellow color on only a portion of the tab, in order to give notice of a medium or low priority alarm. An alarming tab may also transition to possess a cyan color throughout, or to possess a cyan color on only a portion of the tab, in order to give notice of a low priority alarm. The alarm color scheme employed for this disclosure is in compliance with standard color schemes for medical devices. Other color schemes may be employed when the graphical user interface 100 is employed for use only with non-medical devices.

Thus, each tab in accordance with this disclosure that is associated with a tabbed display page capable of displaying an alarm is capable of transitioning to an alarm mode when the associated tabbed display page is in the overlaid mode and some module of the overlaid tabbed display page should be alarming. While the alarm functionality of tab 110a has been described in detail, this alarm functionality is possessed by each of the other tabs 111a, 116a, 118a and 121a, for example, whose associated tabbed display pages possess a sensor module or non-sensor module having an alarm state that needs attending to by a user.

Having described the general structure of the graphical user interface 100, namely, the untabbed display page(s) and the tab selectable page structure of the tabbed display pages, various sensor modules and non-sensor modules that may be employed as component modules of either the untabbed display page(s) and/or the tabbed display pages are described as follows.

Pressure Sensor Modules

Figure 10A:
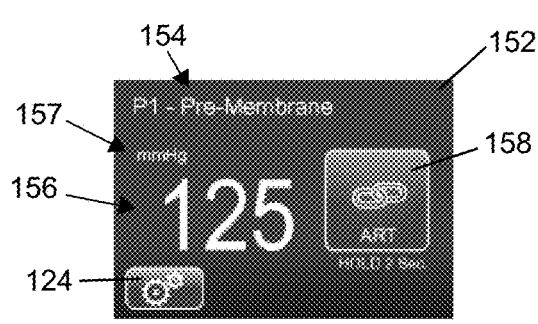
Figure 10B:
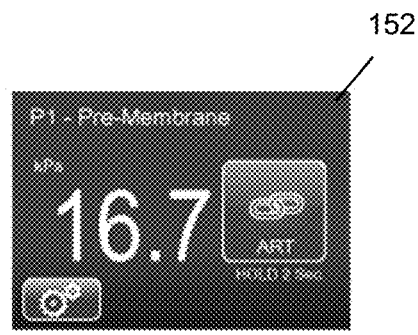

The cardiopulmonary bypass system 1 is typically provided with one or more pressure sensors 50 disposed to measure pressure at various desired points on the extracorporeal blood flow circuit 3, and to input pressure data to the processor 30, which may process the pressure data before outputting it to the graphical user interface 100 for display. Data from each pressure sensor 50 is displayed by a corresponding unique pressure sensor module 152, such as shown in FIGS. 10a and 10b. FIG. 10a is similar to FIG. 10b except that FIG. 10a displays pressure data in mmHg and FIG. 10b displays pressure data in kPa. Each pressure sensor module 152 is a display module that may be displayed in any of the four quadrants 108, whether as a component of an untabbed display page, or whether as a component of a tabbed sensor display page, or whether as a component of a tabbed Cardioplegia display page, depending on the application and set-up per the user's preferences. As a non-limiting example, pressure sensor modules are illustrated as components of the untabbed display page 115 and as a component of the tabbed Cardioplegia display page 110, as shown in FIG. 3b.

As shown in FIG. 10a, each unique pressure sensor module 152 includes a title field 154, which is an alphanumeric field that displays a unique identifier pertaining to the pressure sensor 50 from which displayed data is obtained. The unique identifier may have the form of "Px –," in which x is a number corresponding to a specific pressure sensor, followed by a sensor name, such as may indicate location along the extracorporeal blood flow circuit. The sensor name shown in FIG. 10a is merely exemplary, for illustration purposes, and is not meant to be limiting.

Each pressure sensor module 152 also includes a pressure value data field 156, which is a numerical field that displays the value of the pressure data measured by the pressure sensor 50, and a pressure value unit field 157, which is an alphanumeric field that displays the units of the pressure data measured by the pressure sensor 50. Each pressure sensor module 152 may further include an intervention button 158 that may link or unlink a pump 38 interaction of the cardiopulmonary bypass machine 1, as described in more detail below. Each pressure sensor module 152 also includes a module settings menu button 124 as discussed above.

Figure 10C:
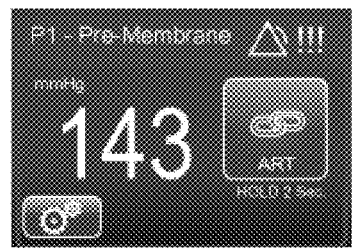

Each pressure sensor module 152 may further include a plurality of alarm indicating states as illustrated by FIGS. 10c, 10d, 10e, 10f and 10g. For example, as shown by FIG. 10c, when the pressure sensor 50 measures pressure in the extracorporeal blood flow circuit that reaches and/or exceeds a stop limit value, then pressure sensor module 152 switches to a pressure high priority alarm state. The pressure high priority alarm state may be configured in a variety of ways. In one non-limiting embodiment, the pressure high priority alarm state involves displaying a warning symbol, such as a triangle, with three exclamation points, and a red banner, which flash at a determined rate (i.e., a flash frequency of 1.4 Hz to 2.8 Hz; and duty cycle of 20% to 60%) in accordance with industry standards for medical devices. In another embodiment of this disclosure, in addition to, or as a replacement to, the visual component of the pressure high priority alarm state disclosed above, the pressure high priority alarm state may include an auditory alarm that comprises sound (e.g., a high pitch beeping) that pulses in a predetermined cadence.

Figure 10D:
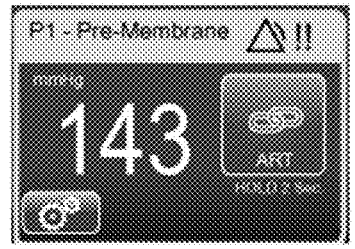

As shown by FIG. 10d, when the pressure sensor 50 measures pressure in the extracorporeal blood flow circuit that reaches and/or exceeds a threshold limit value that is substantially lower than the stop limit value, then the pressure sensor module 152 switches to a pressure medium priority alarm state. The pressure medium priority alarm state may be configured in a variety of ways. In one non-limiting embodiment, the pressure medium priority alarm state involves displaying a warning symbol, such as a triangle, with a two exclamation points, and a yellow banner, which flash at another predetermined rate (i.e., such as a flash frequency of 0.4 Hz to 0.8 Hz, and duty cycle of 20% to 60%). In another embodiment of this disclosure, in addition to, or as a replacement to, the visual component of the pressure medium priority alarm state disclosed above, the pressure medium priority alarm state may include an auditory alarm that comprises sound (e.g., a substantially lower pitch beeping than the high pitch beeping of the high priority alarm state) that pulses in another predetermined cadence.

Figure 10E:
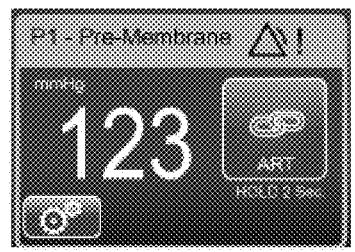

As shown by FIG. 10e, when the pressure sensor 50 measures pressure in the extracorporeal blood flow circuit 3 that reaches and/or exceeds an alarm limit value that is substantially lower than the threshold limit value, then the pressure sensor module 152 switches to a pressure low priority alarm state. The pressure low priority alarm state may be configured in a variety of ways. In one non-limiting embodiment, the pressure low priority alarm state involves displaying a warning symbol, such as a triangle, with a single exclamation point, and a cyan banner, which is presented in a non-flashing manner (i.e., duty cycle is 100%). In another embodiment of this disclosure, in addition to, or as a replacement to, the visual component of the pressure low priority alarm state disclosed above, the pressure low priority alarm state may include an auditory alarm that comprises sound (e.g., a substantially lower pitch beeping than the medium pitch beeping of the pressure medium priority alarm state) that pulses in another predetermined cadence.

Thus, in accordance with the above examples, the pressure value for the stop limit value is greater than the pressure value for the threshold limit value, which is greater than the pressure value for the alarm limit value. In addition, a particular color scheme for high, medium and low priority alarm banners has been described with respect to pressure measurement, namely, red, yellow and cyan, respectively, in accordance with industry standards for medical devices. However, when the graphical user interface 100 is employed in non-medical environments other color schemes may be employed.

In the case when the pressure high priority alarm state has been activated, the pressure measured by the pressure sensor 50 has reached and/or exceeded the stop limit value, which means there is a need to reduce pressure promptly in at least that portion of the extracorporeal blood flow circuit 3 whose pressure is monitored by the pressure sensor 50. One way to effect such a prompt reduction in pressure is to provide an automatic pressure correction algorithm that decreases pump activity to decrease pressure. Once pressure drops below a set threshold, the associated pump automatically resumes activity in accordance with the automatic pressure correction algorithm. However, an intervention button 158 may be provided that, when touch or pressure activated by a user, overrides the automatic pressure correction algorithm that otherwise would have affected operation of a particular blood pump 38.

As a non-limiting example, according to FIG. 10*a*, the intervention button 158 indicates an operable link to a particular pump, namely an arterial pump 38. When pressure exceeds the stop limit value, an automatic pressure correction algorithm is activated so the processor 30 controls operation of arterial pump 38 in a manner to reduce pressure (i.e., the pump 38 is shut off completely or partially to reduce pressure). However, by manual activation of the intervention button 158 by a user, the automatic pressure correction algorithm may be selectively overridden for two seconds.

In the case when no intervention mechanism has been associated with the pump, the intervention button 158 manifests as in FIG. 11*a* so as to indicate no link between the pump and the intervention button 158, such as could override the automatic pressure correction algorithm. When the intervention button 158 is in the state shown by FIG. 11*a*, the user cannot manually override operation of the automatic pressure correction algorithm of pump 38 due to a lack of association between the intervention button 158 and the pump 38. However, when the intervention button 158 manifests as in FIG. 11*b*, then a malfunction or other unintended functional disconnect between the intervention button 158 and the pump 38 is detected, which is preventing the intervention button 158 from overriding operation of the automatic pressure correction algorithm.

Other pressure alarm states that may be manifested by the pressure sensor module 152 include the states illustrated in FIGS. 10*f*, 10*g* and 10*h*. In FIG. 10*f*, the pressure sensor module 152 is indicating the state in which the pressure sensor 50 is disconnected from the processor 30, such as may occur when the pressure sensor 50 disconnects from the sensor panel. In FIG. 10*g*, the pressure sensor module 152 is indicating the state in which the pressure sensor 50 is malfunctioning. In FIG. 10*h*, the pressure sensor module 152 is indicating the state in which the pressure sensor 50 is unavailable, such as when the pressure sensor 50 is in an "off" configuration.

Bubble Detection Sensor Modules

The cardiopulmonary bypass system 1 is typically provided with one or more bubble sensors 60 disposed to detect bubbles in the blood flow at various desired points on the extracorporeal blood flow circuit 3, and to input bubble detection data to the processor 30, which may process the bubble detection data before outputting it to the graphical user interface 100 for display. Data from each bubble detection sensor 60 is displayed by a corresponding unique bubble detection sensor module 162, such as shown in FIG. 12. Each bubble detection sensor module 162 is a display module that may be displayed in any of the four quadrants 108, whether as a component of an untabbed display page, or whether as a component of a tabbed sensor display page, or whether as a component of a tabbed Cardioplegia display page, depending on the application and set-up per the user's preferences. As a non-limiting example, bubble detection sensor modules are illustrated as a component of the untabbed display page 115 and as a component of the tabbed Cardioplegia display page 110, as shown in FIG. 3*b*.

As shown in FIG. 12, each unique bubble detection sensor module 162 includes a title field 164, which is an alphanumeric field that displays a unique identifier pertaining to the bubble detection sensor 60 from which displayed data is obtained. The unique identifier may have the form of "Bx –," in which x is a number corresponding to a specific bubble detection sensor, followed by a sensor name, such as may indicate location along the extracorporeal blood flow circuit. The sensor name shown in FIG. 12 is merely exemplary, for illustration purposes, and is not meant to be limiting.

Each bubble detection sensor module 162 also includes a bubble detection data field 166, which is a graphical field that displays via a bubble level icon bubble detection data obtained by the bubble detection sensor 60, and a reset button 167 that may be activated by touch or pressure when the bubble detection module 162 is in a state of bubble detection high priority alarm in order to reset the size of the bubbles detected. When the bubble detection module 162 is in a state of high priority alarm, thereby indicating detection of bubbles exceeding a predetermined threshold, there is a need to reduce the flow of blood fluid in the extracorporeal blood flow circuit 3 and remove the bubbles before they enter the patient. Thus, a perfusionist or other operator of the cardiopulmonary bypass machine 1 must ensure corrective action has been taken to remove detected bubbles, as appropriate, upon the bubble detection sensor module 162 entering the bubble detection high priority alarm state.

There is a need, then, for the bubble detection high priority alarm state to persist until corrective action to remove large detected bubbles has been taken. Consequently, the reset button 167 is unavailable for selection when the bubble detection module 162 is not in a state of bubble detection high priority alarm. Once the bubble detection sensor module 162 has entered a bubble detection high priority alarm state, the reset button 167 becomes available for selection. However, touch or pressure activation of the reset button 167 will not reset the alarm status of the bubble detection sensor module 162 while the sensor 60 is detecting bubbles that are larger than the bubble size threshold corresponding to the bubble detection high priority alarm state.

In the case where the bubble detection high priority alarm state is activated, there is a need to remove the detected bubbles from the extracorporeal blood flow circuit 3. One way to initiate removal of these large bubbles is to provide an automatic bubble removal algorithm that decreases blood flow through the extracorporeal blood flow circuit 3 by altering pump activity of the cardiopulmonary bypass machine 1. Each bubble detection sensor module 162 may further include an intervention button 168 that may, when touch or pressure activated by a user, override the automatic bubble removal algorithm that otherwise would have affected operation of one or more blood pumps. Activation of the intervention button 168 initiates a two second override of the automatic bubble removal algorithm, as addressed in more detail below. Each bubble detection sensor module 162 also includes a module settings menu button 124 as discussed above.

The bubble level icon(s) of the bubble detection data field 166 are described with reference to FIGS. 13a, 13b, 13c and 13d. The bubble level icons are able to display multiple levels of predetermined detectable bubble sizes. The user selected bubble detection size is shown as a ring around the selected bubble size, such as shown by the white ring shown in the figures. While the illustrated embodiment employs a white ring, other colors for the ring may be employed so long as they are readily appreciated by a user of the bubble detection sensor module 62. As evident from FIG. 13b, each circle of the bubble level icons is filled in, starting at the leftmost circle and ending before the circle that represents the selected bubble detection size (i.e., the circle surrounded by the white circle), with a color representing a bubble detection medium priority alarm state so as to indicate detection of bubbles that are smaller than those selected to trigger a higher priority alarm (i.e., detection of microbubble activity). In this case, the bubble detection medium priority alarm color may be yellow, as it is with the pressure medium priority alarm state.

When the current bubble detection activity is greater than or equal to the selected bubble detection size, such as shown by FIG. 13c, the bubble level icons are filled in from the smallest detected bubble size to the largest detected bubble size with a bubble detection high priority alarm color, such as red as employed for the pressure high priority alarm state. The color for the high priority alarms is selected in accordance with industry standards for medical devices. The selection of other colors besides red to indicate a high priority alarm pertain to embodiments directed solely to non-medical device applications.

FIG. 13d illustrates the case in which the bubble detection sensor module 162 is configured to be on; however, there is no bubble detection sensor 60 operably attached to the bubble detection sensor module 162. In this case, all of the bubble size indicators of the bubble detection icon are filled with black instead of the background color of the bubble detection sensor module 162. As is the case with all color selections of this disclosure, another color besides black may be used to indicate the absence of a bubble detection sensor 60 operably connected to the bubble detection sensor module 162 when the applied environment pertains solely to non-medical devices.

Figure 14A:
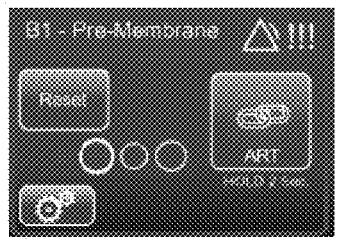
FIGS. 14a, 14b, 14c, 14d and 14e (which may be collectively referred to as "FIG. 14") illustrate various alarm indicating states of a bubble detection sensor module in accordance with an embodiment of this disclosure.

Each bubble detection sensor module 162 may further include a plurality of alarm indicating states as illustrated by FIGS. 14a, 14b, 14c, 14d and 14e. For example, as shown by FIG. 14a, when the bubble detection sensor 60 detects bubbles in the extracorporeal blood flow circuit that reach and/or exceed a selected bubble detection size value, then bubble detection sensor module 162 switches to a bubble detection high priority alarm state. The bubble detection high priority alarm state may be configured in a variety of ways. In one non-limiting embodiment, the bubble detection high priority alarm state involves displaying a warning symbol, such as a triangle, with three exclamation points, and a red banner, which flashes at a predetermined rate (i.e., a flash frequency of 1.4 Hz to 2.8 Hz; and duty cycle of 20% to 60%) in accordance with industry standards for medical devices. In addition, the selected bubble size indicated by the bubble detection size indicators corresponding to the maximum bubble size detected and smaller bubble size indicators are filled with red color as well. In another embodiment of this disclosure, in addition to the visual component of the bubble detection high priority alarm state disclosed above, the bubble detection high priority alarm state may include an auditory alarm that comprises sound (e.g., a high pitch beeping) that pulses in a predetermined cadence in accordance with industry standards for medical devices.

Figure 14B:
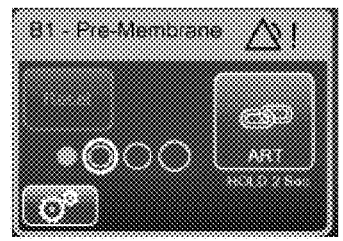

As shown by FIG. 14b, when the bubble detection sensor 60 detects bubbles in the extracorporeal blood flow circuit 3 that are smaller than a threshold limit value (i.e., detection of microbubbles that are smaller than the selected bubble detection size threshold), then the bubble detection sensor module 162 switches to a bubble detection medium priority alarm state. The bubble detection medium priority alarm state may be configured in a variety of ways. In one non-limiting embodiment, the bubble detection medium priority alarm state involves displaying a warning symbol, such as a triangle, with a single exclamation point, and a yellow banner, which may flash at another predetermined rate (i.e., at a rate substantially lower than the flash rate of the bubble detection high priority alarm state, and selected from a flash frequency of 0.4 Hz to 0.8 Hz, and duty cycle of 20% to 60%, in accordance with industry standards for medical devices). In another embodiment of this disclosure, in addition to the visual component of the bubble detection medium priority alarm state disclosed above, the bubble detection medium priority alarm state may include an auditory alarm that comprises sound (e.g., a substantially lower pitch beeping than the high pitch beeping of the bubble detection high priority alarm state) that pulses in a predetermined cadence.

A particular color scheme for high and medium priority alarm banners has been described for bubble detection, namely, red and yellow, respectively, in accordance with industry standards for medical devices. However, when the graphical user interface 100 is employed in a non-medical environment, other color schemes may be employed.

Once the bubble detection sensor module 162 has entered into the bubble detection high priority alarm state, the bubble detection sensor module 162 will remain in this state until the reset button 167 has been activated (i.e., pressed or touch activated) and the bubble detection sensor 60 no longer detects a bubble equal to, or larger than, the bubble size detection limit set for the bubble detection sensor module 162. In other words, once the bubble detection sensor module 162 has entered into the bubble detection high priority alarm state, it will not transition back to a no alarm state or to a bubble detection medium priority alarm state until after the bubble detection sensor module 162 has been reset using the reset button 167 (and simultaneously the bubble detection sensor 60 is not currently detecting a bubble sized at or above the bubble size detection threshold for setting of the high priority alarm).

When the bubble detection sensor module 162 enters the bubble detection medium priority alarm state, the bubble detection sensor module 162 may transition out of this state without requiring activation of the reset button 167. In fact, the reset button 167 is only activatable while the bubble detection sensor module 162 is in the bubble detection high priority alarm state, but it is not activatable while the bubble detection sensor module 162 is in the bubble detection medium priority alarm state. According to an embodiment of this disclosure, the bubble detection sensor module 162 may spontaneously transition from the bubble detection medium priority alarm state to either the no bubble detection state, such as shown in FIG. 12, or to the bubble detection high priority alarm state, such as shown in FIG. 14a, depending upon whether the bubbles decrease in size to below a detectable limit (i.e., no detectable bubbles at all) or increase in size to trigger transition to the bubble detection high priority alarm state.

In the case when the bubble detection high priority alarm state has been activated, one or more bubbles detected by the bubble detection sensor 60 have reached and/or exceeded the selected threshold bubble detection size, which means there is a need to promptly stop the flow of blood in at least that portion of the extracorporeal blood flow circuit in which unacceptably large bubbles have been detected by the bubble detection sensor 60. One way to effect such a prompt cessation in blood flow is to provide the system with an automatic bubble correction algorithm that automatically adjusts one or more pumps of the cardiopulmonary bypass machine in response to the bubble detection high priority alarm state so as to decrease or cease forward blood fluid flow in at least a relevant portion of the extracorporeal blood flow circuit 3. In this way, the system may respond automatically to the bubble detection high priority state and, therefore, facilitate the process performed by a perfusionist or other health care provider directed to clearing unacceptably large bubbles detected in the extracorporeal blood flow circuit 3.

The bubble detection sensor module 162 may be provided with an intervention button 168 that, when activated by a user by touch or pressure, overrides the automatic bubble correction algorithm so that it ceases to affect operation of a particular pump 38 for a predetermined period of time, such as two seconds. As a non-limiting example, according to FIG. 14*a*, the intervention button 168 indicates an operable link to a particular pump, namely an arterial pump 38. When bubbles are detected exceeding in size the bubble detection threshold limit, the automatic bubble correction algorithm is activated so the processor 30 controls operation of the arterial pump 38 in a manner to reduce or cease forward blood flow in at least the relevant portion of the extracorporeal blood fluid circuit 3. However, by manual activation of the intervention button 168 by a user, the automatic bubble correction algorithm is selectively overrided for two seconds.

Figure 14C:
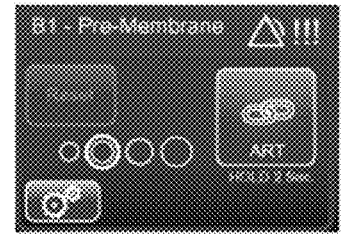

The bubble detection sensor module 162 is capable of transitioning to several additional alarm states. For example, as shown in FIG. 14*c*, in the case when the bubble detection sensor 60 becomes disconnected from the sensor panel, the bubble detection sensor module 62 transitions to a bubble detection disconnect high priority alarm state. The bubble detection disconnect high priority alarm state may be configured in a variety of ways. In one non-limiting embodiment, the bubble detection disconnect high priority alarm state involves displaying a warning symbol, such as a triangle, with three exclamation points, and a red banner, which flashes at a predetermined rate. However, unlike the bubble detection high priority alarm state, while in the bubble detection disconnect high priority alarm state, none of the bubble size indicators of the bubble detection data field 166 are filled with red color, but they are filled with a black color to indicate the disconnect. In another embodiment of this disclosure, in addition to the visual component of the bubble detection disconnect high priority alarm state described above, the bubble detection disconnect high priority alarm state may include an auditory alarm that comprises sound (e.g., a high pitch beeping) that pulses in a predetermined cadence.

Figure 14D:
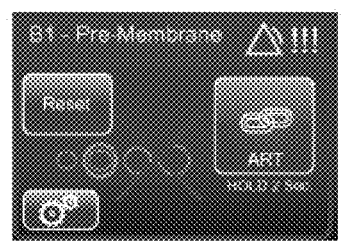

As shown in FIG. 14*d*, when the bubble detection sensor 60 is enabled but malfunctioning in some way, so as to return a fault status, the bubble detection sensor module 162 transitions to a bubble sensor fault alarm state. The bubble sensor fault alarm state may be configured in a variety of ways. In one non-limiting embodiment, the bubble sensor fault alarm state involves displaying a warning symbol, such as a triangle, with three exclamation points, and a red banner, which flashes at a predetermined rate. However, unlike the bubble detection high priority alarm state, while in the bubble sensor fault alarm state, none of the bubble size indicators of the bubble detection data field 166 are filled with red color, but they are filled with the color of the background, and a large red "X" is superposed over the bubble detection data field 166. In another embodiment of this disclosure, in addition to the visual component of the bubble sensor fault alarm state disclosed above, the bubble sensor fault alarm state may include an auditory alarm that comprises sound (e.g., a high pitch beeping) that pulses in a predetermined cadence. In accordance with an embodiment of this disclosure, when the bubble detection sensor module 162 is in the bubble sensor fault alarm state, the reset button 167 is not enabled.

Figure 14E:
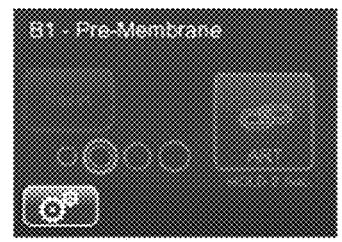

As shown in FIG. 14*e*, when the bubble detection sensor 60 is configured to an off state, the bubble detection sensor module 162 transitions to a bubble detection sensor unavailable state. The bubble detection sensor unavailable alarm state may be configured in a variety of ways. In one non-limiting embodiment, the bubble detection sensor unavailable state involves displaying a dark banner and a subdued bubble detection data field 166. When in the bubble detection sensor unavailable state, the reset button 167 and the intervention button 168 are not enabled, although the module settings menu button 124 is enabled. In accordance with an embodiment of this disclosure, the reset button 167 and the intervention button 168 are displayed in a subdued mode to indicate that they are not activatable (enabled) during the bubble detection sensor unavailable state as shown by FIG. 14*e*. However, the module settings menu button 124 is displayed in an illuminated mode, as shown in FIG. 14*e*, to indicate its activatable (enabled) condition.

Level Sensor Modules

Figure 15A:
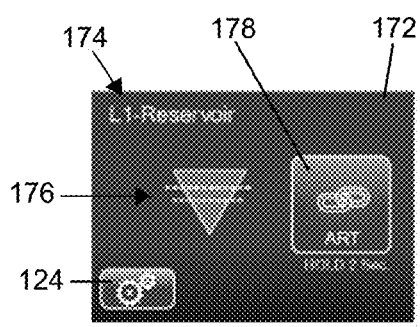
FIGS. 15a, 15b and 15c (which may be collectively referred to as "FIG. 15") illustrate an exemplary, non-limiting configuration of a level sensor module, including various fluid level detection states, in accordance with an embodiment of this disclosure.

The cardiopulmonary bypass system 1 may be provided with one or more level sensors 70 disposed to detect fluid level in a blood reservoir, typically a venous reservoir, which constitutes a component of the extracorporeal blood flow circuit 3 of the cardiopulmonary bypass system 1. Each level sensor 70 is operably connected to input fluid level data to the processor 30, which may process the fluid level data before outputting it to the graphical user interface 100 for display. Data from level sensor 70 may be displayed by a corresponding unique level sensor module 172, such as shown in FIG. 15*a*. Each level sensor module 172 is a display module that may be displayed in any of the four quadrants 108, whether as a component of an untabbed display page, or whether as a component of a tabbed sensor display page, or whether as a component of a tabbed Cardioplegia display page, depending on the application and set-up per the user's preferences. As a non-limiting example, level sensor modules are illustrated as a component of the untabbed display page 115 as shown in FIG. 3*b*.

As shown in FIG. 15*a*, each unique level sensor module 172 includes a title field 174, which is an alphanumeric field that displays a unique identifier pertaining to the level sensor 70 from which displayed data is obtained. The unique identifier may have the form of "Lx –," in which x is a number corresponding to a specific level sensor, followed by a sensor name, such as may indicate location along the extracorporeal blood flow circuit. The sensor name shown in FIG. 15a is merely exemplary, for illustration purposes, and is not meant to be limiting.

Each level sensor module 172 also includes a level data field 176, which is a graphical field that displays via a level icon relative level data obtained by the level sensor 70. More specifically, the level data obtained by the level sensor 70 relates to the position of the level sensor 70. Each level sensor module 172 may further include an intervention button 178 that, under appropriate circumstances, is activatable to override an automatic level correction algorithm that automatically adjusts blood fluid level in blood reservoir 70 via operation of a blood fluid pump 37 of the cardiopulmonary bypass machine 1, as described in more detail below. The pump 37 operably connected to the intervention button 178 is of a kind that pumps blood fluid from the blood reservoir 70. Each level sensor module 172 also includes a module settings menu button 124 as discussed above.

Level icon(s) of the level data field 176 are described with reference to FIGS. 16a, 16b, 16c and 16d. Each of the level icons graphically represents a relative level of fluid in the associated reservoir. For example, the level icon of FIG. 16a graphically represents an acceptable level of fluid within the blood reservoir (i.e., a level above a regulation level). The illustrated embodiment employs a green triangle in accordance with industry standards for medical devices. However, when the graphical user interface 100 is employed as a component of a non-medical system then other colors and shapes may be employed to represent an acceptable relative level so long as they are readily appreciated as such by a user of the level sensor module 172. The green triangle icon is also provided with two horizontal white dashed lines, which represent other important relative levels as are described below with respect to other level icons.

Figure 15B:
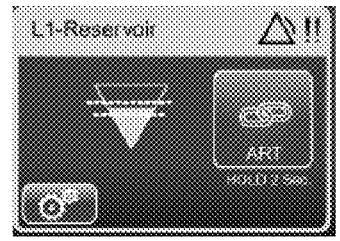
Figure 16A:
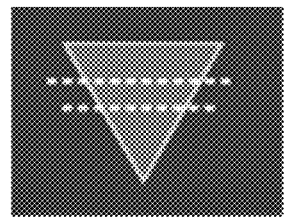
FIGS. 16a, 16b, 16c and 16d (which may be collectively referred to as "FIG. 16") illustrate various level icons representing relative levels of fluid in the associated reservoir in accordance with an embodiment of this disclosure.
Figure 16B:
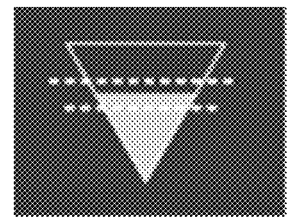

The level icon of FIG. 16b graphically represents a level of fluid within the blood reservoir that is lower than the level of fluid graphically represented by the level icon of FIG. 16a. In fact, the level of fluid graphically represented by the level icon of FIG. 16b is at or below a regulation limit, which is represented by the upper horizontal dashed line, and above the level of the level sensor 70, which is represented by the lower horizontal dashed line. While the fluid level graphically represented by FIG. 16b is still an acceptable level of fluid, it represents a fluid level meriting more close attention in accordance with a level low priority alarm state, such as represented by FIG. 15b. This level low priority alarm state may be configured in a variety of ways. For example, as shown in FIG. 15b, the coloring of graphically represented fluid level may be altered from green to yellow, and a yellow banner may be provided with a triangle warning icon and two exclamation points that maintain a steady non-flashing state when activated. In another embodiment of this disclosure, in addition to the visual component of the level low priority alarm state, the level low priority alarm state may include an auditory alarm that comprises sound (i.e., a low or medium pitch sound) that pulses in a predetermined cadence that indicates the level low priority alarm state.

Figure 15C:
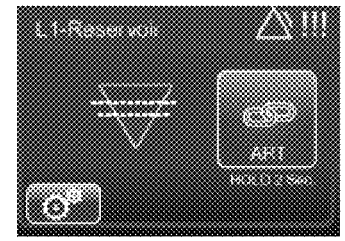
Figure 16C:
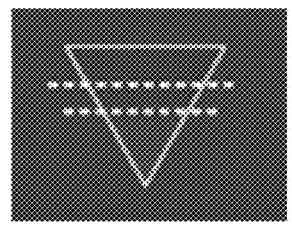

The level icon of FIG. 16c graphically represents a level of fluid within the blood reservoir that is lower than the level of fluid graphically represented by the level icon of FIG. 16b, and corresponds to a fluid level that is at or below the level of the level sensor 70, as represented by the lower horizontal dashed line. The fluid level graphically represented by FIG. 16c is not an acceptable level of fluid because of the risk associated with the blood reservoir running dry, so it corresponds to a level high priority alarm state, such as shown by FIG. 15c. This level high priority alarm state may be configured in a variety of ways. For example, the coloring of graphically represented fluid level may be altered to red, a red banner may be provided along with a triangle warning icon and three exclamation points, and the level icon may be made to flash at a predetermined rate indicative of the level high priority alarm state. In another embodiment of this disclosure, in addition to the visual component of the level high priority alarm state, the level high priority alarm state may include an auditory alarm that comprises sound (i.e., a high pitch sound) that pulses in a cadence that is indicative of the level high priority alarm state.

When the level data field 176 displays the level icon of FIG. 16c, thereby indicating the level high priority alarm state, then the need to correct the low fluid level in the blood reservoir has become urgent. In this case, the processor 30 initiates an automatic level correction algorithm, which involves adjusting the operation of blood pump 38, or some other blood pump, so that blood fluid accumulates in the blood reservoir 36, thereby raising the blood fluid level. The intervention button 178 becomes activatable under these circumstances so that a user may activate the intervention button 178 by pressure or touch on the touch screen 17 and override the automatic level correction algorithm for a period of two seconds. Such an override interrupts the automatic level correction algorithm so that blood pump 38 resumes its previous state of operation before activation of the automatic level correction algorithm.

When the level icon displayed is the icon of FIG. 16b, the level sensor module 172 may display the configuration illustrated by FIG. 15b when the pump, operably associated with the level sensor module and the intervention button 178, is an arterial blood pump 38. When the level icon displayed is the icon of FIG. 16c, the level sensor module 172 may display the configuration illustrated by FIG. 15c when the pump, operably associated with the level sensor module and the intervention button 178, is an arterial blood pump 38.

Figure 16D:

The condition graphically represented by FIG. 16d corresponds to the situation in which level data is not available for the particular blood reservoir sensor. The level icon displayed by the level data field 176 of the level sensor module 172 may transition automatically, as appropriate, between any of the states graphically represented by FIGS. 16a, 16b, 16c and 16d. In this way, the level sensor module 172 may indicate fluid level in the fluid reservoir without having the user perform any reset functions.

The illustrated embodiments of the level icons of FIGS. 16a, 16b, 16c and 16d are non-limiting; however, they are in accordance with industry standards for medical devices. When the graphical user interface 100 is employed in a non-medical system, then other shapes and/or colors may be employed to graphically illustrate various relative fluid levels for the corresponding blood reservoir so long as the various relative fluid levels are readily appreciated as such by a user of the level sensor module 172.

In some cases, a fluid level sensor 70 may be associated with a level sensor module 172 that is operably connected with intervention button 178 to an air removal pump 39 (i.e., a vacuum pump) rather than to a blood pump 37 or 38. In such a case, during the automatic level correction algorithm the processor 30 manipulates the operation of the air removal pump 39 in order to increase the blood flow into the blood reservoir 36, thereby increasing the blood fluid level in the blood reservoir 36. Under these circumstances, activation of the intervention button 178 becomes possible. Activation of the intervention button 178 by touch or pressure overrides the automatic level correction algorithm for a period of two seconds, and during the period of override the air removal pump 39 operates as it would before the automatic level correction algorithm was initiated.

Figure 17A:
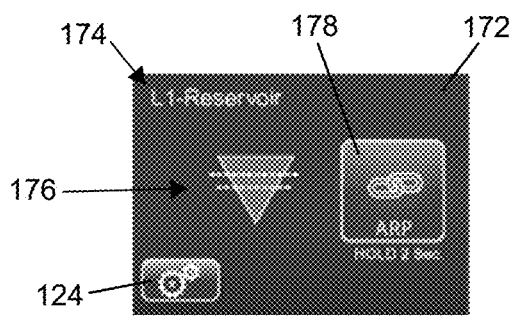
FIGS. 17a, 17b, 17c and 17d (which may be collectively referred to as "FIG. 17") illustrate an exemplary, non-limiting configuration of a level sensor module, including various fluid level detection states, in accordance with an embodiment of this disclosure when a vacuum pump is connected to the blood reservoir.
Figure 17B:
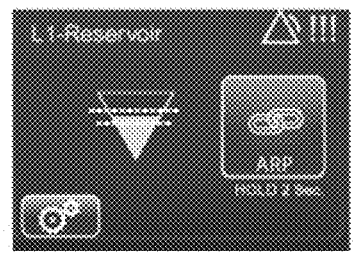
Figure 17C:
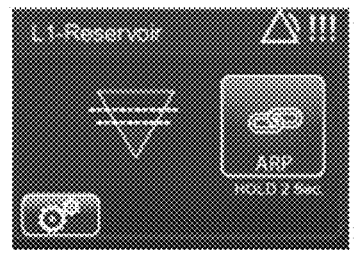

The level sensor module 172 may exhibit various states as shown in FIGS. 17a, 17b and 17c. A blood pump, in accordance with this disclosure, is a pump connected to the blood reservoir 36 and to the extracorporeal blood flow circuit 3 of the cardiopulmonary bypass system 1 for the purposes of pumping primarily blood fluid through the extracorporeal blood flow circuit. While such blood fluid may include a trivial amount of air in the form of microbubbles, the bulk of the volume pumped by a blood pump is primarily blood fluid. An air removal pump, in accordance with this disclosure, is a pump connected to the blood reservoir 36 so as to remove air from the blood reservoir. While such removed air may include some blood fluid, the bulk of the volume pumped by the air removal pump is generally air.

When the level sensor module 172 is operably connected with intervention button 178 to an air removal pump 39, and the blood fluid in the blood reservoir is at an acceptable level (i.e., above a regulation level), then the level sensor module 172 will manifest as in FIG. 17a. FIG. 17a is substantially similar to FIG. 15a with respect to possessing a title field 174, a level data field 176, an intervention button 178, and a module settings menu button 124. However, the intervention button 178 of FIG. 17a identifies an "ARP" (air removal pump) rather than an "ART" (blood pump on arterial side).

While the blood fluid level in the blood reservoir is at an acceptable level and the level sensor module 172 displays as in FIG. 17a, the air removal pump may be disengaged, which means that it is not operating to draw a vacuum with respect to an air pocket normally present in the blood reservoir. When the level of fluid within the blood reservoir is lower than the level of fluid graphically represented by the level icon of FIG. 17a so that the level of fluid is at or below a regulation limit (represented by the upper horizontal dashed line), but above the level of the level sensor 70 (represented by the lower horizontal dashed line), then the level sensor module 172 will manifest as in FIG. 17b. This state corresponds to a level high priority state with respect to the air removal pump, and may be configured in a variety of ways. For example, the coloring of graphically represented fluid level may be altered from green to yellow, and a red banner may be provided with a triangle warning icon and three exclamation points, and the level icon may be made to flash at a predetermined rate in accordance with this alarm state. In another embodiment of this disclosure, in addition to the visual component of the level high priority alarm state, the level high priority alarm state may include an auditory alarm that comprises sound (i.e., a medium or high pitch sound) that pulses in a cadence that indicates this level of high priority alarm state.

When the level sensor module 172 displays the level high priority alarm state of FIG. 17b, the air removal pump automatically engages due to initiation of an automatic level correction algorithm in order to impose a vacuum on the air pocket within the blood reservoir 36. This vacuum helps draw blood into the blood reservoir from the extracorporeal blood flow circuit of the cardio-pulmonary bypass machine 1. At the same time, the intervention button 178 becomes activatable by a user by touch or pressure. When the user activates the intervention button 178 by touch or pressure under these conditions, the automatic level correction algorithm is temporarily overridden for a period of two seconds so the air removal pump temporarily resumes its operative state that existed at the time the automatic level correction algorithm was activated.

The level icon of FIG. 17c graphically represents a level of fluid within the blood reservoir that is lower than the level of fluid graphically represented by the level icon of FIG. 17b, and corresponds to a fluid level that is at or below the level of the level sensor 70, as represented by the lower horizontal dashed line. This state also corresponds to a level high priority alarm state, and is similar to FIG. 17b in that it displays a similar banner and warning symbols as FIG. 17b, namely, the red banner, the triangle warning icon and three exclamation points, and the level icon may flash at a predetermined rate corresponding to this level high priority alarm state. In accordance with this level high priority alarm state, the color of graphically represented fluid level may transition from yellow to red. In another embodiment of this disclosure, in addition to the visual component of this level high priority alarm state, the level high priority alarm state may include an auditory alarm that comprises sound (i.e., a high pitch sound) that pulses in a cadence that matches this degree of level high priority alarm state.

When the level sensor module 172 displays the level high priority alarm state of FIG. 17c, the air removal pump automatically engages, or continues to be automatically engaged, according to the automatic level correction algorithm to impose a vacuum on the air pocket within the blood reservoir in order to help draw blood into the blood reservoir from the extracorporeal blood flow circuit. At the same time, the intervention button 178 is activatable so at to be touch or pressure activatable by a user. When the user activates the intervention button 178 under these conditions, automatic level correction algorithm is temporarily overridden for a period of two seconds so that the air removal pump resumes its operative state in effect at the time the automatic level correction algorithm activated.

Figure 17D:
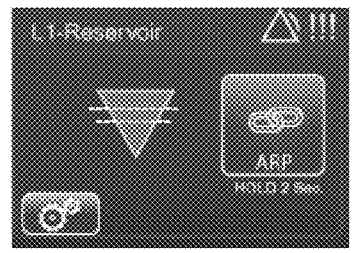

When the level sensor module 172 has been displaying a level high priority alarm state, such as corresponds to FIG. 17b or 17c, and then subsequently transitions to displaying a state corresponding to FIG. 17d, namely, a condition where the blood fluid level in the blood reservoir is in at an acceptable level, the air removal pump initially remains active to impose a vacuum on the air pocket of the blood reservoir for the duration of a hysteresis period in accordance with the automatic level correction algorithm. During this hysteresis period, the level sensor module 172 displays a level high priority alarm state as shown in FIG. 17d, and the intervention button 178 remains activatable. According to the alarm state represented by FIG. 17d, the level data field 176 displays the level icon of FIG. 16a, thereby indicating an acceptable level of blood fluid in the blood reservoir. However, the banner remains red and the triangular warning icon and the three exclamation points continue to be displayed to inform the user that the air removal pump is still engaged and drawing a vacuum.

After the hysteresis period expires, and the blood level of the blood reservoir detected by the level sensor 70 remains acceptable, then the level sensor module 172 transitions to display the images according to FIG. 17a. At this time, the manipulation of the air removal pump under the automatic level correction algorithm ceases as the automatic level correction algorithm ceases, and the intervention button 178 transitions to a state in which it is not activatable by touch or pressure.

The illustrated embodiments of the level icons of FIGS. 17a, 17b, 17c and 17d are non-limiting; however, they are in accordance with industry standards for medical devices.

When the graphical user interface 100 is employed as a component of a non-medical system, then other shapes and/or colors may be employed to graphically illustrate various relative fluid levels for the corresponding blood reservoir so long as the various relative fluid levels are readily appreciated as such by a user of the level sensor module 172.

Figure 18A:
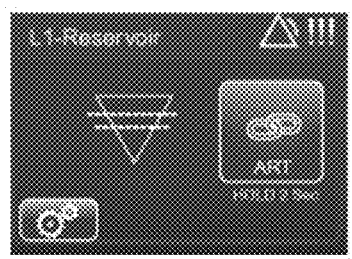
FIGS. 18a, 18b and 18c illustrate various alarm states of a level sensor module in accordance with an embodiment of this disclosure.

The level sensor module 172 is capable of transitioning to several additional alarm states. For example, as shown in FIG. 18a, in the case when the level sensor 70 becomes disconnected from the sensor panel, the level sensor module 172 transitions to a level disconnect high priority alarm state. The level disconnect high priority alarm state may be configured in a variety of ways. In one non-limiting embodiment, the level disconnect high priority alarm state involves displaying a warning symbol, such as a triangle, with three exclamation points, and a red banner, which flashes at a predetermined rate. However, unlike other level high priority alarm states, while in the level disconnect high priority alarm state, the level icon of the level data field 176 is filled with black color so as not to indicate a level. In another embodiment of this disclosure, in addition to the visual component of the level disconnect high priority alarm state described above, the level disconnect high priority alarm state may include an auditory alarm that comprises sound (e.g., a high pitch beeping) that pulses in a predetermined cadence that is indicative of the level disconnect high priority alarm state.

Figure 18B:
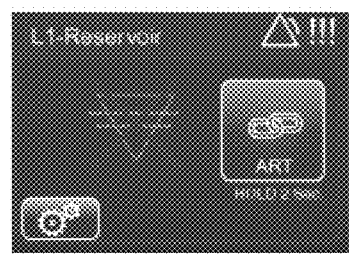

When the level sensor 70 is enabled but malfunctioning in some way, so as to return a fault status, the level sensor module 172 transitions to a level fault alarm state as shown in FIG. 18b. The level fault alarm state may be configured in a variety of ways. In one non-limiting embodiment, the level fault alarm state involves displaying a warning symbol, such as a triangle, with three exclamation points, and a red banner, which flashes at a predetermined rate. In addition, while in the level fault alarm state, the level icon of the level data field 176 is filled with black color and a large red "X" is superposed over the level data field 176. In another embodiment of this disclosure, in addition to the visual component of the level fault alarm state disclosed above, the level fault alarm state may include an auditory alarm that comprises sound (e.g., a high pitch beeping) that pulses in a predetermined cadence that is indicative of the level fault alarm state.

Figure 18C:
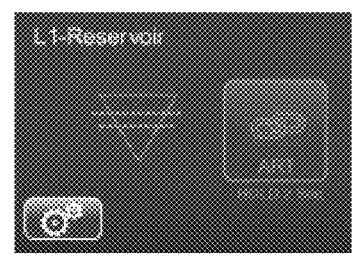

When the level sensor 70 is configured to an off state, the level sensor module 172 transitions to a level sensor unavailable state as shown in FIG. 18c. The level sensor unavailable state may be configured in a variety of ways. In one non-limiting embodiment, the level sensor unavailable state involves displaying a dark banner and a subdued level data field 176, which may be filled with black color as well. When in the level sensor unavailable state, the intervention button 178 is not activatable, although the module settings menu button 124 may be activated by touch or pressure.

Temperature Sensor Modules

Figure 19A:
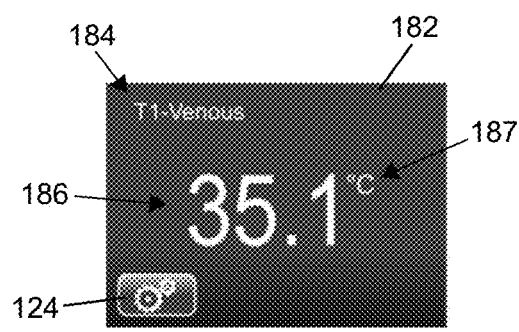

The cardiopulmonary bypass system 1 is typically provided with one or more temperature sensors 80 disposed to measure temperature at various desired points on the extracorporeal blood flow circuit 3, and/or to measure temperature of the patient, and/or to measure temperature of the heart during cardioplegia, and to input temperature data to the processor 30, which may process the temperature data before outputting it to the graphical user interface 100 for display. Data from each temperature sensor 80 is displayed by a corresponding unique temperature sensor module 182, such as shown in FIGS. 19a, 19f and 19g. FIG. 19a is similar to FIGS. 19f and 19g except that FIGS. 19f and 19g include an icon field 188 and 189, respectively, that display information regarding association with a cardioplegia circuit. More specifically, icon field 188 indicates that the temperature sensor 80 is associated with a cardioplegia heating-cooling unit, and measures temperature of the blood fluid of the extracorporeal blood flow circuit 3. This association is graphically indicated by the sun and snowflake symbols and the body symbol. Icon field 189 indicates that the temperature sensor 80 is associated with the cardioplegia heating-cooling unit, and measures temperature of the cardioplegia solution. This association is graphically indicated by the sun and snowflake symbols and the heart symbol.

The temperature sensor modules 182 are display modules that may be displayed in any of the four quadrants 108, as appropriate as a component of an untabbed display page, or as a component of a tabbed sensor display page, or as a component of a tabbed Cardioplegia display page, depending on the application and set-up per the user's preferences. As a non-limiting example, temperature sensor modules are illustrated as components of the tabbed display pages 116 and 121, and as a component of the tabbed Cardioplegia display page 110, as shown in FIG. 3b.

As shown in FIG. 19a, each unique temperature sensor module 182 includes a title field 184, which is an alphanumeric field that displays a unique identifier pertaining to the temperature sensor 80 from which displayed data is obtained. The unique identifier may have the form of "Tx -," in which x is a number corresponding to a specific temperature sensor, followed by a sensor name, such as may indicate location along the extracorporeal blood flow circuit 3. The sensor name shown in FIG. 19a is merely exemplary, for illustration purposes, and is not meant to be limiting.

Each temperature sensor module 182 also includes a temperature value data field 186, which is a numerical field that displays the value of the temperature data measured by the temperature sensor 80, and a temperature value unit field 187, which is an alphanumeric field that displays the units of the temperature data measured by the temperature sensor 80. The temperature value unit field 187 may indicate temperature units in degrees centigrade or in degrees Fahrenheit. In accordance with an embodiment of this disclosure, the temperature value data field 186 and the temperature value unit field 187 may be integrated together as a single field. Each temperature sensor module 182 also includes a module settings menu button 124 as discussed above.

Figure 19B:
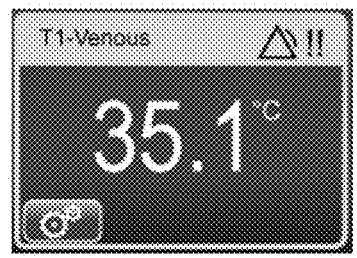

Each temperature sensor module 182 may further include a plurality of alarm indicating states as illustrated by FIGS. 19b, 19c and 19d. For example, as shown by FIG. 19b, when the temperature sensor 80 measures temperature in the extracorporeal blood flow circuit that reaches and/or exceeds an upper limit value, or that reaches and/or drops below a lower limit value, then temperature sensor module 182 switches to a temperature medium priority alarm state. The temperature medium priority alarm state may be configured in a variety of ways. In one non-limiting embodiment, the temperature medium priority alarm state involves displaying a warning symbol, such as a triangle, with paired exclamation points, and a yellow banner, which may flash at a predetermined rate that is indicative of the medium priority alarm state. In another embodiment of this disclosure, in addition to the visual component of the temperature medium priority alarm state described above, the temperature medium priority alarm state may include an auditory alarm that comprises sound (e.g., a medium pitch beeping) that pulses in a cadence that is indicative of the temperature medium priority alarm state.

The particular color scheme for the medium priority alarm banner that has been described with respect to temperature measurement, namely a yellow banner, is consistent with industry standards for medical devices. Other color schemes may be employed as well when the graphical user interface 100 is employed solely with non-medical devices, in accordance with various alternate embodiments of this disclosure.

The temperature sensor module 182 is capable of transitioning to several additional alarm states. In FIG. 19c, the temperature sensor module 182 is indicating the state in which the temperature sensor 80 is disconnected from the processor 30, such as may occur when the temperature sensor 80 disconnects from the sensor panel. In FIG. 19d, the temperature sensor module 182 is indicating the state in which the temperature sensor 80 is malfunctioning. In FIG. 19e, the temperature sensor module 182 is indicating the state in which the pressure sensor 80 is unavailable, such as when the temperature sensor 80 is in an "off" configuration.

Flow Sensor Modules

The cardiopulmonary bypass system 1 is typically provided with one or more blood flow sensors 90 disposed to measure blood fluid flow at various desired points on the extracorporeal blood flow circuit 3, and to input blood fluid flow data to the processor 30, which may process the blood fluid flow data before outputting it to the graphical user interface 100 for display. Data from each flow sensor 90 is displayed by a corresponding unique flow sensor module 192, such as shown in FIG. 20a. The flow sensor modules 192 are display modules that may be displayed in any of the four quadrants 108, as appropriate, as a component of an untabbed display page, or as a component of a tabbed sensor display page, or as a component of a tabbed Cardioplegia display page, depending on the application and set-up per the user's preferences. As a non-limiting example, flow sensor modules are illustrated as a component of the untabbed display page 115, and as components of the tabbed display page 116, as shown in FIG. 3b.

As shown in FIG. 20a, each unique flow sensor module 192 includes a title field 194, which is an alphanumeric field that displays a unique identifier pertaining to the flow sensor 90 from which displayed data is obtained. The unique identifier may have the form of "Fx –," in which x is a number corresponding to a specific flow sensor, followed by a sensor name, such as may indicate location along the extracorporeal blood flow circuit. The sensor name shown in FIG. 20a is merely exemplary, for illustration purposes, and is not meant to be limiting.

Each flow sensor module 192 also includes a flow value data field 196, which is a numerical field that displays the value of the flow data measured by the flow sensor 90, and a flow value unit field 197, which is an alphanumeric field that displays the units of the flow data measured by the flow sensor 90. For example, the units displayed may be liters per minute (LPM). In accordance with an embodiment of this disclosure, the flow value data field 196 and the flow value unit field 197 may be integrated together as a single field. Each flow sensor module 192 also includes a module settings menu button 124 as discussed above.

Each flow sensor module 192 may further include a plurality of alarm indicating states as illustrated by FIGS. 20b, 20c, 20d and 20e. For example, as shown by FIG. 20b, when the flow sensor 90 measures flow of blood fluid in the extracorporeal blood flow circuit 3 that is negative (i.e., there is backward flow), then flow sensor module 192 switches to a flow medium priority alarm state. The medium high priority alarm state may be configured in a variety of ways. In one non-limiting embodiment, the flow medium priority alarm state involves displaying a warning symbol, such as a triangle, with two exclamation points, and a yellow banner, which flashes at a predetermined rate corresponding to the flow medium priority alarm state. In another embodiment of this disclosure, in addition to the visual component of the flow medium priority alarm state described above, the flow medium priority alarm state may include an auditory alarm that comprises sound (e.g., a medium pitch beeping) that pulses are indicative of the flow medium priority alarm state.

As shown by FIG. 20c, when the flow sensor 90 measures flow of blood fluid in the extracorporeal blood flow circuit 3 that reaches and/or exceeds an upper limit value, then flow sensor module 192 switches to a flow medium priority alarm state. This flow medium priority alarm state is configured in a manner similar to the medium priority alarm state provided when flow is negative.

While a particular color scheme for the flow high and medium priority alarm banners have been described with respect to blood fluid flow measurement, namely a red banner for high priority and a yellow banner for medium priority, this color scheme is in accordance with industry standards for medical devices. Other color schemes may be employed when the graphical user interface 100 is employed in a strictly non-medical monitoring environment in accordance with various embodiments of this disclosure in which no medical device is employed.

The flow sensor module 192 is capable of transitioning to several additional alarm states. In FIG. 20d, the flow sensor module 192 is indicating the alarm state in which the flow sensor 90 is disconnected from the processor 30, such as may occur when the flow sensor 90 disconnects from the sensor panel. In FIG. 20e, the flow sensor module 192 is indicating the alarm state in which the flow sensor 90 is malfunctioning. In FIG. 20f, the pressure sensor module 192 is indicating the notification state in which the pressure sensor 90 is unavailable, such as when the flow sensor 90 is in an "off" configuration.

Pressure Delta Modules

The sections 108 of the graphical user interface of the cardiopulmonary bypass system 1 may employ one or more pressure delta sensor modules 252, which are operably connected to at least two pressure sensors 50 disposed to measure pressure for comparison purposes at various desired points on the extracorporeal blood flow circuit 3, and to input two sources of pressure data to the processor 30, which may process the pressure data to generate pressure delta data before outputting the pressure delta data to the graphical user interface 100 for display. Such generated pressure delta data from paired pressure sensors 50, as calculated by the processor 30, is displayed by a corresponding unique pressure delta sensor module 252, such as shown in FIGS. 21a and 21b. FIG. 21a is similar to FIG. 21b except that FIG. 21a displays pressure delta data in mmHg and FIG. 21b displays pressure delta data in kPa. The pressure delta data sensor modules 252 are display modules that may be displayed in any of the four quadrants 108, as appropriate as a component of an untabbed display page, or as a component of a tabbed sensor display page, or as a component of a tabbed Cardioplegia display page, depending on the application and set-up per the user's preferences. As a non-limiting example, pressure delta data sensor modules are illustrated as a component of the untabbed display page 115 of FIG. 3b, and as a component of the tabbed display page 116, as shown in FIG. 3a.

As shown in FIG. 21a, each unique pressure delta data sensor module 252 includes a title field 254, which is an alphanumeric field that displays a unique identifier pertaining to the paired pressure sensors 50 from which displayed data is obtained. The unique identifier may have the form of "Pressure Delta Py-Px," in which x is a number corresponding to a specific first pressure sensor and y is a number corresponding to a specific second pressure sensor that is paired with the first pressure sensor for the purposes of calculating the pressure delta. The title example shown in FIG. 20a is merely exemplary, for illustration purposes, and is not meant to be limiting.

Each pressure delta data sensor module 252 also includes a pressure delta value data field 256, which is a numerical field that displays the value of the pressure delta data calculated from the pressures measured by the paired pressure sensors 50, and a pressure delta data value unit field 257, which is an alphanumeric field that displays the units of the pressure delta data calculated from measured pressure data provided by paired pressure sensors 50. In accordance with an embodiment of this disclosure, the pressure delta value data field 256 and the pressure delta value unit field 257 may be integrated together as a single field. Each pressure delta data sensor module 252 also includes a module settings menu button 124 as discussed above.

Each pressure delta data sensor module 252 may further include an alarm indicating state as illustrated by FIG. 21c. When the calculated pressure delta data value reaches and/or exceeds a threshold limit value, then pressure sensor module 252 switches to a pressure delta medium priority alarm state as shown by FIG. 21c. The pressure delta medium priority alarm state may be configured in a variety of ways. In one non-limiting embodiment, the pressure delta medium priority alarm state involves displaying a warning symbol, such as a triangle, with two exclamation points, and a yellow banner, which flashes at a predetermined rate indicative of the medium priority alarm state. In another embodiment of this disclosure, in addition the visual component of the pressure delta medium priority alarm state disclosed above, the pressure delta medium priority alarm state may include an auditory alarm that comprises sound (e.g., a medium pitch beeping) that pulses in a predetermined cadence indicative of the pressure delta medium priority alarm state.

A particular color scheme for the medium priority alarm banner has been described with respect to pressure delta determinations, namely, a yellow color, in accordance with industry standards for medical devices. However, other color schemes may be employed in accordance with various embodiments of this disclosure when the graphical user interface 100 is used in a strictly non-medical monitoring environment and is not associated with any medical devices.

In FIG. 21d, the pressure delta data sensor module 252 is indicating the notification state in which the one or both of the paired pressure sensors is unavailable. This may occur when one or both of the pressure sensors 50 in an "off" configuration.

Besides the various sensor modules discussed above, the tabbed and untabbed display pages may be provided with components selected from various non-sensor modules. For example, the untabbed display page 116 employs a non-sensor module in sector 122h, as shown in FIG. 9. This non-sensor module displays timer data, such as time during a cardiopulmonary bypass procedure directed to perfusion, and to cross-clamping, and to re-perfusion, which are different portions of the cardiopulmonary bypass procedure. This example of a non-sensor module should be construed as merely exemplary and, therefore, non-limiting.

Non-limiting Examples of Untabbed and Tabbed Display Pages

Having described a number of non-limiting illustrative examples of sensor modules and non-sensor modules, such as may be employed by a user to selectively construct various untabbed and tabbed display pages of the graphical user interface 100, several non-limiting illustrative examples of untabbed and tabbed display pages are described in order to highlight the modular construction of the untabbed and tabbed display pages as well as the flexibility and customization provided by the selectability associated with this modular construction.

Non-limiting Illustrative Untabbed Display Page Configurations

The untabbed display page of section 108a of FIG. 3a includes two pressure sensor modules (i.e., P1—Pre-Membrane and P2—Pre-Membrane), two bubble detection sensor modules (i.e., B1—Pre-Membrane and B2—Pre-Membrane) and two level sensor modules (i.e., L1—Reservoir and L2). One of the pressure sensor modules (i.e., P2—Pre-Membrane) is operably linked to an arterial pump so that activation of its intervention button will affect the operation of an arterial pump so linked; however, the other pressure sensor module (i.e., P1—Pre-Membrane) is not linked to any pump as evident from the icon of a broken chain with an X-mark overlying the broken chain. One of the bubble detection sensor modules (B1—Pre-Membrane) is operably linked to the arterial pump, so that activation of the intervention button of this bubble sensor detection module will affect the operation of the arterial pump. The other one of the bubble detection sensor modules (B2—Pre-Membrane) is operably linked to an auxiliary pump, so that activation of the intervention button of this bubble sensor detection module will affect the operation of the linked auxiliary pump. One of the level sensor modules (i.e., L2) is operably linked to the auxiliary pump so that activation of the intervention button of this module would affect operation of the auxiliary pump. The other level sensor module (i.e., L1—Reservoir) is not linked to any pump because it is in an "off" state as evident from the icons.

The untabbed display page of section 108a of FIG. 3b illustrates a different configuration from that of section 108a of FIG. 3a. FIG. 3b illustrates two pressure sensor modules (i.e., P1—Pre-Membrane and P2—Post-Membrane), one pressure delta sensor module (i.e., Pressure Delta P2—P1), one bubble detection sensor module (i.e., B2 Post-Membrane), two level sensor modules (i.e., L1—Reservoir and L2), and a flow sensor module (i.e., F1—Pre-Membrane). One of the pressure sensor modules (i.e., P1—Pre-Membrane) is not linked to a pump as evident from the outlined broken chain icon of the intervention button, so its intervention button cannot affect the operation of any pump due to its unlinked state. The other pressure sensor module (i.e., P2—Post-Membrane) is operably linked to an arterial pump, as evident from the icon of a non-outlined intact chain corresponding to the intervention button, so that activation of the intervention button of this pressure sensitive module should at least temporarily affect the operation of the linked arterial pump. The bubble detection sensor module (B2—Post-Membrane) is operably linked to the arterial pump, so that activation of the intervention button of this bubble sensor detection module will affect the operation of the arterial pump. One of the level sensor modules (i.e., L1—Reservoir) is operably linked to an air removal pump ("ARP"), which is a vacuum pump, so that activation of its intervention button will temporarily affect operation of the air removal pump. The other one of the level sensor modules (i.e., L2) is operably linked to the arterial pump so that activation of the intervention button of this sensor module should temporarily affect operation of the arterial pump.

The untabbed display page of FIG. 9 illustrates another non-limiting configuration, which includes two pressure sensor modules (i.e., P1—Pre-Membrane and P2—Pre-Membrane), two bubble detection sensor modules (i.e., B1—Pre-Membrane and B2—Pre-Membrane), two level sensor modules (i.e., L1—Reservoir and L2), one flow sensor module (i.e., F1—Pre-Membrane), and a non-sensor module (i.e., Timers). The two pressure sensor modules are operably linked to the same arterial pump so that activation of either of the intervention buttons of the P1—Pre-Membrane pressure sensor module or of the P2—Pre-Membrane pressure sensor module temporarily affects the operation of the arterial pump. On the other hand, the B1—Pre-Membrane bubble detection sensor module is operably linked to the arterial pump and the B2—Pre-Membrane bubble detection sensor module is operably linked to an auxiliary pump. Therefore, activation of the intervention button of the B1—Pre-Membrane bubble detection sensor module temporarily affects operation of the arterial pump whereas activation of the intervention button of the B2—Pre-Membrane bubble detection sensor module temporarily affects operation of the auxiliary pump. The L1—Reservoir level sensor module is operably linked to an air removal pump and the L2 level sensor module is operably linked to an auxiliary pump. Therefore, activation of the intervention button of the L1—Reservoir sensor module temporarily affects operation of the air removal pump (i.e., an air pump) whereas activation of the intervention button of the L2 level sensor module temporarily affects operation of the auxiliary pump (i.e., a blood fluid pump).

The non-sensor module 125h is an informational display pertaining to various timers useful during a cardiopulmonary bypass procedure, such as, for example, timers to record the duration of perfusion, the cross-clamp duration, and the duration of re-perfusion. The non-sensor module 125h does not include a module settings menu button.

The configurations of FIGS. 3a, 3b and 9 constitute merely non-limiting examples to demonstrate the flexible and reconfigurable nature of untabbed display pages. In an embodiment of this disclosure, the central monitoring portion 106 includes only one untabbed display page and one, two or three tabbed display pages, and the untabbed display page is divided into a plurality of sectors, and each sector may be configured with one module selected from the group consisting of a pressure sensor module, a bubble detection sensor module, a level sensor module, a temperature sensor module, a flow sensor module and a timer module (i.e., a non-sensor module).

Non-Limiting Illustrative Tabbed Display Page Configurations for Cardioplegia

The tabbed display pages of section 108b of FIGS. 3a and 3b pertain to a cardioplegia display interface, such as may pertain to sensor data, pumps, and other components of a cardioplegia bypass machine directed to performing cardioplegia during a cardiopulmonary bypass procedure. For example, the tabbed display page 110, as shown in FIG. 3b and whose tab 110a is the only portion of the tabbed display page 110 viewable in FIG. 3a, may be configured to include a pressure sensor module (i.e., P3—Cardioplegia), a temperature sensor module (i.e., T1—Cardioplegia), and a bubble detection sensor module (i.e., B2—Cardioplegia). The pressure sensor module and the bubble detection sensor module are both operably linked to the same Cardioplegia ("CPU") pump so that activation of the intervention button for either the P3—Cardioplegia pressure sensor module or the B2—Cardioplegia bubble detection module temporarily affects operation of the Cardioplegia pump. This tabbed display page also includes a non-sensor module (i.e., Total Cardioplegia Volume), which is used to manually keep track of the amount of fluid volume administered to the patient with respect to the progression of the Cardioplegia procedure. The tabbed display page of section 108b, as shown by FIG. 3b, also includes a timer module pertaining to tracking Cardioplegia pause time, and a Cardioplegia Delivery module. The tabbed display page 110 has a reset button labeled "Reset Actual Cardioplegia," which resets the page when touch or pressure activated for at least two seconds.

The tabbed display page 111, as shown in FIG. 3a and whose tab 111a is the only portion viewable in FIG. 3b, pertains to a timer display interface. Tabbed display page 111 includes a non-sensor timer module, which displays various timers used during a cardiopulmonary bypass procedure to record the duration of perfusion, cross-clamping, and re-perfusion during cardiopulmonary bypass. These non-sensor modules pertaining to timing perfusion, cross-clamping and re-perfusion, do not include a module settings menu button. Tabbed display page 111 also includes a non-sensor timer module comprising a crystalloid deliver timer and an infusion timer, which may be operably linked to a crystalloid delivery pump and to an infusion delivery pump, as evident from the module settings menu button. Tabbed display page 111 may also include a non-sensor count-up timer and a count-down timer module, which includes a count-up timer and a count-down timer. Each of the timers of tabbed display page 111 may be selectively reset by continuously pressing the corresponding timer reset field for at least two seconds.

Non-Limiting Illustrative Tabbed Display Page Calculator Configurations

Figure 22A:
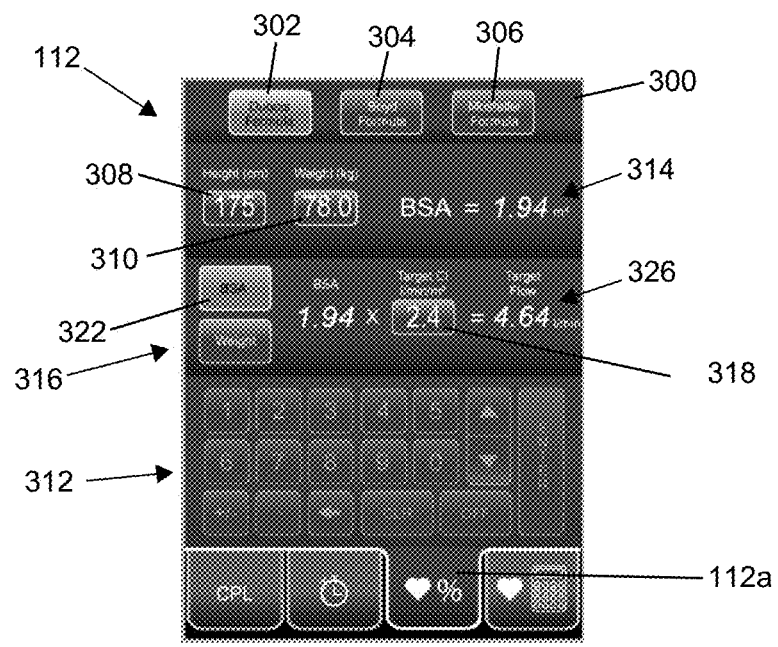
FIGS. 22a and 22b (which may be collectively referred to as "FIG. 22") illustrate an exemplary, non-limiting example of a tabbed display page directed to a weight based target flow calculator user interface in accordance with an embodiment of this disclosure.
Figure 22B:
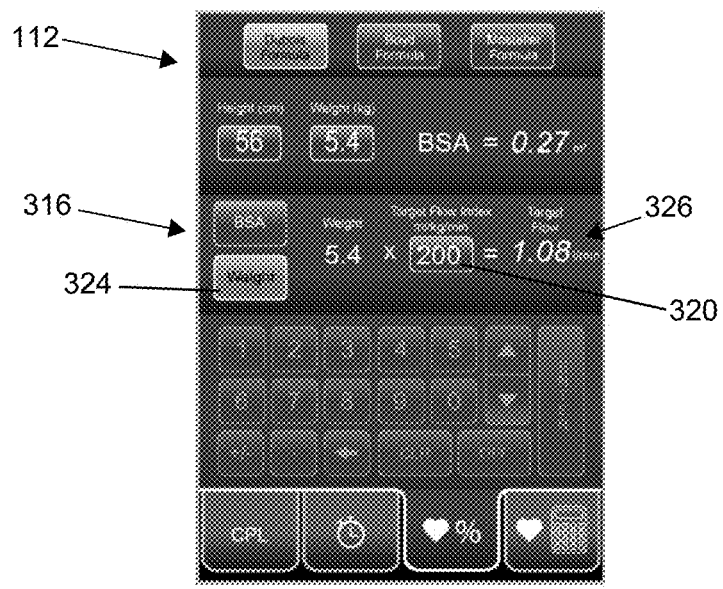

Tabbed display page 112 is illustrated in FIGS. 22a and 22b, and pertains to a weight based target flow calculator user interface in accordance with an embodiment of this disclosure. Tabbed display page 112 includes body surface area formula selection module 300 that has three formula selection buttons 302, 304, 306 depending upon whether the user of the interface wishes to employ the DuBois formula, the Boyd formula, or the Mosteller formula, respectively, to calculate out body surface area (BSA) based on the patient's height and weight in metric units, which are entered in data fields 308 and 310, respectively, using the touch or pressure sensitive keypad 312. The calculated BSA is displayed in data field 314. Tabbed display page 112 also includes a target flow module 316 that allows a user to calculate a patient's target flow for the extracorporeal blood flow circuit 3 as either the product of the patient's calculated BSA and a target Cardiac Index (CI) entered in data field 318 (FIG. 22a), or as the product of the patient's weight and a target Flow Index target entered in data field 320 (FIG. 22b). A user may select which target flow calculation to perform by activating either the BSA-based target flow calculation button 322 or the weight-based target flow calculation button 324. The result of the target flow calculation is displayed in data field 326. All of the above calculations are performed by the processor 30.

Tabbed display page 114 is illustrated in FIGS. 23a, 23b, 23c and 23d, and pertains to a perfusion calculator user interface in accordance with an embodiment of this disclosure. Tabbed display page 114 includes a perfusion parameter selection module 330 that has four touch or pressure sensitive selection buttons 332, 334, 336, 338, respectively, for selecting modules that allow the user to input patient parameters, calculate intra-cardiopulmonary fluids (intra-CPB), calculate out heparin dosing for the patient, or calculate the patient's indexed oxygen delivery $DO_2I$ and indexed oxygen consumption $VO_2I$, and optionally a ratio thereof, which are clinical parameters useful when monitoring a patient, such as disclosed in U.S. Patent Application Publication No. US 2006/0257283 A1, which is incorporated herein by reference for all that it discloses. In view of the touch or pressure sensitive selection buttons 332, 334, 336, 338, tabbed display page 114 has a non-nested sub-layered structure, which is substantially different from a nested structure. Tabbed display page 114 also includes a keypad 340 for entering data into data fields used for data entry.

Figure 23A:
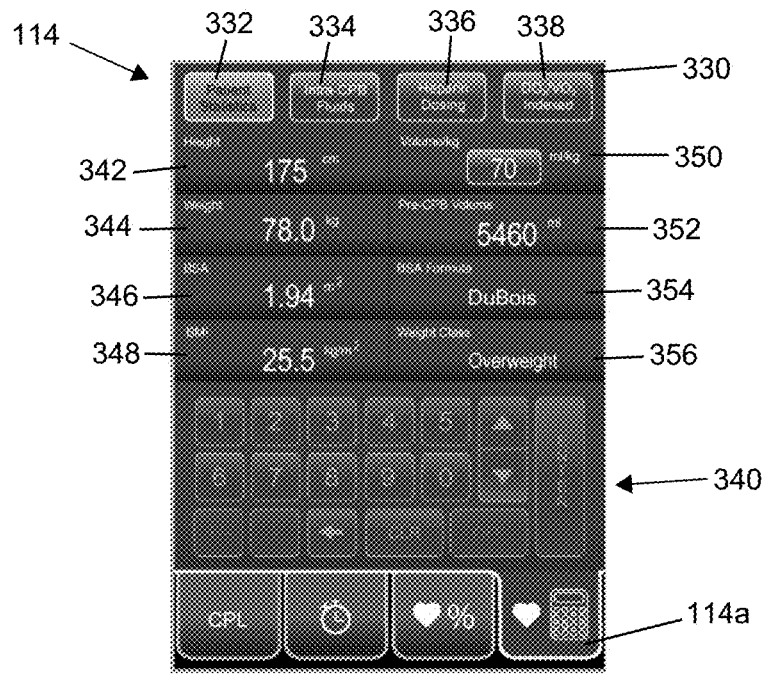
FIGS. 23a, 23b, 23c and 23d (which may be collectively referred to as "FIG. 23") illustrate an exemplary, non-limiting example of a tabbed display page directed to a perfusion calculator user interface in accordance with an embodiment of this disclosure.

When the "Patient Statistics" button 332 has been touch or pressure activated, tabbed display page 114 displays a patient statistics data input user interface, as shown by FIG. 23a, which has data input field 350 and data output fields 342, 344, 346, 348, 352, 354 and 356. Data output field 342 has a height data field that is autopopulated with the patient's height as entered into the data input field 308 of tabbed display page 112. Data output field 344 has a weight data field that is autopopulated with the patient's weight as entered into the data input field 310 of tabbed display page 112. Data output field 346 has a BSA data field for outputting the patient's body surface area (BSA), which is calculated by the processor 30 using one of the BSA formulas selectable using the tabbed display page 112. Data output field 348 has a body mass index (BMI) data field for outputting the patient's body mass index, which is calculated by the processor 30 using known formulas and the height and weight data autopopulated into data output fields 342 and 344. Data input field 350 has a volume/kg data field for entering, using keypad 340, an estimated intravascular blood volume per weight ratio for use in other calculations. Data output field 352 has a pre-CPB volume data field for outputting an estimated pre-CPB blood volume for the patient that is calculated by processor 30 based on known formulas and data displayed by data output fields 342, 344 and data input field 350. Data output field 354 has a data field for displaying the selected BSA formula (i.e., DuBois, Boyd, or Mosteller) used to calculate the patient's BSA, as selected from the body surface area formula selection module 300 of tabbed display page 112. Data output field 356 has a weight classification field for outputting a weight characterization (i.e., underweight, normal, overweight, obese), which is selected by processor 30 based on the BMI calculated by the processor 30 and a generally employed weight characterization paradigm.

Figure 23B:
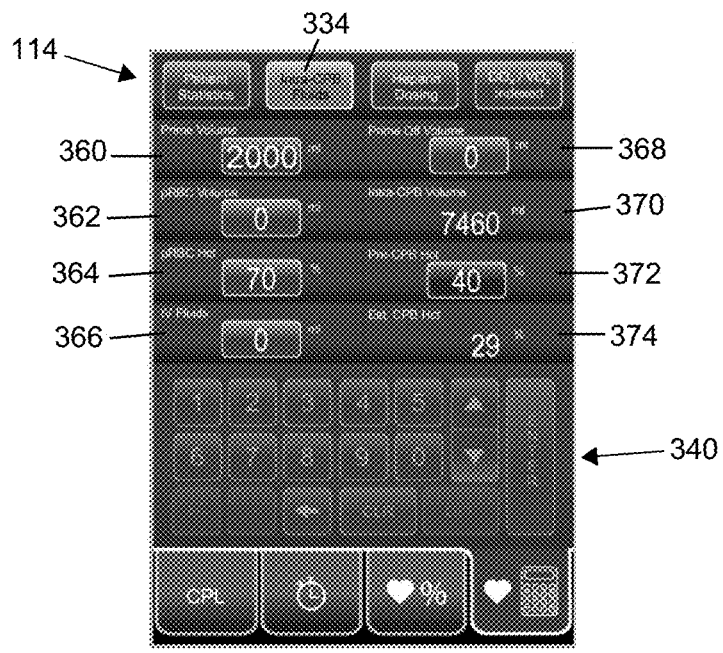

When the "Intra-CPB Fluids" button 334 has been touch or pressure activated, tabbed display page 114 displays an intra-CPB fluids data input user interface, as shown by FIG. 23b, which has data input fields 360, 362, 364, 366, 368, 372 and data output fields 370 and 374. Keypad 340 is used to enter data into the data input fields. Data input field 360 has a prime volume data field for entering the priming volume required to prime the cardiopulmonary bypass system 2. Data input field 362 has a pRBC volume data field for entering the volume of packed red blood cells (pRBCs) transfused into the patient during the CPB procedure. Data input field 364 has a pRBC Hct data field for entering the hematocrit (Hct) of pRBCs at the medical facility where the CPB procedure is performed. Data input field 366 has an IV fluids data field for entering the volume of intravenous fluids (i.e., crystalloids, saline, platelets, fresh frozen plasma, etc.) infused into the patient up to that point in time during the CPB procedure. Data input field 368 has a prime off volume data field for entering the prime off volume removed from the extracorporeal blood flow circuit 3 at the start of the CPB procedure. Data output field 370 has an intra-CPB volume data field for displaying the patient's intra-CPB volume, which is calculated by the processor 30 using the inputted data from data input fields 360, 362, 364, 366, 368 using known formulas, such as disclosed in U.S. Provisional Patent Application No. 62/160,689, filed on May 13, 2015, and its corresponding U.S. Patent Application Publication No. US XXXX/YYYYYYY, both of which are incorporated herein by reference. Data input field 372 has a pre-CPB-Hct data field for entering the patient's Hct as measured before beginning the CPB procedure. Data output field 374 has an estimated CPB Hct data field for displaying the estimated hematocrit of the patient during the CPB procedure, which is calculated by the processor 30 using entered data according to known formulas. See, e.g., U.S. Provisional Patent Application No. 62/160,689, filed on May 13, 2015, and its corresponding U.S. Patent Application Publication No. US XXXX/YYYYYYY.

Figure 23C:
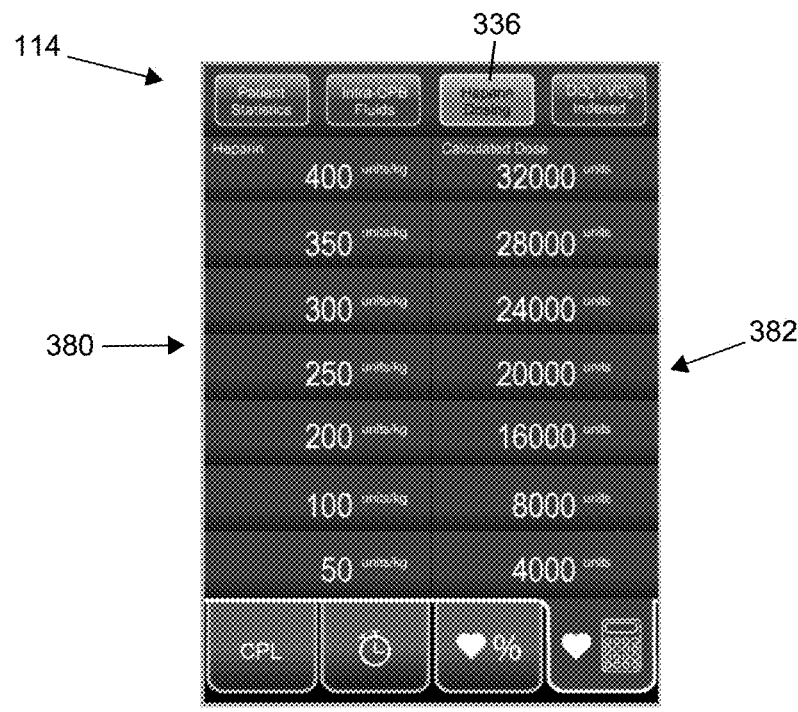

When the "Heparin Dosing" button 336 has been touch or pressure activated, tabbed display page 114 displays a heparin dosing table, as shown by FIG. 23c, which has a heparin dose per weight column 380 and a heparin calculated dose column 382, which is calculated by processor 30 and auto-populated with calculated heparin doses based on the data displayed by column 380 and the patient's weight inputted into data field 308 of tabbed display page 112. As evident from columns 380 and 382, each row pairs the heparin dose per weight from column 380 with its calculated heparin dose from column 382. For example, for a patient weighing 80 kg, the calculated dose of heparin of 24000 units corresponds to a dose of 300 units/kg.

Figure 23D:
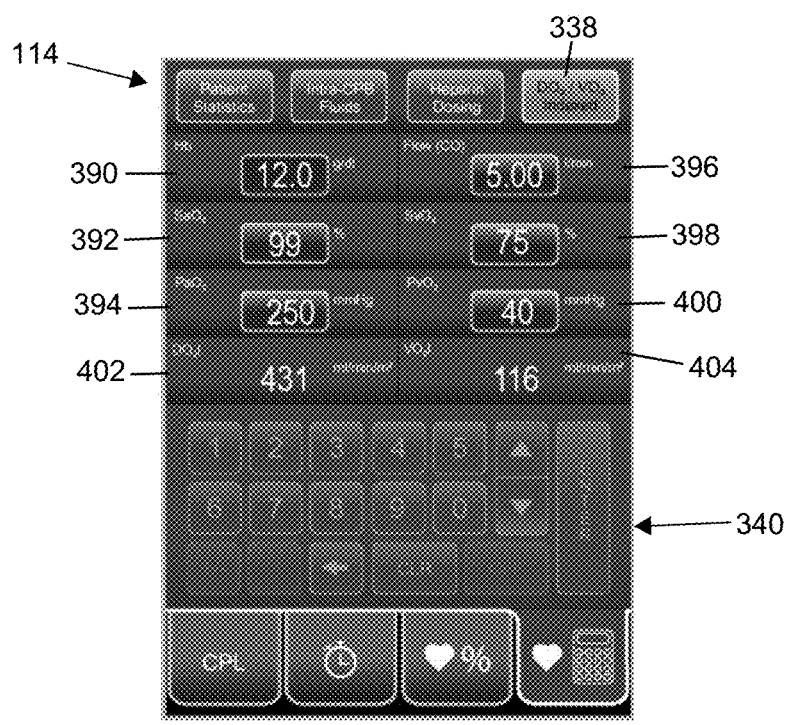

When the "$DO_2$/$VO_2$ indexed" button 338 has been touch or pressure activated, tabbed display page 114 displays a clinical data input user interface, as shown by FIG. 23d, which has data input fields 390, 392, 394, 396, 398, 400 and data output fields 402 and 404. Keypad 340 is used to enter data into the data input fields. Data input field 390 has a hemoglobin (Hb) data field for entering the patient's hemoglobin data. Data input field 392 has an arterial blood oxygen saturation ($SaO_2$) data field for entering the patient's arterial blood oxygen saturation data. Data input field 394 has an arterial partial pressure oxygen ($PaO_2$) data field for inputting the patient's arterial partial pressure of oxygen data. Data input field 396 has a pump flow data field for inputting pump flow (CO) data from the extracorporeal blood flow circuit 3. Data input field 398 has a venous blood oxygen saturation ($SvO_2$) data field for entering the patient's venous blood oxygen saturation data. Data input field 400 has a venous partial pressure oxygen ($PvO_2$) data field for inputting the patient's venous partial pressure of oxygen data. Data output field 402 has an indexed delivered oxygen ($DO_2I$) data field for displaying an indexed delivered oxygen (DO2I) value calculated by the processor 30 using data inputted into input data fields 390, 392, 394, 396, 398, 400 in accordance with known formulas. Data output field 404 has an indexed consumed oxygen ($VO_2I$) data field for displaying an indexed oxygen consumption (VO2I) value calculated by the processor 30 using data inputted into input data fields 390, 392, 394, 396, 398, 400 in accordance with known formulas.

Non-Limiting Illustrative Tabbed Display Page Patient Monitor Configuration

Figure 24:
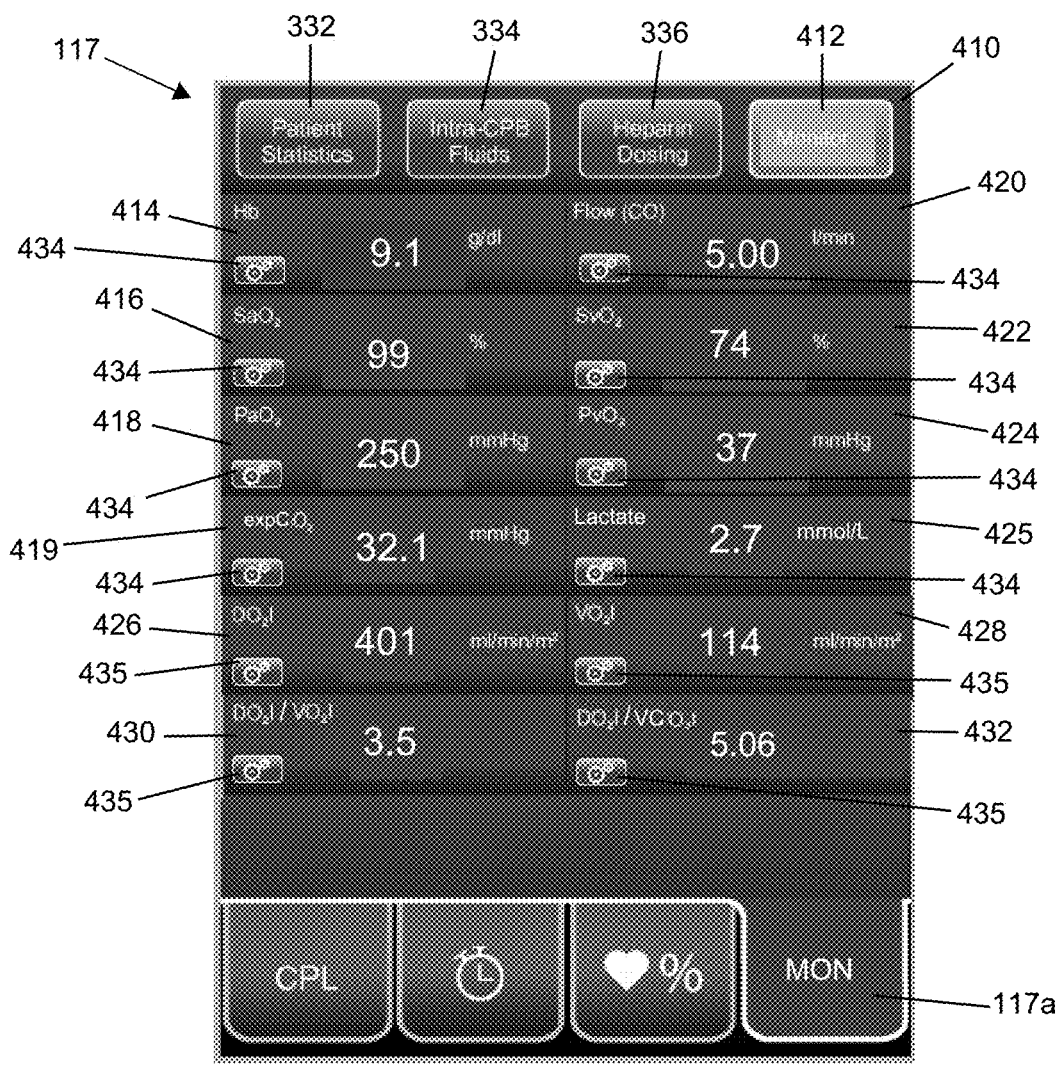
FIG. 24 illustrates an exemplary, non-limiting example of a tabbed display page directed to a patient monitor user interface in accordance with an embodiment of this disclosure.

In accordance with an embodiment of this disclosure, tabbed display page 117 may be substituted for tabbed display page 114. Tabbed display page 117, as shown in FIG. 24, includes a perfusion parameter selection module 410 that has four touch or pressure sensitive selection buttons 332, 334, 336, 412, respectively, for selecting modules that allow the user to input patient parameters, calculate intra-cardiopulmonary fluids (intra-CPB), calculate out heparin dosing for the patient, or monitor clinical parameters useful when monitoring a patient. Touch or pressure sensitive selection buttons 332, 334 and 336 activate substantially the same user interfaces illustrated by FIGS. 23a, 23b, and 23c, respectively, except that monitor button 412 is substituted for the "$DO_2/VO_2$ indexed" button 338 and activates a substantially different user interface. Tabbed display page 117 has its own unique tab 117a. Tabbed display page 117 has a non-nested sub-layered structure that is provided by the touch or pressure sensitive selection buttons 332, 334, 336, 412.

When the "Monitor" button 412 has been touch or pressure activated, tabbed display page 117 displays a clinical parameter monitoring interface, as shown by FIG. 24, which has data output fields 414, 416, 418, 419, 420, 422, 424, 425, 426, 428, 430, 432. Data output fields 414, 416, 418, 420, 422 and 424 constitute sensor output fields, and include a field settings menu button 434, which is used to link each field to an appropriate data sensor, and which may be used to set alarms (i.e., high priority alarm, medium priority alarm, low priority alarm) in a manner similar for module settings menu buttons 124. Data output fields 426, 428, 430 and 432 constitute calculated output fields, and include field settings menu buttons 435 for setting alarms, such as one or more alarms selected from the group consisting of a high priority alarm, a medium priority alarm, and a low priority alarm.

For example, data output field 414 has a hemoglobin (Hb) data field for displaying the patient's hemoglobin data derived from HCT sensor 95 in a continuous manner. In another embodiment of this disclosure, data output field 414 may display hematocrit data in a hematocrit data field instead of hemoglobin data in a hemoglobin data field, or the sensor may be a hemoglobin sensor. Because hemoglobin and hematocrit are generally related by the relationship Hct=3·(Hb), hemoglobin and hematocrit are considered equivalent and interchangeable for the purposes of this disclosure. When the field settings menu button 434 of field 414 is touch or pressure activated, a field settings menu is activated and made viewable so that a user may link the HCT sensor 95 to the field 414 in order to display measured Hb data or HCT data in the field 414, and so that a user may set any desired Hb/HCT high, medium and/or low priority alarm(s) for the field 414. The graphical display of the Hb/HCT high, medium and low priority alarms may mimic the color scheme and configurations employed for the temperature sensor modules 182 or the flow sensor modules 192.

Data output field 416 has an arterial blood oxygen saturation ($SaO_2$) data field for displaying the patient's arterial blood oxygen saturation data derived from arterial blood gas sensor assembly 94 that measures $SaO_2$ in a continuous manner. When the field settings menu button 434 of field 416 is touch or pressure activated, a field settings menu is activated and made viewable so that a user may link the arterial blood gas sensor assembly 94 to the field 416 in order to display $SaO_2$ data in the field 416, and so that a user may set any desired $SaO_2$ high, medium and/or low priority alarm(s) for the field 416.

Data output field 418 has an arterial partial pressure oxygen ($PaO_2$) data field for displaying the patient's arterial partial pressure of oxygen data that is derived from arterial blood gas sensor assembly 94 that measures $PaO_2$ in a continuous manner. When the field settings menu button 434 of field 418 is touch or pressure activated, a field settings menu is activated and made viewable so that a user may link the arterial blood gas sensor assembly 94 to the field 418 in order to display $PaO_2$ data in the field 418, and so that a user may set any desired $PaO_2$ high, medium and/or low priority alarm(s) for the field 418.

Data output field 419 has an expiratory $CO_2$ ($expCO_2$) data field for displaying the patient's expired partial pressure of carbon dioxide data that is derived from capnograph 96 that measures $expCO_2$ in a continuous manner. When the field settings menu button 434 of field 419 is touch or pressure activated, a field settings menu is activated and made viewable so that a user may link the capnograph 96 to the field 419 in order to display $expCO_2$ data in the field 419, and so that a user may set any desired $expCO_2$ high, medium and/or low priority alarm(s) for the field 419.

Data output field 420 has a pump flow data field for inputting pump flow (CO) data from the extracorporeal blood flow circuit as obtained by the pumped blood flow sensor 90 in a continuous manner. When the field settings menu button 434 of field 420 is touch or pressure activated, a field settings menu is activated and made viewable so that a user may link the blood flow sensor 90 to the field 420 in order to display blood fluid flow data in the field 420, and so that a user may set any desired blood fluid flow high, medium and/or low priority alarm(s) for the field 420.

Data output field 422 has a venous blood oxygen saturation ($SvO_2$) data field for displaying the patient's venous blood oxygen saturation data derived from venous blood gas sensor assembly 92 that measures $SvO_2$ in a continuous manner. When the field settings menu button 434 of field 422 is touch or pressure activated, a field settings menu is activated and made viewable so that a user may link the venous blood gas sensor assembly 92 to the field 422 in order to display $SvO_2$ data in the field 422, and so that a user may set any desired $SvO_2$ high, medium and/or low priority alarm(s) for the field 422.

Data output field 424 has a venous partial pressure oxygen ($PvO_2$) data field for displaying the patient's venous partial pressure of oxygen data derived from venous blood gas sensor assembly 92 that measures $PvO_2$ in a continuous manner. When the field settings menu button 434 of field 424 is touch or pressure activated, a field settings menu is activated and made viewable so that a user may link the venous blood gas sensor assembly 92 to the field 424 in order to display $PvO_2$ data in the field 424, and so that a user may set any desired $PvO_2$ high, medium and/or low priority alarm(s) for the field 424.

Data output field 425 has a blood lactate data field for displaying the patient's blood lactate data derived from an in-line blood lactate sensor 99 that measures blood lactate level in a continuous manner. When the field settings menu button 434 of field 425 is touch or pressure activated, a field settings menu is activated and made viewable so that a user may link the blood lactate sensor 99 to the field 425 in order to display blood lactate data in the field 425, and so that a user may set any desired blood lactate high, medium and/or low priority alarm(s) for the field 425.

Data output field 426 has an indexed delivered oxygen ($DO_2I$) data field for displaying an indexed delivered oxygen (DO2I) value calculated by the processor 30 using data inputted from HCT sensor 95, pumped blood flow sensor 90, and the arterial blood gas sensor assembly 94, and the patient's BSA calculated from data input via tabbed display page 112, in accordance with known formulas. When the field settings menu button 435 of field 426 is touch or pressure activated, a field settings menu is activated and made viewable so that a user may set desired $DO_2I$ high, medium and/or low priority alarm(s) for the field 426.

Data output field 428 has an indexed consumed oxygen ($VO_2I$) data field for displaying an indexed oxygen consumption (VO2I) value calculated by the processor 30 using data inputted from HCT sensor 95, pumped blood flow sensor 90, arterial blood gas sensor assembly 92 and the venous blood gas sensor assembly 94, and the patient's BSA calculated from data input via tabbed display page 112, in accordance with known formulas. When the field settings menu button 435 of field 428 is touch or pressure activated, a field settings menu is activated and made viewable so that a user may set desired $VO_2I$ high, medium and/or low priority alarm(s) for the field 426.

Data output field 430 has an ($DO_2I$)/($VO_2I$) ratio data field for displaying a ratio of indexed oxygen delivery ($DO_2I$) to indexed oxygen consumption (VO2I) value that is calculated by the processor 30 in accordance with known formulas. When the field settings menu button 435 of field 430 is touch or pressure activated, a field settings menu is activated and made viewable so that a user may set desired ($DO_2I$)/($VO_2I$) ratio high, medium and/or low priority alarm(s) for the field 430.

Data output field 432 has an ($DO_2I$)/($VCO_2I$) ratio data field for displaying a ratio of indexed oxygen delivery ($DO_2I$) to indexed carbon dioxide production (VCO2I) value that is calculated by the processor 30 in accordance with known formulas using data input from HCT sensor 95, pumped blood flow sensor 90, arterial blood gas sensor assembly 92, and capnograph 96. When the field settings menu button 435 of field 432 is touch or pressure activated, a field settings menu is activated and made viewable so that a user may set desired ($DO_2I$)/($VCO_2I$) ratio high, medium and/or low priority alarm(s) for the field 432.

In accordance with an embodiment of this disclosure, an untabbed display page with the same patient monitoring configuration as the tabbed display page 117 may be implemented in place of the tabbed display page 117. In this embodiment, the untabbed display page is provided with a patient monitoring configuration possessing substantially the same data output fields and functionalities of the tabbed display page 117 except that it has no tabs and is continuously displayed in its own section 108. In such an embodiment, this untabbed patient monitoring display page provides a continuous patient monitoring display page that is displayed continuously in addition to the untabbed display page 115 so that the central monitoring portion 106 is provided with two untabbed display pages, each within its own section 108, with the remaining sections 108 of the central monitoring portion 106 each provided with one or more tabbed display pages. In accordance with another embodiment of this disclosure, one section 108 of the central monitoring portion 106 is provided with a single untabbed display page, namely, the untabbed patient monitoring display page, and the remaining sections 108 of the central monitoring portion 106 are populated with one or more tabbed display pages (preferably from one to four tabbed display pages per section).

Non-Limiting Illustrative Tabbed Display Page Configurations for Additional Sensors Tabbed display page 116 of section 108d and tabbed display page 122 of section 108c constitute sensor pages through which various additional sensors desired by a user are linked to the graphical user interface 100, and thereby monitorable by a user. Thus, any additional pressure sensor modules, bubble detection sensor modules, level sensor modules, temperature sensor modules, flow sensor modules, pressure delta sensor modules, and the like, may be configured in any order in such additional sensor pages of sections 108c and 108d. The examples shown in FIGS. 3a and 3b are merely exemplary and are not to be construed as limiting examples and/or preferred examples.

Figure 25A:
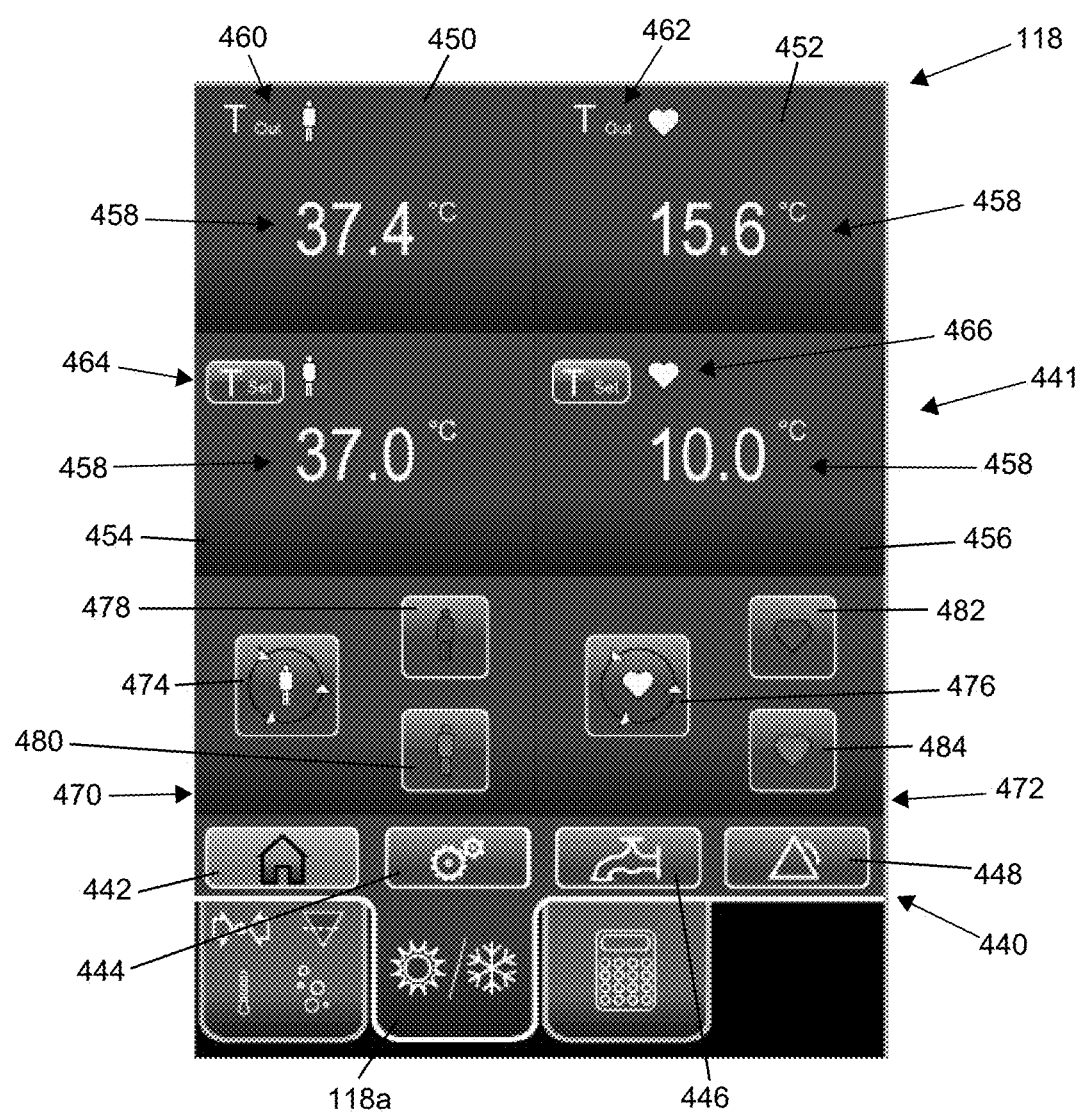
FIGS. 25a, 25b, 25c and 25d (which may be collectively referred to as "FIG. 25") illustrate an exemplary, non-limiting embodiment of a tabbed display page directed to a remote control heater-cooler unit user interface in accordance with an embodiment of this disclosure.
Figure 25B:
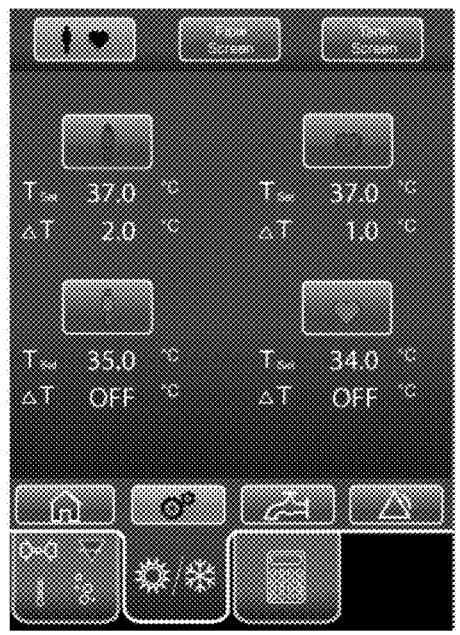
Figure 25C:
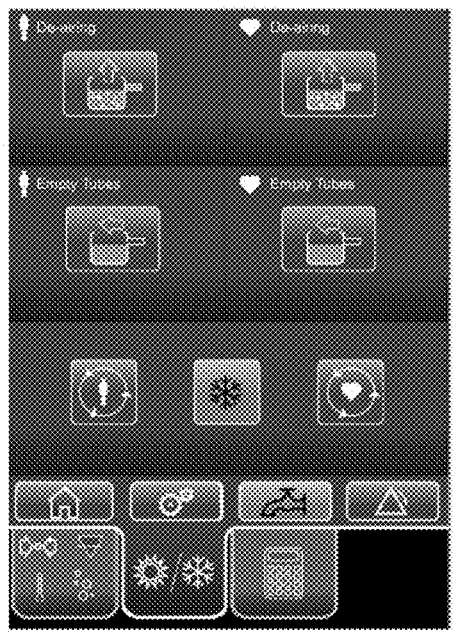
Figure 25D:

Non-Limiting Illustrative Tabbed Display Page Configuration for Remote Control of a Heater/Cooler Unit Tabbed display page 118, such as may be located in section 108c or section 108d, constitutes a heater/cooler remote control user interface, such as may be used to remotely control heating-cooling of the patient using a heater-cooler unit 85 during a cardiopulmonary bypass procedure and/or to remotely control heating-cooling during cardioplegia. As shown in FIG. 25a, tabbed display page 118 includes a screen selection module 440 that is used to select a configuration for screen 441 of the tabbed display page 118. The screen selection module 440 includes home button 442, a screen settings button 444, a heater-cooler unit functions button 446, and a heater-cooler unit alarms button 448, which are all touch or pressure activated. Activation of the home button 442 results in display of the screen configuration according to FIG. 25a. Activation of the screen settings button 444 results in display of the screen configuration according to FIG. 25b, which is used to set temperature parameters such as temperature set points for the patient's body and for cardioplegia and temperature gradients used in warming and/or cooling. Activation of the heater-cooler unit functions button 446 results in display of the screen configuration according to FIG. 25c, which is used to manage operation of a compressor of the heater-cooler unit 85, and to initiate de-airing of patient and/or cardioplegia heating-cooling circuits, and to initiate emptying of tubes of patient and/or cardioplegia heating-cooling circuits. Activation of the heater-cooler alarms button 448 results in display of the screen configuration according to FIG. 25d, which is used to review messages pertaining to any alarm state related to the heater-cooler unit 85. As evident from FIGS. 25a and 25d, the icon and/or color scheme of the heater-cooler unit alarms button 444 may switch from a normal state (i.e., no alarm) to a high priority alarm state (i.e., an alarm with three exclamation points), thereby placing a user on notice to activate the heater-cooler unit alarms button 444 in order to view additional information pertaining to the alarm state.

The screen of FIG. 25a is described in more detail as follows. The screen according to FIG. 25a includes heater-cooler temperature modules 450, 452, 454 and 456. Each of these temperature modules includes a temperature value field 458 for displaying temperature data obtained by a temperature sensor. Temperature module 450 includes a title field 460 that includes the term "$T_{Out}$" associated with a patient icon, which indicates that this module displays the actual output temperature for the patient circuit of the heater-cooler unit 85. Temperature module 452 includes a title field 462 that includes the term "$T_{Out}$" associated with a heart icon, which indicates that this module displays the actual output temperature for the cardioplegia circuit of the heater-cooler unit 85. Temperature module 454 includes a "$T_{set}$" button 464 that is associated with a patient icon, which indicates that this button 464 activates with touch or pressure a menu screen for setting a set temperature for the patient circuit of the heater-cooler unit 85. Temperature module 456 includes a "$T_{set}$" button 466 that is associated with a heart icon, which indicates that this button 466 activates, following touch or pressure, a menu screen for setting a set temperature for the cardioplegia circuit of the heater-cooler unit 85.

The screen of FIG. 25*a* also includes a patient circuit module 470 and a cardioplegia circuit module. The patient circuit module 470 includes a patient circuit control button 474 that is used to select from multiple patient circuit control states. The patient circuit module 470 further includes a patient warming button 478 and a patient cooling button 480. When activated by touch or pressure, the patient warming button 478 causes the display of a screen used to confirm or cancel the patient warming temperature set point and the patient warming temperature gradient. When activated by touch or pressure, the patient cooling button 480 causes the display of a screen used to confirm or cancel the patient cooling temperature set point and the patient cooling temperature gradient.

The cardioplegia circuit module 472 includes a cardioplegia circuit control button 476 that is used to select from multiple cardioplegia circuit control states. The cardioplegia circuit module 472 further includes a cardioplegia warming button 482 and a cardioplegia cooling button 484. When activated by touch or pressure, the cardioplegia warming button 482 causes the display of a screen used to confirm or cancel the cardioplegia warming temperature set point and the cardioplegia warming temperature gradient. When activated by touch or pressure, the cardioplegia cooling button 484 causes the display of a screen used to confirm or cancel the cardioplegia cooling temperature set point and the cardioplegia cooling temperature gradient.

Figure 26:
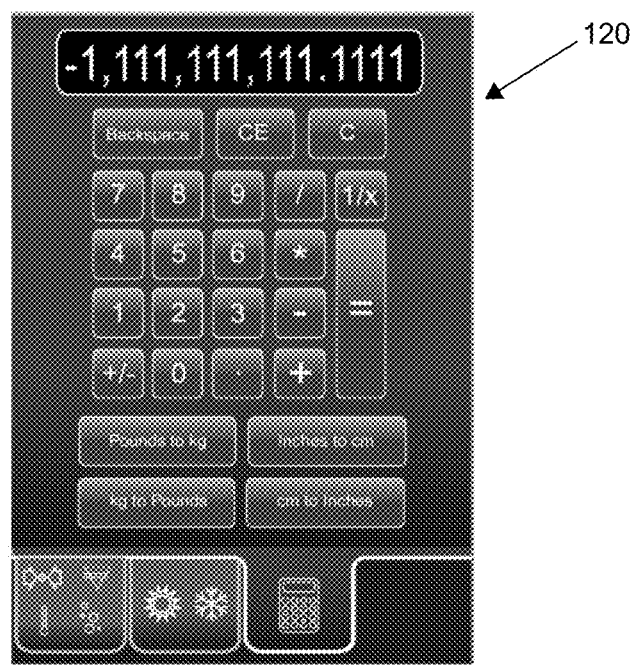
FIG. 26 illustrates an exemplary, non-limiting embodiment of a tabbed display page directed to a general use calculator in accordance with an embodiment of this disclosure.

Non-Limiting Illustrative Tabbed Display Page Configuration for General Use Calculator Tabbed display page 120, as shown in FIG. 26, is configured as a general use calculator provided with standard arithmetic functions such as addition, subtraction, multiplication, division, and an inverse function. The general use calculator is also provided with several unit conversion functions such as pounds to kilograms, kilograms to pounds, inches to centimeters, and centimeters to inches.

Figure 27:
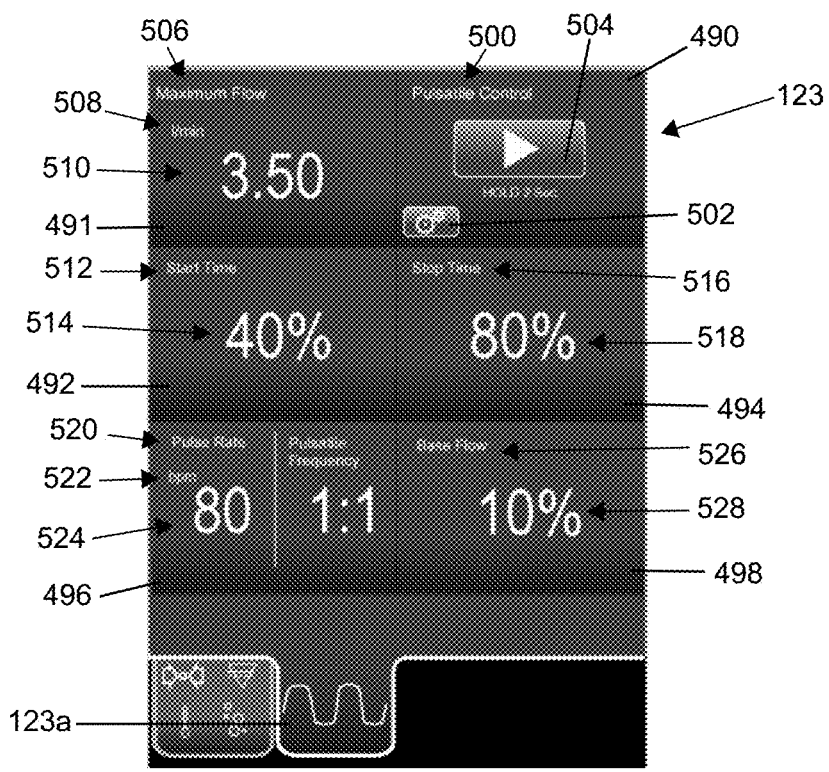
FIG. 27 illustrates an exemplary, non-limiting embodiment of a tabbed display page directed to a pulsatile control user interface for an arterial pump in accordance with an embodiment of this disclosure.

Non-Limiting Illustrative Tabbed Display Page Configuration for Pulsatile Control of Blood Flow Tabbed display page 123 is illustrated in FIG. 27, and pertains to a pulsatile control user interface in accordance with an embodiment of this disclosure, such as is used to control the pulsatile character of blood fluid flowing through the extracorporeal blood flow circuit 3 when an arterial pump 38 is operating in the circuit 3. Such pulsatile control advantageously provides pulsatile blood flow in the extracorporeal blood flow circuit 3 that is more physiologic and, therefore, may produce perfusion advantages not achievable by non-pulsatile flow.

Tabbed display page 123 includes a pulsatile control module 490, a maximum flow module 491, a start time module 492, a stop time module 494, a pulse rate and frequency module 496, and a base flow module 498. The pulsatile control module 490 includes a fixed title field 500, a pulsatile delivery settings menu button 502, and a pulsatile control button 504. Activation of the pulsatile delivery settings menu button 502 by touch or pressure causes a pulsatile delivery settings menu screen to become visible, which constitutes a graphical user interface screen for entering control parameters that are displayed in the other modules 491, 492, 494, 496 and 498 of the tabbed display page 123. Activation of the pulsatile control button 504 by continuous touch or pressure for at least two seconds causes the arterial pump 38 operably linked to tabbed display page 123 to operate in a pulsatile flow mode having characteristics as defined as follows.

The maximum flow module 491 includes a fixed maximum flow title field 506, a fixed units field 508, and a maximum flow value field 510. The maximum flow value field 510 displays the maximum flow value achievable for the pulsatile flow as set using the pulsatile delivery settings menu.

The start time module 492 includes a fixed start time title field 512 and a start time value field 514, which displays the time it takes for pump pressure to reach its maximum during a pump cycle as a percentage of a cardiac cycle. The stop time module 494 includes a fixed stop time title field 516 and a stop time value field 518, which displays the time it takes for pump pressure to reach its baseline minimum during a pump cycle as a percentage of a cardiac cycle.

The pulse rate and frequency module 496 includes a fixed title field 520 for the pulse rate and the pulsatile frequency, and a fixed units field 522, and pulse rate and pulsatile value field 524 that displays the pulse rate of the pump 38 in beats per minute (bpm) and ratio of pump cycle to cardiac cycle. In this case, the displayed 1:1 ratio means that there is one pump cycle per cardiac cycle.

The base flow module 498 includes a fixed base flow title field 526 and a base flow value field 528, which displays the base flow as a percentage of the target flow of the arterial pump 38. The target flow of the arterial pump 38 is displayed elsewhere as part of another portion 24 of the user interface system 20.

Figure 28:
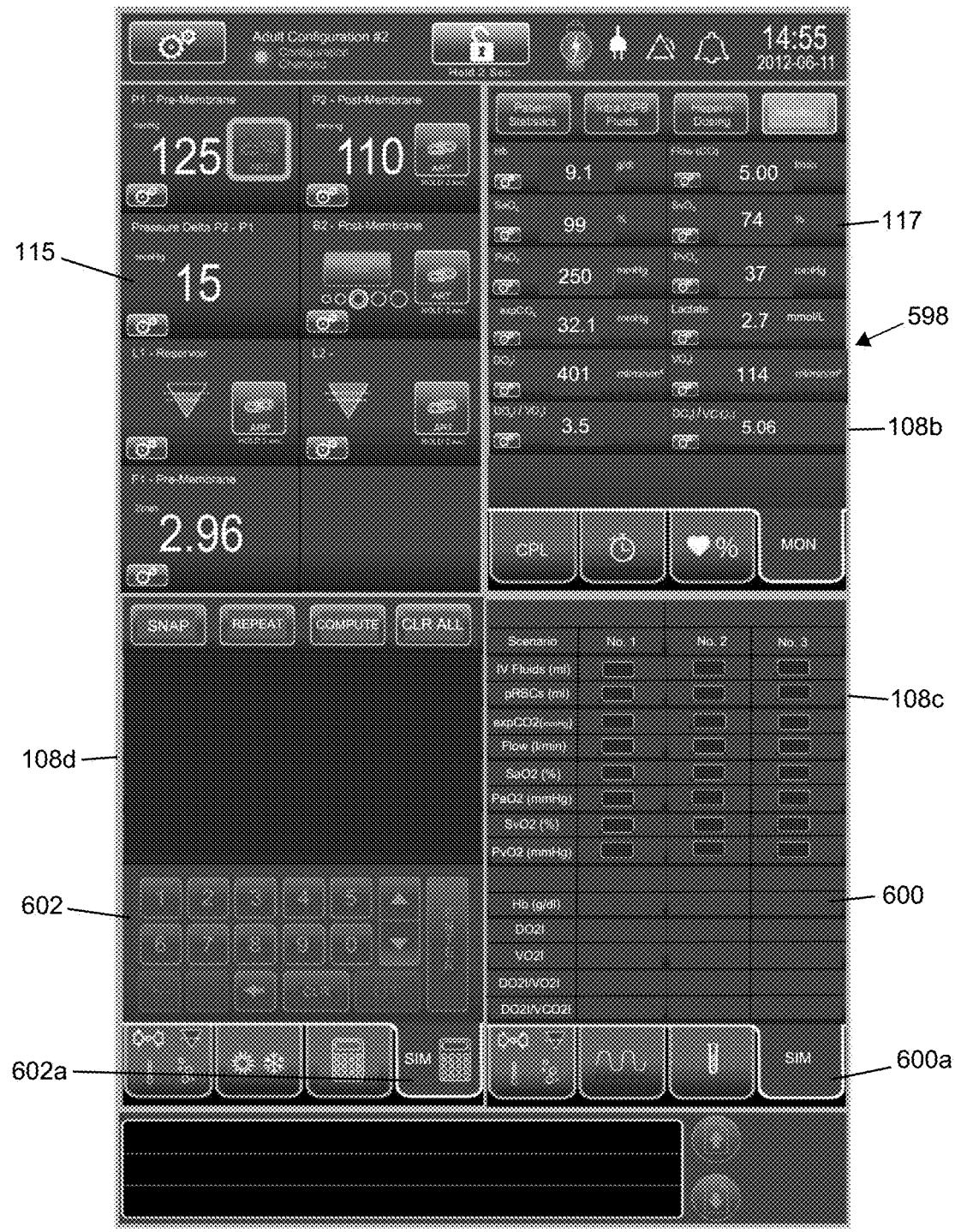
FIG. 28 illustrates an exemplary, non-limiting embodiment of a clinical parameter monitor-simulation user interface in accordance with an embodiment of this disclosure.

Non-Limiting Illustrative Tabbed Display Page Configurations for Clinical Parameter Monitor-Simulator In accordance with an embodiment of this disclosure, the graphical user interface 100 may include a clinical parameter monitor-simulator user interface 598. The clinical parameter monitor-simulator user interface 598 is formed by the combined simultaneous display of tabbed display pages 117, 600 and 602, which occurs when a user touch or pressure activates tabs 117*a*, 600*a* and 602*a* concurrently so that tabbed display pages 117, 600 and 602 are in the display mode together as shown in FIG. 28. In other words, such as shown by FIG. 28, when tabbed display pages 117, 600 and 602 are displayed simultaneously in three different sections 108, such as, for example, sections 108*b*, 108*c*, and 108*d*, respectively, these three tabbed display pages are operable together to form a unified clinical parameter monitor-simulator graphical interface. In accordance with this disclosure, such a themed user interface formed by three operably connected tabbed display pages may be characterized as a triplet pair of tabbed display pages. In accordance with other embodiments of this disclosure, a themed user interface formed by two operably connected tabbed display pages that are displayed together may be characterized as a doublet pair of tabbed display pages.

Tabbed display page 117 is described above and displays a patient monitor configuration when touch or pressure sensitive monitor button 412 has been activated (See FIG. 24). Tabbed display page 600 constitutes a simulator page and tabbed display page 602 constitutes a simulator keypad page, which together provide a graphical user interface for entering and manipulating clinical data for a clinical simulator in order to test out multiple hypothetical clinical scenarios in real time and in situ based on the patient's actual clinical data. Thus, the unified clinical parameter monitor-simulator graphical interface is operable to provide clinicians with timely guidance with respect to managing a patient during a cardiopulmonary bypass procedure, for example.

Figure 29:
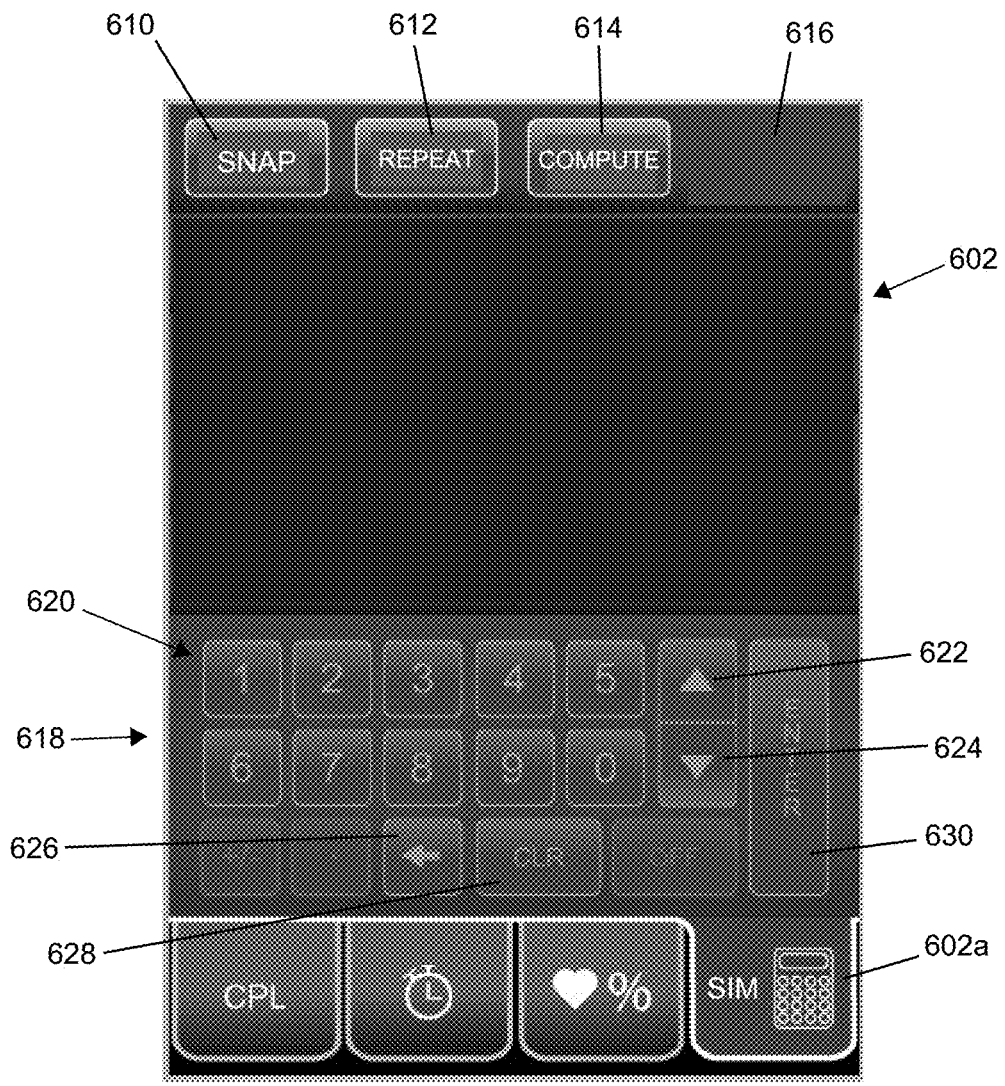
FIG. 29 illustrates an exemplary, non-limiting embodiment of a tabbed display page directed to a simulator keypad page of a clinical parameter monitor-simulation user interface in accordance with an embodiment of this disclosure.

As shown in FIG. 29, the tabbed display page 602 includes a tab 602a that is touch or pressure sensitive. Activation of tab 602a by touch or pressure results in display of tabbed display page 602 in the display mode, and the rest of the tabbed display pages of the corresponding section are then displayed in the overlaid mode. Tabbed display page 602 includes a snap button 610, a repeat button 612, a compute button 614, a clear all button 616, and a keypad 618, all of which are touch or pressure activated on the touch screen 17. The snap button is operable by touch or pressure to effect a transfer of monitored patient data displayed by the patient monitor of the tabbed display page 117 to a data field array of a simulator screen of the tabbed display page 600. The repeat button 612 is operable by touch or pressure to effect a duplicate transfer of monitored patient data into a second or third data field array of the simulator screen. The compute button 614 is operable by touch or pressure to effect one or more computations based on patient data in one, two or three data field arrays of the tabbed display page 600. The clear all button is operable by touch or pressure, preferably with a two second hold required, to effect clearing of all the monitored patient data displayed by the data field arrays of the simulator screen as well as clearing of all calculated clinical parameters contained in computation field arrays of the simulator screen.

The keypad 618 includes a plurality of numerical and punctuation keys 620, such as are known keypad components, as well as an up arrow key 622, a down arrow key 624, a backspace key 626, a clear key 628 and an enter key 630. The various keys are used to manipulate data in one or more data field arrays of a simulator screen of tabbed display page 600. The up arrow key 622 and down arrow key 624 are used to move a cursor up and down a data field array. The backspace key 626 is used to delete entries in a data field one number at a time, whereas the clear key 628 is used to clear all of the data in a single data field. The enter key 630 may be used to move a cursor from one data field array to another data field array.

FIG. 30a illustrates a tabbed display page 600, which includes a touch or pressure activated tab 600a, which causes tabbed display page 600 to be displayed in its quadrant when tab 600a has been activated by touch or pressure. Tabbed display page 600 constitutes a simulator screen that includes three clinical data field arrays 640, 642, 644, and corresponding three computed data field arrays 650, 652, 654, respectively, which together are labeled as Scenario Nos. 1, 2 and 3, respectively. Each clinical data field array includes a plurality of data entry fields, which are data fields into which clinical data values are entered and selectively manipulated using the keypad 618 of the tabbed display page 602. Data entry fields, such as form the data field arrays 640, 642, 644, may include IV fluids data entry field 646 into which IV fluids volume data is input, pRBCs data entry field 648 into which the volume of transfused pRBC's is input, expCO2 data entry field 670 into which patient expired carbon dioxide data is input, flow data entry field 672 into which blood flow data from a pump and/or of the extracorporeal blood flow circuit is input, $SaO_2$ data entry field 674 into which patient arterial oxygen saturation data is input, $PaO_2$ data entry field 676 into which patient arterial oxygen tension data is input, $SvO_2$ data entry field 678 into which patient venous oxygen saturation data is input, and $PvO_2$ data entry field 680 into which patient venous oxygen tension data is input.

By pressing the snap button 610 of tabbed display page 602, patient clinical data values displayed by corresponding data fields from tabbed display page 117 (FIG. 24) and/or tabbed display page 114 (FIG. 23b) are used to instantaneously autopopulate the data entry fields of the first clinical data field array 640. This is the case as illustrated by FIG. 30a, which shows the first clinical data field array 640 populated with patient clinical data values, having been autopopulated when the snap button 610 was activated at some time $t_0$. If a user were to subsequently press the snap button 610 again at some later time $t_1$, then the second clinical data field array 642 would be autopopulated with patient clinical values from the corresponding data fields of tabbed display pages 114, 117, but at the later time $t_1$. If a user were to subsequently press the snap button again at some later time $t_2$, then the third clinical data field array 644 would be autopopulated with patient clinical values from the corresponding data fields of tabbed displayed pages 114, 117, but corresponding to the even later time $t_2$. Once the three clinical data field arrays 640, 642, 644 are populated with data, the activation of the snap button 610 will have no effect until the data in the clinical data field arrays 640, 642, 644 has been cleared by activating the clear all button 616, for example. In an embodiment of this disclosure, touch or press activation of the clear all button 616 simultaneously stores data from the clinical data field arrays 640, 642 and 644 in a memory device associated with the processor 30 and clears the clinical data field arrays 640, 642, 644. In accordance with an embodiment of this disclosure, the memory device is a hardware device.

Each of the computed data field arrays 650, 652, 654 includes a plurality of data display fields, which are data fields that display computed clinical data values using known formulas, such as those disclosed by U.S. Provisional Patent Application No. 62/160,689, filed on May 13, 2015, and its corresponding U.S. Patent Application Publication No. US XXXX/YYYYYYYY, and/or by U.S. Patent Application Publication No. US 2006/0257283 A1, which are incorporated herein by reference in their entirety for all they disclose. Data display fields, such as form the computed data field arrays 650, 652, 644, may include computed hemoglobin data display field 655 that displays computed hemoglobin values, indexed delivered oxygen (DO2I) data display field 656 that displays computed indexed delivered oxygen values, indexed consumed oxygen (VO2I) data display field 658 that displays computed indexed consumed oxygen values, computed ratio of indexed delivered oxygen to indexed consumed oxygen data display field 660 that displays a computed ratio of indexed delivered oxygen to indexed consumed oxygen (DO2I/VO2I), and computed ratio of indexed delivered oxygen to indexed produced carbon dioxide data display field 662 that displays a computed ratio of indexed delivered oxygen to indexed produced carbon dioxide (DO2I/VCO2I).

The computed data values that will populate the data display fields of a computed data field array, such as computed data field array 650, are calculated by the processor 30 when the corresponding data field array 640 has been fully populated with data and then the compute button 614 of tabbed display page 602 has been activated by touch or pressure. The same operation described above with respect to paired clinical and computed data field arrays 640 and 650, respectively, applies to paired clinical and computed data field arrays 642 and 652, and paired clinical and computed data field arrays 644 and 654, respectively.

FIG. 30b illustrates the effect of the repeat button 612 of the tabbed display page 602. Activation of the repeat button 612, by touch or pressure, causes data in the data entry fields of the clinical data field array to the immediate left to autopopulate the data entry fields of the clinical data field array to the immediate right with the same data. Thus, when clinical data field array 640 is populated with data as shown in FIG. 30a, activation of the repeat button 612 causes the clinical data field array 642 to be populated with the same data as the clinical data field array 640 shown in FIG. 30b. If the repeat button 612 is again activated, then the empty clinical data field array 644 would be autopopulated with the same data populating the clinical data field array 642. The purpose of the repeat button 612 is to facilitate copying of the same data into more than one clinical data field array for the purposes of subsequent manipulation before computing hypothetical computed data values based on hypothetical clinical interventions in order to make possible comparison of different scenario simulations.

Activation of the repeat button 612 has no effect when the clinical data field arrays 640 and 642 are empty. Activation of the repeat button 612 also has no effect when the three clinical data field arrays are full of data.

It should be understood that when the clinical data field arrays 640, 642, 644 are empty, activation of the snap button 610 three consecutive times may result in population of the clinical data field arrays 640, 642, 644 with different information because each snapshot would occur at different times $t_0$, $t_1$, $t_2$, and because much of the data snapped is continuously monitored so it is continuously changing. On the other hand, activation of the snap button 610 followed by activating the repeat button 612 twice would result in the same data populating the clinical data field arrays 640, 642, 644.

FIG. 30c illustrates a non-limiting example of how simulation may be used to facilitate patient care using the clinical parameter monitor-simulator user interface 598. In the example, a clinician may explore how transfusing various amounts of pRBCs (e.g., 250 cc, 500 cc, or 750 cc) may affect hemoglobin levels and other clinical parameters, such as DO2I, VO2I, DO2I/VO2I, and DO2I/VCO2I, if all other parameters are held constant. In the example, the clinician employs the keypad 618 to selectively change autopopulated data entries previously provided by activating the snap button 610, or the snap button 610 and then the repeat button 612. Following entry of the simulation data, the clinician activates the compute button 614 so the computed data field arrays 650, 652, 654 are populated with computed data.

This example, which is directed to varying the amount of transfused blood, is merely exemplary, and should not be construed as limiting as other simulations may be performed that vary other parameters, such as total IV fluid administered and/or changes to carbon dioxide production (expCO2), for example. Simulations may be performed in which only one parameter is varied at a time and all other variables are held constant. Simulations may be performed in which multiple parameters are varied at a time and the remaining other variables are held constant. Simulations may also include estimates and guestimates regarding how a variable may change due to hypothesized changes in one or more other variables.

FIG. 30d illustrates a non-limiting example of simulation employing either an estimate or a guestimate. An estimate, in accordance with this disclosure, constitutes a hypothetical data point based on another calculation or based on historical data about a patient that may be used as a factual basis to generate estimated data that is used in simulation. On the other hand, a guestimate, in accordance with this disclosure, constitutes a hypothetical data point that is not based on fact per se, although it may be based on intuition. For example, if it is believed that a patient's carbon dioxide production may increase following a rise in body temperature of 10 degrees Fahrenheit during re-warming, a guestimate for simulation may include, for example, the intuitive guess that the patient's carbon dioxide production $expCO_2$ may rise by 10%. Thus, under such circumstances, the patient's $expCO_2$ may be entered into the simulator as a guestimate that is 10% higher than the previous baseline if it is planned to increase the patient's temperature 10%.

According to the simulation of FIG. 30d, clinical data field array 640 consists of snapped data, meaning autopopulated data from tabbed display pages 114 and 117 that resulted from activation of the snap button 610. Clinical data field array 642 constitutes data repeated from clinical data field array 640 using the repeat button 612, wherein some of the data fields have then been modified using the keypad 618 to include hypothetical data. More specifically, the clinical data field array 640 corresponds to a patient who has received, up to the time during a cardiopulmonary bypass procedure that the snap button 610 is activated, 250 cc IV fluids and 500 cc pRBCs, and the patient has measured values for $expCO_2$ of 32.1 mmHg, flow of 5.001/min, $SaO_2$ of 99%, $PaO_2$ of 250 mmHg, $SvO_2$ of 73%, and $PvO_2$ of 36 mmHg. According to the simulation, hypothetical data for simulation have been added for pRBCs, $SVO_2$ and $PvO_2$, which reflects another 250 cc pRBC transfusion given to the patient with estimated or guesstimated values for $SvO_2$ and $PvO_2$ of 81 and 40, respectively, based on assumptions that the transfused blood will increase the patient's $SvO_2$ and $PvO_2$. Activating the compute button 614 then results in computed data populating the computed data fields 650 and 652, which gives the clinician an idea how the planned intervention may affect the patient's clinical status based on known calculable clinical parameters, such as hemoglobin, indexed oxygen delivery (DO2I), indexed oxygen consumption (VO2I), and various ratios known or believed to have correlation with clinical outcomes. For example, the ratio DO2I/VCO2I of 5 or greater is associated with improved clinical outcomes according to M. Rannuci et al., Anaerobic Metabolism During Cardiopulmonary Bypass: Predictive Value of Carbon Dioxide Derived Parameters, 81 ANNUALS THORACIC SURGURY 2189-2195 (2006).

Figure 31:
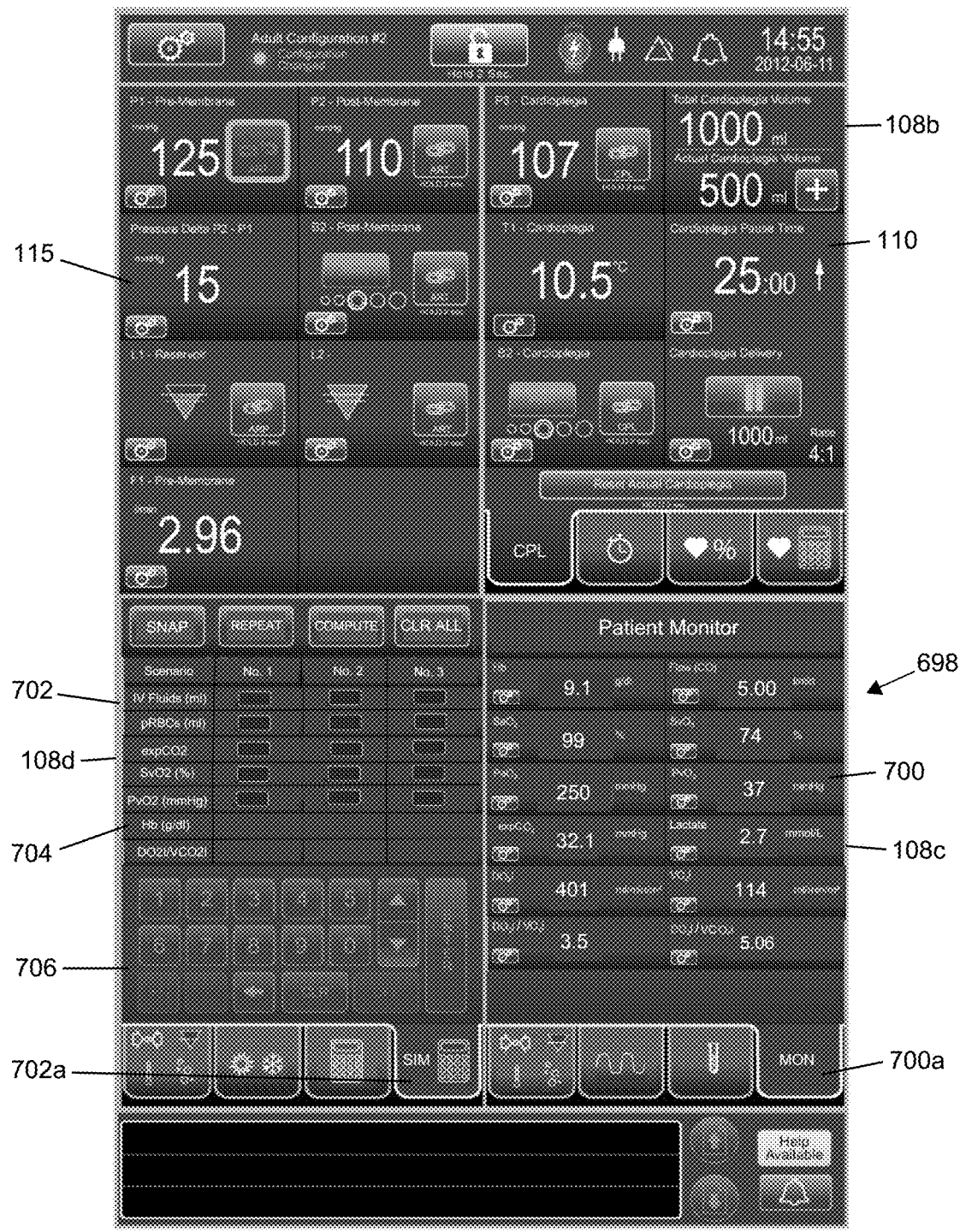
FIG. 31 illustrates an exemplary, non-limiting embodiment of a clinical parameter monitor-simulation user interface in accordance with an embodiment of this disclosure.

In accordance with an embodiment of this disclosure, the graphical user interface 100 may include a clinical parameter monitor-simulator user interface 698 that is formed by the combined simultaneous display of tabbed display pages 700 and 702, which occurs when a user touch or pressure activates tabs 700a and 702a concurrently so that tabbed display pages 700 and 702 are in the display mode together as shown in FIG. 31. In other words, such as shown by FIG. 31, when tabbed display pages 700 and 702 are displayed simultaneously in two different sections 108, such as, for example, sections 108c and 108d, respectively, these two tabbed display pages are operable together to form a unified clinical parameter monitor-simulator graphical interface 698. In accordance with this disclosure, such a themed user interface formed by two operably connected tabbed display pages may be characterized as a doublet pair of tabbed display pages. In accordance with an embodiment of this disclosure, a clinical parameter monitor-simulator user interface may be formed by a single tabbed display page (i.e., a singlet tabbed display page), which incorporates both the patient monitor and the simulator.

Tabbed display page 700 constitutes a patient monitor page and is similar to the tabbed display page 117; however, tabbed display page 700 is activatable in the display mode merely by touch or pressure activation of tab 700a. Tabbed display page 702 constitutes a simulator screen 704 and simulator keypad 706, which provides a graphical user interface for entering and manipulating clinical data for a clinical simulator in order to test out multiple hypothetical clinical scenarios in real time and in situ based on the patient's actual clinical data in order to provide clinicians with timely guidance with respect to managing a patient during a cardiopulmonary bypass procedure, for example.

Tabbed display page 702 includes a snap button, a repeat button, a compute button, a clear all button, and a keypad 706, all of which are touch or pressure activated on the touch screen 17. The snap button is operable by touch or pressure to effect a transfer of monitored patient data displayed by the patient monitor of the tabbed display page 700 to a data field array of a simulator screen 704 of the tabbed display page 702. The repeat button is operable by touch or pressure to effect a duplicate transfer of monitored patient data into a second or third data field array of the simulator screen 704. The compute button is operable by touch or pressure to effect one or more computations based on patient data in one, two or three data field arrays of the tabbed display page 702. The clear all button (CLR ALL) is operable by touch or pressure, preferably with a two second hold required, to effect clearing of all the monitored patient data displayed by the data field arrays of the simulator screen as well as clearing of all calculated clinical parameters contained in computation field arrays of the simulator screen. The operation of the simulator screen 704 and keypad 706 is substantially the same as the operation of the tabbed display pages 600 and 602. The clear all button of tabbed display page 702 may effect a save operation, wherein the data in the data field arrays are saved into a memory device associated with the processor 30 at the same time the data field arrays are cleared of data.

An advantage the doublet clinical parameter monitor-simulator user interface 698 has over the triplet clinical parameter monitor-simulator user interface 598 is that the doublet user interface 698 takes up less space than the triplet user interface 598. An advantage that the triplet user interface 598 has over the doublet user interface 698 is that the triplet user interface 598 may be used to monitor and simulate more clinical parameters than the doublet user interface 698 because it has more space for monitoring and simulation.

Figure 32:
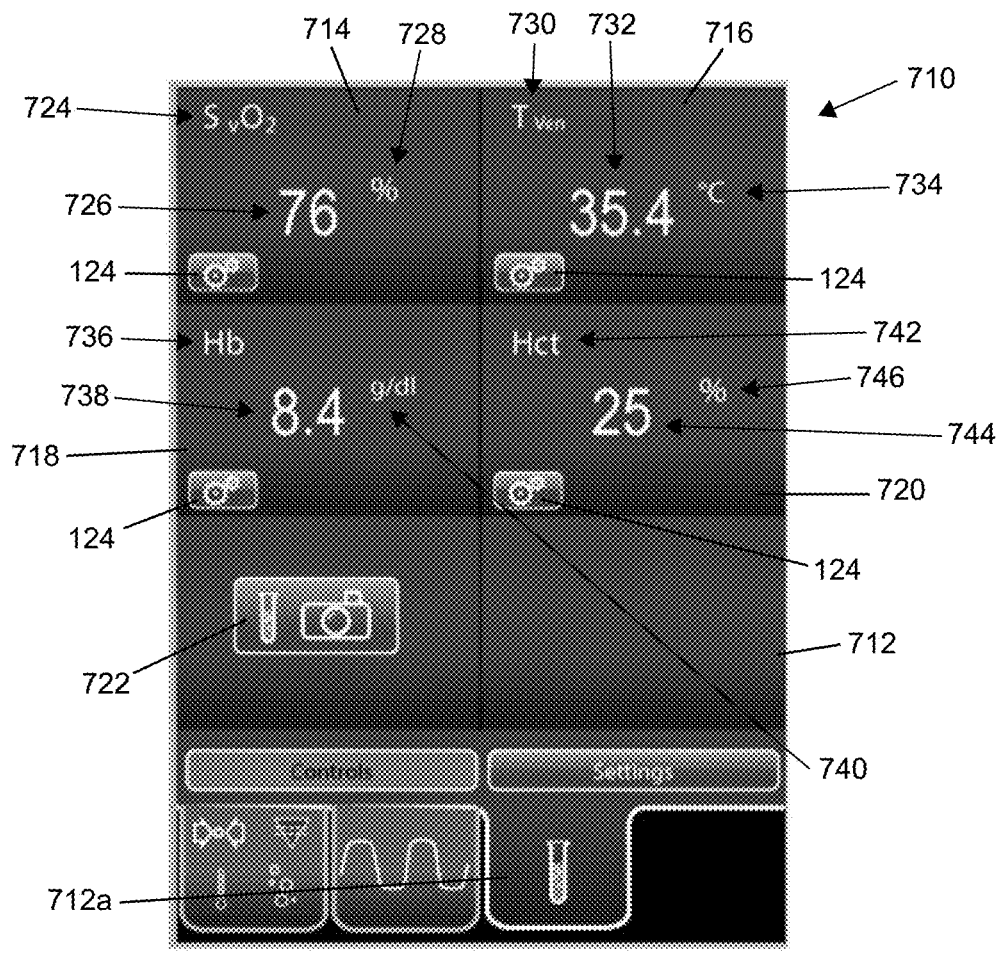
FIG. 32 illustrates an exemplary, non-limiting embodiment of a blood monitoring unit interface in accordance with an embodiment of this disclosure.
Figure 33:
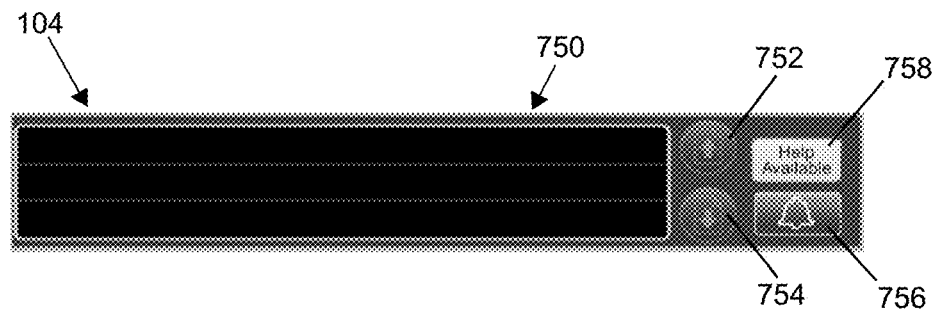
FIG. 33 illustrates an exemplary, non-limiting configuration of a footer portion of the graphical user interface of FIG. 3.

Non-Limiting Illustrative Tabbed Display Page Configuration for Interfacing with a Blood Monitoring Unit In accordance with an embodiment of this disclosure, as shown in FIG. 32, the graphical user interface 100 may include a blood monitoring user interface 710, which is a tabbed display page for interfacing with a blood monitoring unit 800, such as the Blood Monitoring Unit BMU 40 (MAQUET), which may be operably connected to the processor 30 of a cardiopulmonary bypass machine 1. A blood monitoring unit (BMU) 800 is an inline monitoring device for continuous measurement of vital blood parameters during extracorporeal blood circulation, and may contain sensors to monitor oxygen partial pressure and temperature on the arterial side of the extracorporeal blood flow circuit 3 as well as oxygen saturation, hemoglobin, hematocrit, and temperature on the venous side of the extracorporeal blood flow circuit.

The blood monitoring unit interface 710 includes tabbed display page 712 with tab 712a, such as may be disposed in any one of the sectors 108 of the graphical user interface 100 employed for tabbed display pages. FIG. 32 illustrates a non-limiting embodiment of the blood monitoring unit interface 710, which may include a venous oxygen saturation sensor module 714, a venous temperature module 716, a hemoglobin sensor module 718, a hematocrit sensor module 720, and a snapshot mechanism 722.

The venous oxygen saturation sensor module 714 includes a fixed alphanumeric title field 724, and a venous oxygen saturation value field 726 that displays measured values of venous oxygen saturation. The venous oxygen saturation value field 726 is associated with an appropriate units field (%) 728. The venous oxygen saturation sensor module 714 also includes a module settings menu button 124.

The venous temperature sensor module 716 includes a fixed alphanumeric title field 730, and a venous temperature value field 732 that displays measured values of venous temperature. The venous temperature value field 732 is associated with an appropriate units field (° C.) 734. The venous temperature sensor module 716 also includes a module settings menu button 124.

The hemoglobin sensor module 718 includes a fixed alphanumeric title field 736, and a hemoglobin value field 738 that displays measured values of blood hemoglobin. The hemoglobin value field 738 is associated with an appropriate units field (g/dl) 740. The hemoglobin sensor module 718 also includes a module settings menu button 124.

The hematocrit sensor module 720 includes a fixed alphanumeric title field 742, and a hematocrit value field 744 that displays measured values of blood hematocrit. The hematocrit value field 744 is associated with an appropriate units field (%) 746. The hematocrit sensor module 720 also includes a module settings menu button 124.

The snapshot mechanism 722 constitutes a touch or pressure sensitive button on the touch screen that, when touch or pressure activated, saves the displayed values for venous blood oxygen saturation ($S_vO_2$), venous temperature ($T_{ven}$) hemoglobin (Hb) and for hematocrit (Hct), into a memory device (i.e., a hardware memory device) operably associated with the processor 30 for storage and later retrieval. The associated memory device may be operably connected with the processor 30, either as an external device or as a component of the processor 30.

Footer Portion of the Graphical User Interface

The footer portion 104 displays primarily alphanumeric error messages in a display field 750 provided with a scrolling feature. Footer portion 104 is provided with a scroll-up button 752 and a scroll-down button, both of which are touch or pressure activated. Activation of the scroll-up button 752 causes the display field 750 to scroll up through the display field and activation of the scroll-down button 754 causes the display field 750 to scroll down through the display field. Error messages displayed by display field 750 include messages regarding malfunctions, misconnections, disconnections, and alarm states. The footer portion 104 may also be provided with a variable alarm message icon 756 and a help screen available button 758. The alarm message icon 756 is constructed so as to transition to different colors, and to display indicia, and to flash, corresponding to various high priority alarm states, medium priority alarm states, and low priority alarm states as described above.

For example, the alarm message icon 756 may display a red color when there is a high priority alarm present and flash at a rate indicative of a high priority alarm state while displaying a triangle with three exclamation points. On the other hand, the alarm message icon 756 may display a yellow color when there is a medium priority alarm present and flash at a rate indicative of a medium priority alarm state while displaying a triangle with two exclamation points. The alarm message icon 756 may display a cyan color without flashing when there is a low priority alarm present as well as displaying a triangle with one exclamation point. If more than one alarm has been triggered at the same time, then the alarm message icon 756 will transition to a state indicative of the highest level alarm currently in effect.

Figure 41A:
FIGS. 41a and 41b illustrate exemplary, non-limiting configurations of a single alarm help screen and a multiple alarm help screen, respectively, in accordance with embodiments of this disclosure.
Figure 41B:
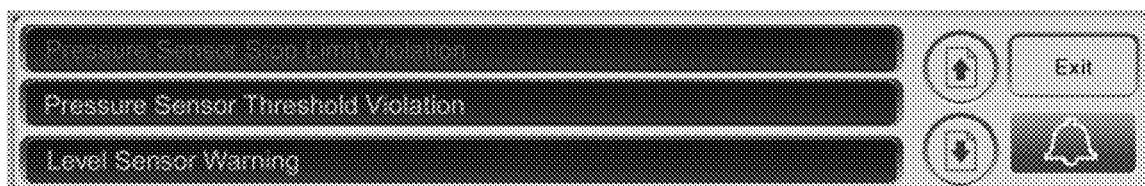

The help screen available button 758 is a touch or pressure activatable button that becomes available on the touchscreen 17 whenever one or more alarms have been triggered. Thus, in accordance with an embodiment of this disclosure, the help screen available button 758 is only available (i.e., is only displayed) when there is an activated alarm. Activation of the help screen available button 758 causes the footer portion 104 to display a single alarm help screen, as shown in FIG. 41*a*, when only a single alarm has been activated, or a multiple alarm help screen, as shown in FIG. 41*b*, when multiple alarms have been triggered. The single alarm help screen of FIG. 41*a* and the multiple alarm help screen of FIG. 41*b* are merely exemplary and should not be construed as limiting.

Set Up Mechanisms for the Graphical User Interface System

Figure 34A:
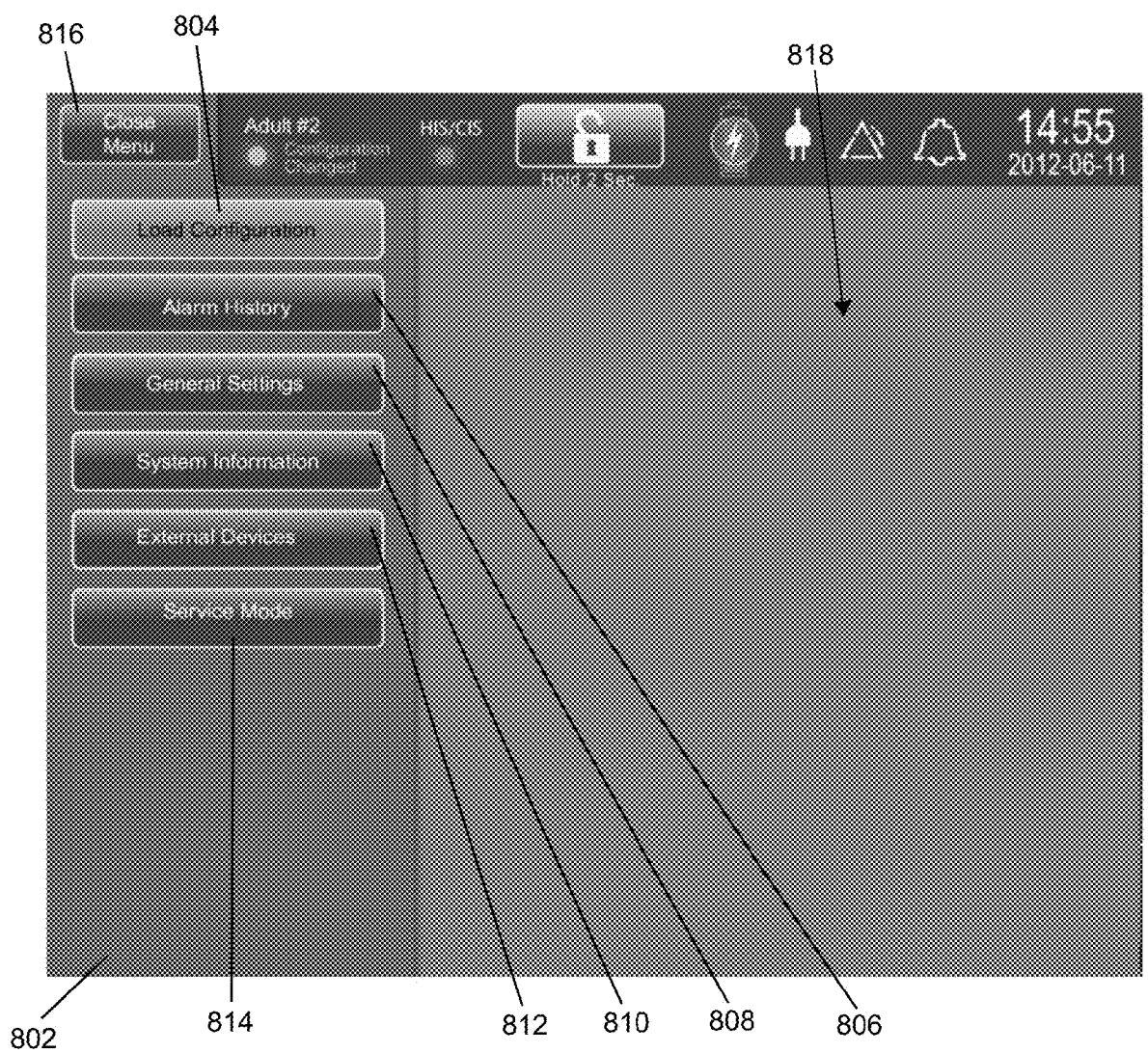
FIG. 34a illustrates an exemplary, non-limiting configuration of a system configuration menu interface in accordance with an embodiment of this disclosure.

The header 102 of the graphical user interface 100 includes a system settings menu button 214 that is used to activate a system configuration menu interface 802, such as shown in FIG. 34*a*. The system configuration menu interface 802 may have a nested structure, which is different from those portions of the graphical user interface 100 that are not directed to set up mechanisms and that are not nested structures. In other words, in accordance with an embodiment of this disclosure, the system and module configuration menu interfaces may have a nested structure because they pertain to set-up mechanisms, whereas the clinically operating portions of the graphical user interface are provided with a tab selectable page structure, which primarily is not a nested structure.

The system settings menu button 214 is touch or pressure activatable. Activation of the system settings menu button 214 by touch or pressure causes the system configuration menu interface 802 to be displayed by the graphical user interface 100. The system configuration menu interface 802 includes a load configuration button 804, an alarm history button 806, a general settings button 808, a system information button 810, an external devices button 812, a service mode button 814, and a close menu button 816. Each of buttons 804, 806, 808, 810, 812, 814 and 816 are activatable by touch or pressure.

Figure 34B:
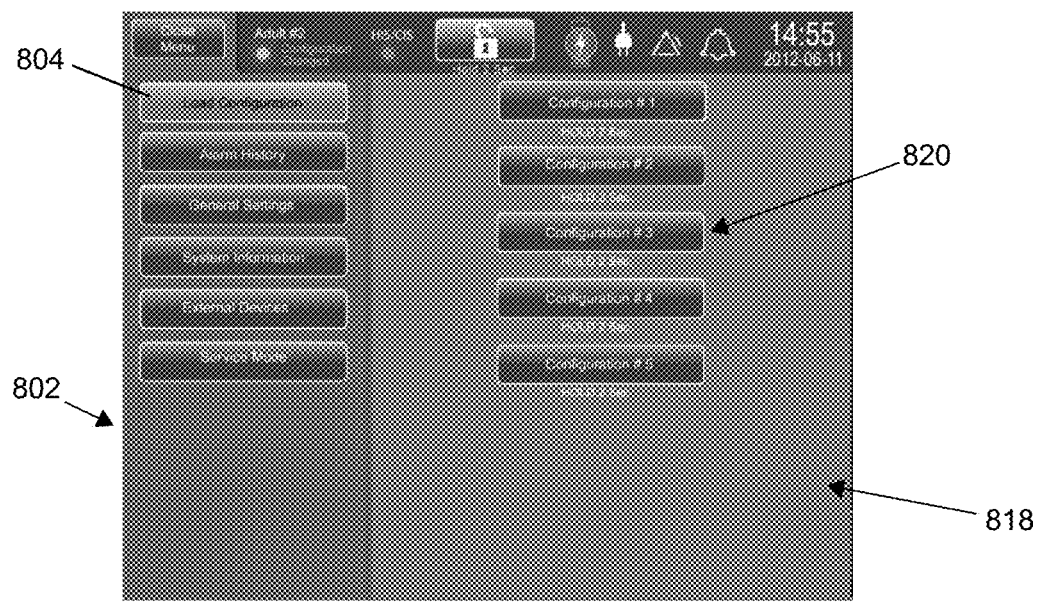
FIGS. 34b, 34c, 34d, 34e, 34f and 34g illustrate various sub-menus of the system configuration menu interface.

Activation of the load configuration button 804 by touch or pressure causes a menu 820 of selectable predefined graphical user interface configurations to be displayed in display field 818 of system configuration menu interface 802, such as shown by FIG. 34*b*. A user may then select one of the predefined graphical user interface configurations for display by the graphical user interface 100.

Figure 34C:

Activation of the alarm history button 806 by touch or pressure causes a log 822 of alarm messages to be displayed in display field 818 of system configuration menu interface 802, such as shown by FIG. 34*c*. The log 820 of alarm messages includes time and date of each message, and alarm messages may be color coded in accordance with their priority level, such as red for high priority alarm messages, yellow for medium priority alarm messages and cyan for low priority messages, and white for messages unassigned a priority.

Figure 34D:
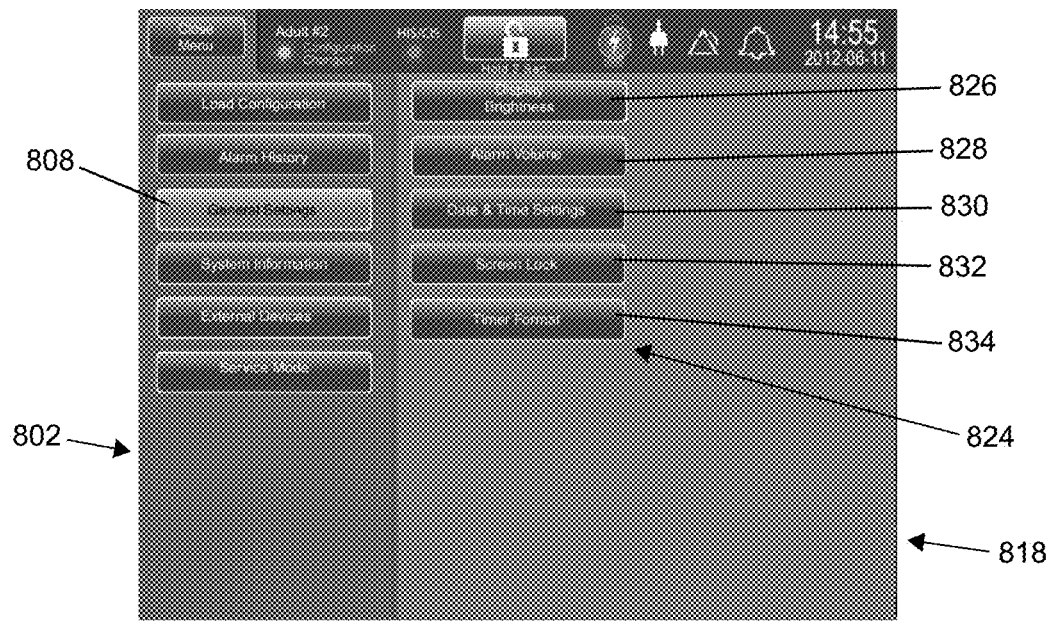

Activation of the general settings button 808 by touch or pressure causes a menu 824 of selectable settings buttons to be displayed in display field 818 of the system configuration menu interface 802, such as shown by FIG. 34*d*. The menu 824 of selectable settings buttons may include settings buttons directed to display brightness 826, alarm volume 828, data and time settings 830, screen lock settings 832, and timer format settings 834. Each of these settings buttons is touch or pressure activatable so as to display selectable settings corresponding to the selected category.

Figure 34E:
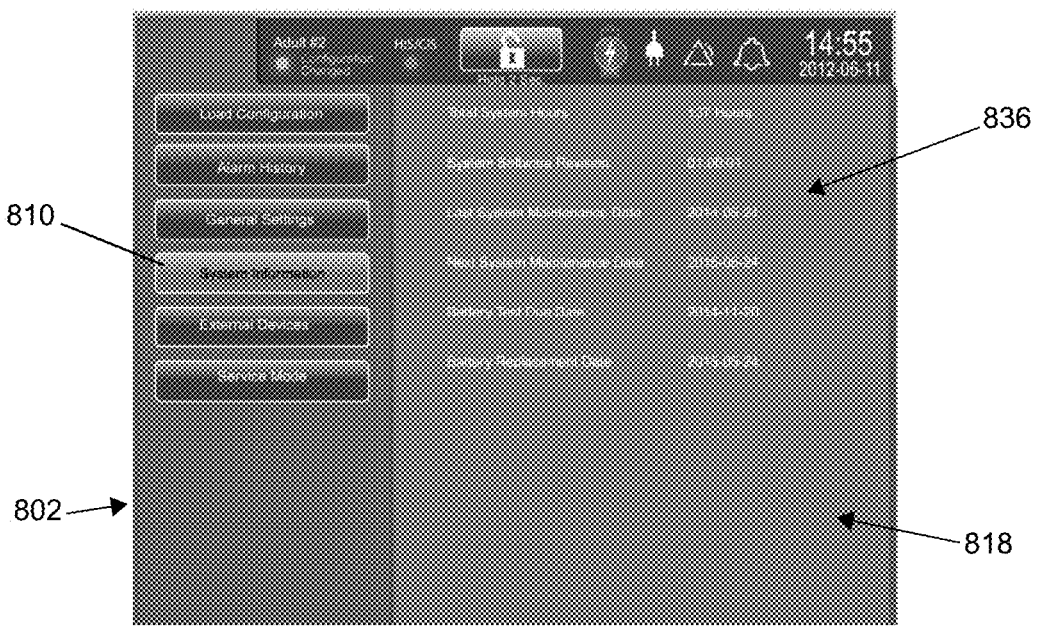

Activation of the system information button 810 by touch or pressure causes various system information 836 to be displayed in display field 818 of the system configuration menu interface 802, such as shown by FIG. 34*e*. The system information 836 displayed in the display field 818 may include information such as total system hours data, system software revision data, last system maintenance date data, next system maintenance due data, battery test due date data, and battery replacement date data.

Figure 34F:
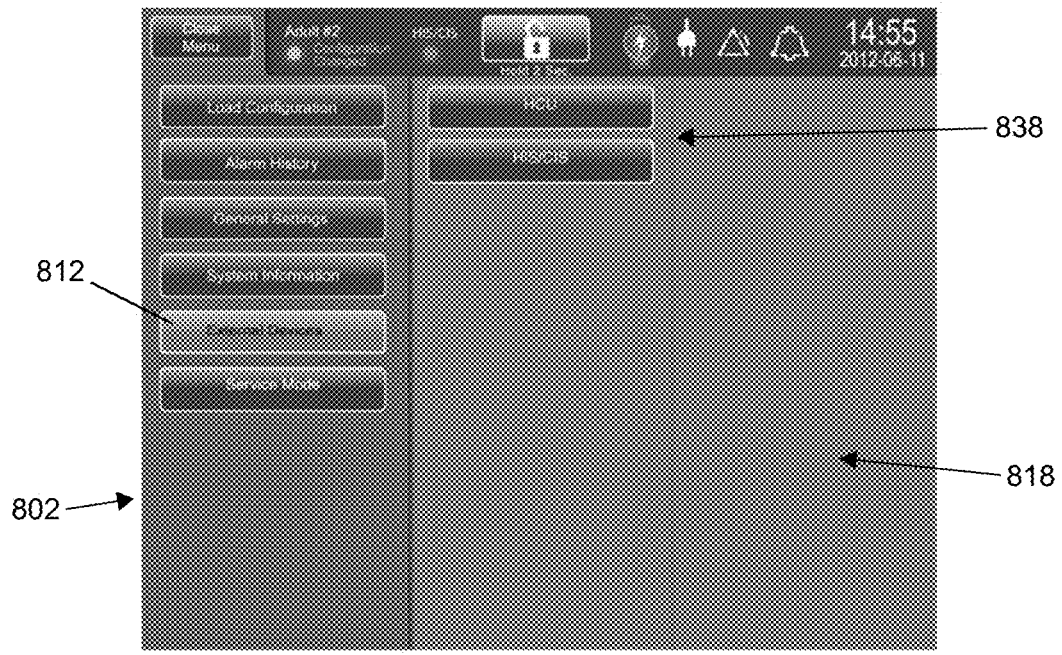
Figure 34G:
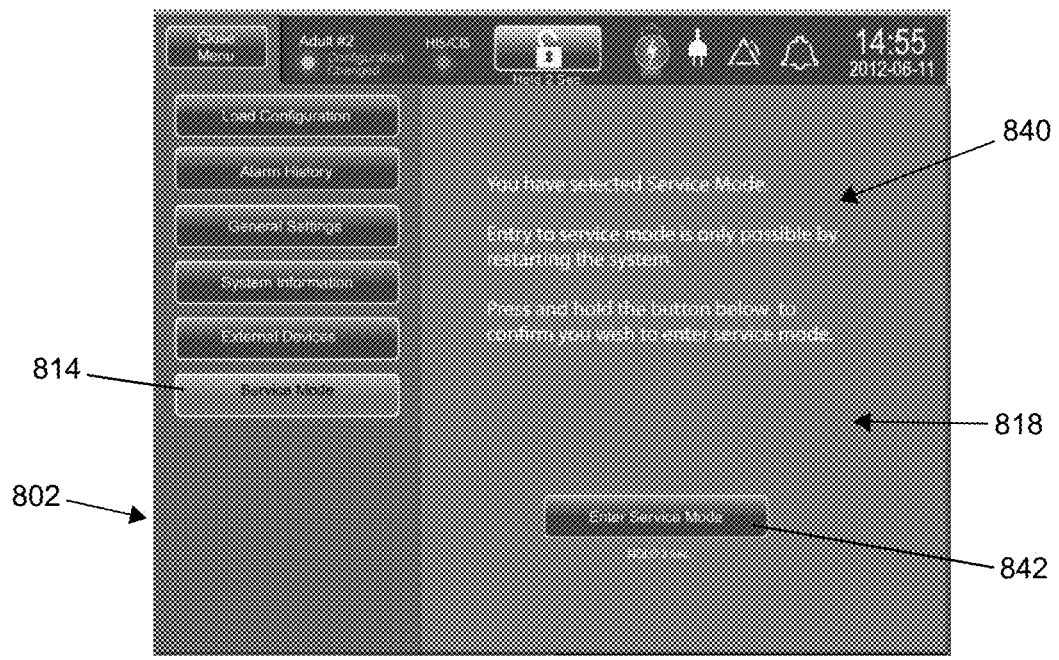

Activation of the external devices button 812 by touch or pressure causes an external devices menu 838 to be displayed in display field 818 of the system configuration menu interface 802, such as shown by FIG. 34*f*. The external devices menu 838 is used to enable or disable communication between the graphical user interface 100 and external devices, such as a heater-cooler unit 85 or a blood monitoring unit 800.

Activation of the service mode button 814 by touch or pressure causes instructions 840 to be displayed in the display field 818 of the system configuration menu interface 802 that detail how to leave the clinical mode of operation to enter into a service mode of operation, and vice versa. Activation of the service mode button 814 also causes an enter service mode button 842 to become available. The enter service mode button 842 is a touch or pressure activatable button, which must be pressed for at least two seconds before the processor 30 will enter into the service mode. The service mode is a mode of operation employed by a service technician to perform diagnostics and/or to provide programming updates and/or revisions for the processor 30.

Set Up Mechanisms for Modules of the Graphical User Interface

The various sensor modules and non-sensor modules described above may be provided with a module settings menu button 124, which is a touch or pressure activatable button of the touch screen. Activation of a module settings menu button 124 for a sensor module or for a non-sensor module will cause a set-up menu interface for that module to be displayed. Various set-up menu interfaces are described as follows.

Pressure Sensor Module Configuration Menu Interface

Figure 35A:
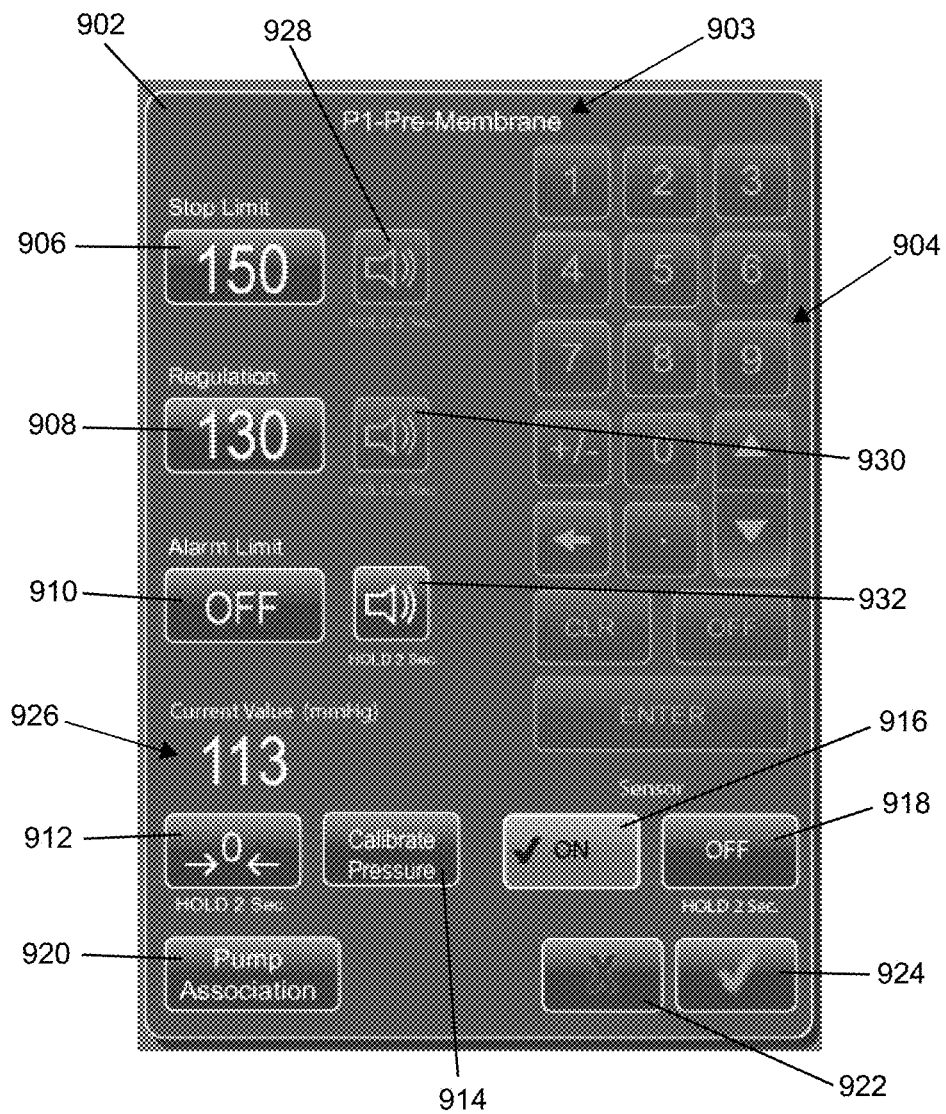
FIG. 35a illustrates an exemplary, non-limiting configuration of a module configuration menu for a pressure sensor module in accordance with an embodiment of this disclosure.

FIG. 35*a* illustrates the set-up menu interface for a pressure sensor module 152. Activation of the module settings menu button 124 by touch or pressure of a pressure sensor module 152 causes the pressure sensor module configuration menu interface 902 to be displayed by the graphical user interface 100. The pressure sensor module configuration menu interface 902 may include an alpha-numeric title field 903 that matches with the title field 154 of the associated pressure sensor module 152. The pressure sensor configuration menu interface 902 includes keypad 904 that is used to enter values into various settings fields 906, 908 of the menu 902. The pressure sensor configuration menu interface 902 includes a pressure stop limit field 906, a pressure regulation limit field 908, an alarm limit button 910, a zero pressure button 912, a calibrate pressure button 914, a sensor-on button 916, a sensor-off button 918, a pump association button 920, a settings cancel button 922 and settings activation button 924. Each of buttons 910, 912, 914, 916, 918, 920, 922 and 924 are activatable by touch or pressure. The pressure sensor configuration menu interface 902 may optionally be provided with a pressure display field 926 that may display the actual pressure measured by a pressure sensor 50 linked to the pressure sensor module 152.

The pressure sensor module configuration menu interface 902 of FIG. 35a is configured for display of pressure in units of mmHg. However, the pressure sensor module configuration menu interface may also be configured for pressure display in units of KPa.

The pressure stop limit field 906 and the pressure regulation limit field 908 are used to set the pressure stop limit value and the pressure threshold limit value, respectively, used by the pressure sensor module 152 to activate various pressure priority alarm states that are described above. The alarm limit button 910 is provided to enable and disable the setting of pressure alarm limit values. The pressure stop limit field 906, the pressure regulation limit field 908 and the alarm limit button 910 are each associated with an audio button 928, 930, 932, respectively. The audio buttons 928, 930 and 932 are each touch or pressure activatable buttons that are activated by touch or pressure for at least two seconds. These buttons 928, 930, 932 are used to disable and enable audio alarms associated with the corresponding thresholds. As shown in FIG. 35, buttons 928 and 930 are displayed by the pressure sensor module configuration menu interface 902 as duller and greyer than button 932, which indicates that audio alarms associated with buttons 928 and 930 have been disabled while the audio alarm associated with button 932 has been enabled.

Figure 35B:
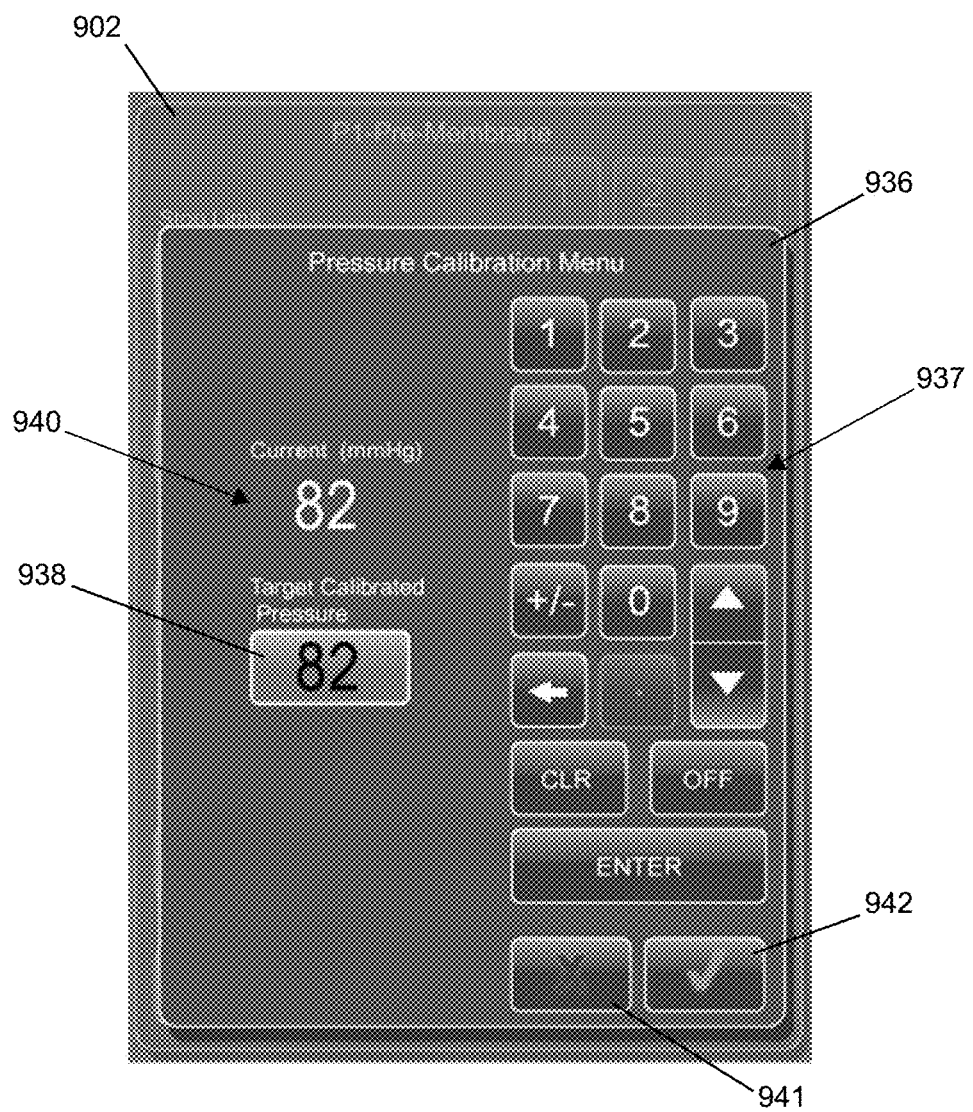
FIGS. 35b and 35c illustrate exemplary, non-limiting embodiments of associated sub-menu interfaces.
Figure 35C:
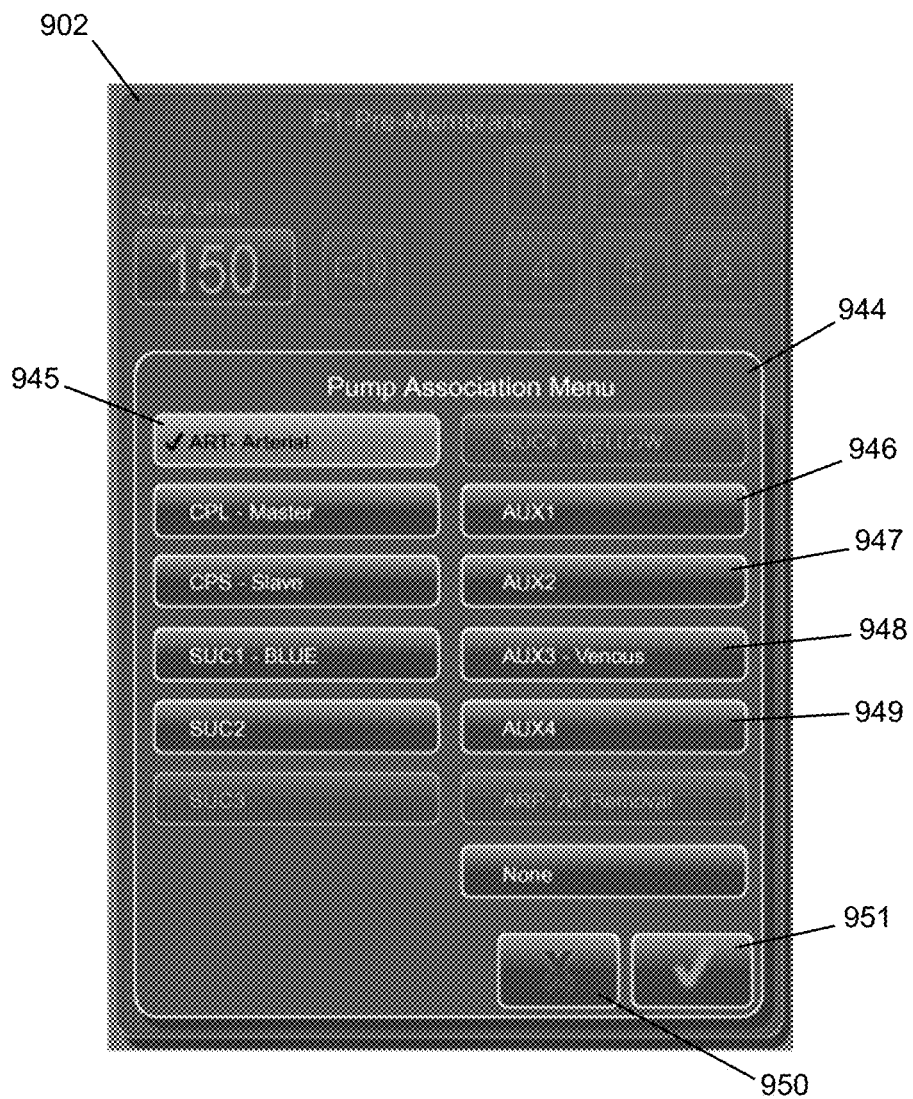

The zero pressure button 912 is a touch or pressure activatable button that, when activated by pressing and holding for at least two seconds, zeros the pressure channel. The calibrate pressure button 914 is a touch or pressure activatable single action button that, when activated, results in the display of a pressure calibration menu interface 936 as a pop-up overlaying a portion of the pressure sensor module configuration menu interface 902, as shown in FIG. 35b. The pressure calibration menu interface 936 allows a user to calibrate the linked pressure sensor after the pressure channel has been zeroed using the zero pressure button 912. The pressure calibration menu interface 936 may be provided with a keyboard 937 for entering a target calibrated pressure value into the target calibrated pressure data field. The pressure calibration menu interface 936 may include a pressure display field 940 that may display the actual pressure measured by a pressure sensor 50 linked to the pressure sensor module 152. The pressure calibration menu interface 936 includes a settings cancel button 941 and the settings activation button 942, which are two touch or pressure activatable single action buttons. Activation of the settings cancel button 941 closes the pressure calibration menu interface 936 without accepting any new changes to the target calibrated pressure. Activation of the settings activation button 942 closes the pressure calibration menu interface 936 while simultaneously accepting and enabling any new changes to the target calibrated pressure made using the pressure calibration menu interface 902.

The sensor-on button 916 and the sensor-off button 918 are two touch or pressure activatable single action buttons. Activation of the sensor-on button 916 enables the linked pressure sensor 50 and activation of the sensor-off button 918 disables the linked pressure sensor 50.

The pump association button 920 is a touch or pressure activatable single action button that, when activated, results in the display of a pressure sensor pump association menu interface 944 as a pop-up overlaying a portion of the pressure sensor module configuration menu interface 902. The pressure sensor pump association menu interface 944 allows a user to select a pump of the cardiopulmonary bypass system 1 and link it to the pressure sensor module 152 so that activation of the intervention button 158 by a user will affect the operation of the linked pump (i.e., the associated pump). Thus, the pressure sensor pump association menu interface 944 includes a plurality of enabled single action pump buttons 945, 946, 947, 948, 949 corresponding to pumps available to associate with the pressure sensor module 152. The pressure sensor pump association menu interface 944 may include not enabled single action pump buttons that pertain to those pumps not available to associate with the pressure sensor module 152, such as an air removal pump ("ARP"), for example. The pressure sensor pump association menu interface 944 may be provided with a "None" button, which may be selected when no pump is to be associated with the pressure sensor module 152. When a pump has been selected by activation of the corresponding pump button, then the pump button displays a check icon, such as shown by pump button 945 in the non-limiting example of FIG. 35c in which an arterial blood pump has been associated with the pressure sensor module 152.

The pressure sensor pump association menu interface 944 includes a settings cancel button 950 and the settings activation button 951, which are two touch or pressure activatable single action buttons. Activation of the settings cancel button 950 closes the pressure sensor pump association menu interface 944 without accepting any new changes to the pump associated with the pressure sensor module 152. Activation of the settings activation button 951 closes the pressure sensor pump association menu interface 944 while simultaneously accepting and enabling any new changes to the pump associated with the pressure sensor module 152 made using the pressure sensor pump association menu interface 944.

The settings cancel button 922 and the settings activation button 924 of the pressure sensor module configuration menu interface 902 are two touch or pressure activatable single action buttons. Activation of the settings cancel button 922 closes the pressure sensor module configuration menu interface 902 without accepting any new changes to the pressure sensor module configuration. Activation of the settings activation button 924 closes the pressure sensor module configuration menu interface 902 while simultaneously accepting and enabling any new changes to the pressure sensor module configuration made using the pressure sensor module configuration menu interface 902.

Bubble Detection Sensor Module Configuration Menu Interface

Figure 36A:
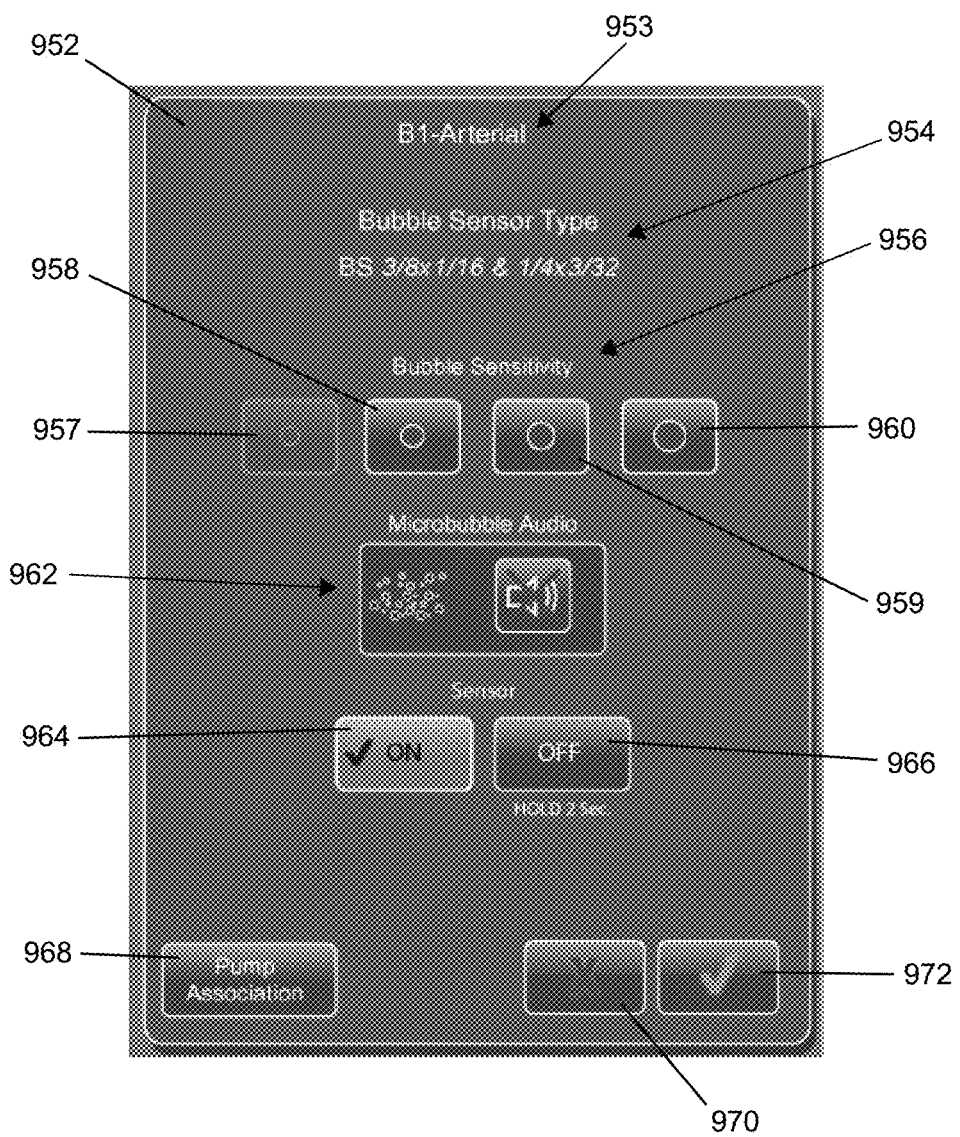
FIG. 36a illustrates an exemplary, non-limiting configuration of a module configuration menu for a bubble detection sensor module in accordance with an embodiment of this disclosure.

FIG. 36a illustrates the set-up menu interface for a bubble detection sensor module 162. Activation of the module settings menu button 124 by touch or pressure of a bubble detection sensor module 162 causes the bubble detection sensor module configuration menu interface 952 to be displayed by the graphical user interface 100. The bubble detection sensor module configuration menu interface 952 may include an alpha-numeric title field 953 that matches with the title field 164 of the associated bubble detection sensor module 162, and it may include an alpha-numeric bubble detection sensor-type field 954 that identifies a particular type of bubble detection sensor that is in use and linked to the bubble detection sensor module 162. The bubble detection sensor module configuration menu interface 952 includes a bubble sensitivity detection array 956 provided with a plurality of bubble detection level buttons 957, 958, 959, 960, and a microbubble audio alarm button 962, a sensor-on button 964, a sensor-off button 966, a pump association button 968, a settings cancel button 970 and settings activation button 972. Each of buttons 957, 958, 959, 960, 962, 964, 966, 968, 970 and 972 are activatable by touch or pressure.

The bubble sensitivity detection array 956 allows a user to set the alarm sensitivity of bubble detection by the associated bubble detection sensor module 162 by activating one of the bubble detection level buttons 957, 958, 959, 960. Each of the bubble detection level buttons 957, 958, 959, 960 is a touch or pressure activatable single action button, which sets a bubble detection size alarm threshold used by the bubble detection sensor module 162 to activate various bubble detection priority alarm states that are described above. The bubble sensitivity detection array 956 sets alarm states, but it does not change the size of bubbles detected by the linked bubble detection sensor 60. Bubble detection level button 957 corresponds to a detection alarm threshold of smallest sized bubbles (i.e., the highest bubble detection sensitivity) and bubble detection level button 960 corresponds to a detection alarm threshold of largest sized bubbles (i.e., the lowest bubble detection sensitivity), and the bubble detection level buttons 958 and 959 set alarm thresholds between these alarm thresholds settable using the bubble detection level buttons 957 and 960.

The microbubble audio alarm button 962 is provided to enable and disable the setting of microbubble audio alarms. Activating the microbubble audio alarm button 962 by touch or pressure causes the state of audio alarm to flip between an enabled state and a disabled state. For example, if the microbubble audio alarm is engaged, then activating microbubble audio alarm button 962 causes the audio alarm to disengage, and this disengaged state is indicated by a disengagement icon (i.e., a red "X" over an active speaker icon). If the microbubble audio alarm is disengaged, then activating the microbubble audio alarm button 962 causes the audio alarm to engage, and this engaged state is indicated by an engagement icon (i.e., an active speaker icon).

The sensor-on button 964 and the sensor-off button 966 are two touch or pressure activatable buttons, although the sensor-on button 964 is a single action button and the sensor-off button 966 must be pressed and held for at least two seconds to activate. Activation of the sensor-on button 964 enables the linked bubble detection sensor 60 and activation of the sensor-off button 966 disables the linked bubble detection sensor 60.

Figure 36B:
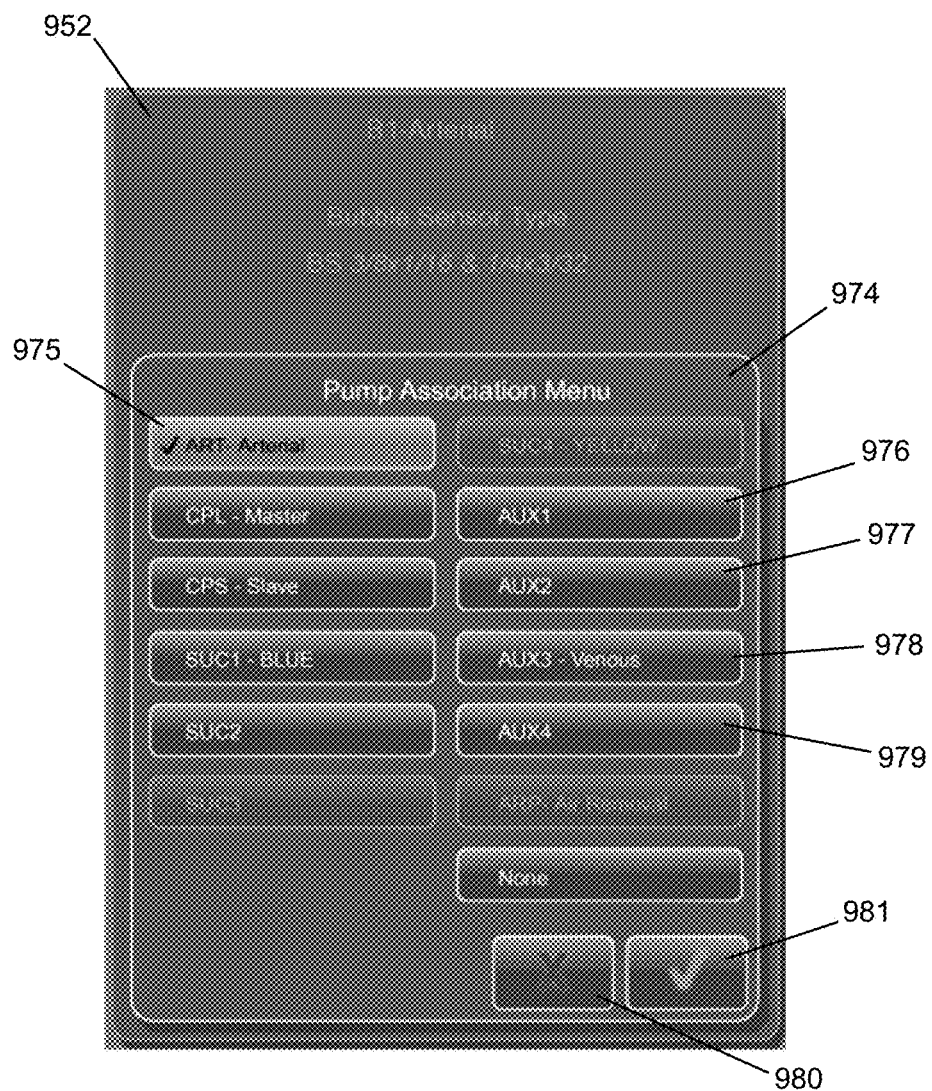
FIG. 36b illustrates an exemplary, non-limiting embodiment of an associated sub-menu interface.

The pump association button 968 is a touch or pressure activatable single action button that, when activated, results in the display of a bubble sensor pump association menu interface 974 as a pop-up overlaying a portion of the bubble detection sensor module configuration menu interface 952, such as shown in FIG. 36b. The bubble sensor pump association menu interface 974 allows a user to select a pump of the cardiopulmonary bypass system 1 and link it to the bubble detection sensor module 162 so that activation of the intervention button 168 by a user will affect the operation of the linked pump (i.e., the associated pump).

The bubble sensor pump association menu interface 974 includes a plurality of enabled single action pump buttons 975, 976, 977, 978, 979 corresponding to pumps available to associate with the bubble detection sensor module 162. The bubble sensor pump association menu interface 974 may include not enabled single action pump buttons that pertain to those pumps not available to associate with the bubble detection sensor module 162, such as an air removal pump ("ARP"), for example. The bubble sensor pump association menu interface 974 may be provided with a "None" button, which may be selected when no pump is to be associated with the bubble detection sensor module 162. When a pump has been selected by activation of the corresponding pump button, then the pump button displays a check icon, such as shown by pump button 975 in the non-limiting example of FIG. 36b.

The bubble sensor pump association menu interface 974 includes a settings cancel button 980 and the settings activation button 981, which are two touch or pressure activatable single action buttons. Activation of the settings cancel button 980 closes the bubble sensor pump association menu interface 974 without accepting any new changes to the pump associated with the bubble detection sensor module 162. Activation of the settings activation button 981 closes the bubble sensor pump association menu interface 974 while simultaneously accepting and enabling any new changes to the pump associated with the bubble detection sensor module 162 made using the bubble sensor pump association menu interface 974.

The settings cancel button 970 and the settings activation button 972 of the bubble detection sensor module configuration menu interface 952 are two touch or pressure activatable single action buttons. Activation of the settings cancel button 970 closes the bubble detection sensor module configuration menu interface 952 without accepting any new changes to the bubble detection sensor module configuration. Activation of the settings activation button 972 closes the bubble detection sensor module configuration menu interface 952 while simultaneously accepting and enabling any new changes to the bubble detection sensor module configuration made using the bubble detection sensor module configuration menu interface 952.

Level Sensor Module Configuration Menu Interface

Figure 37A:
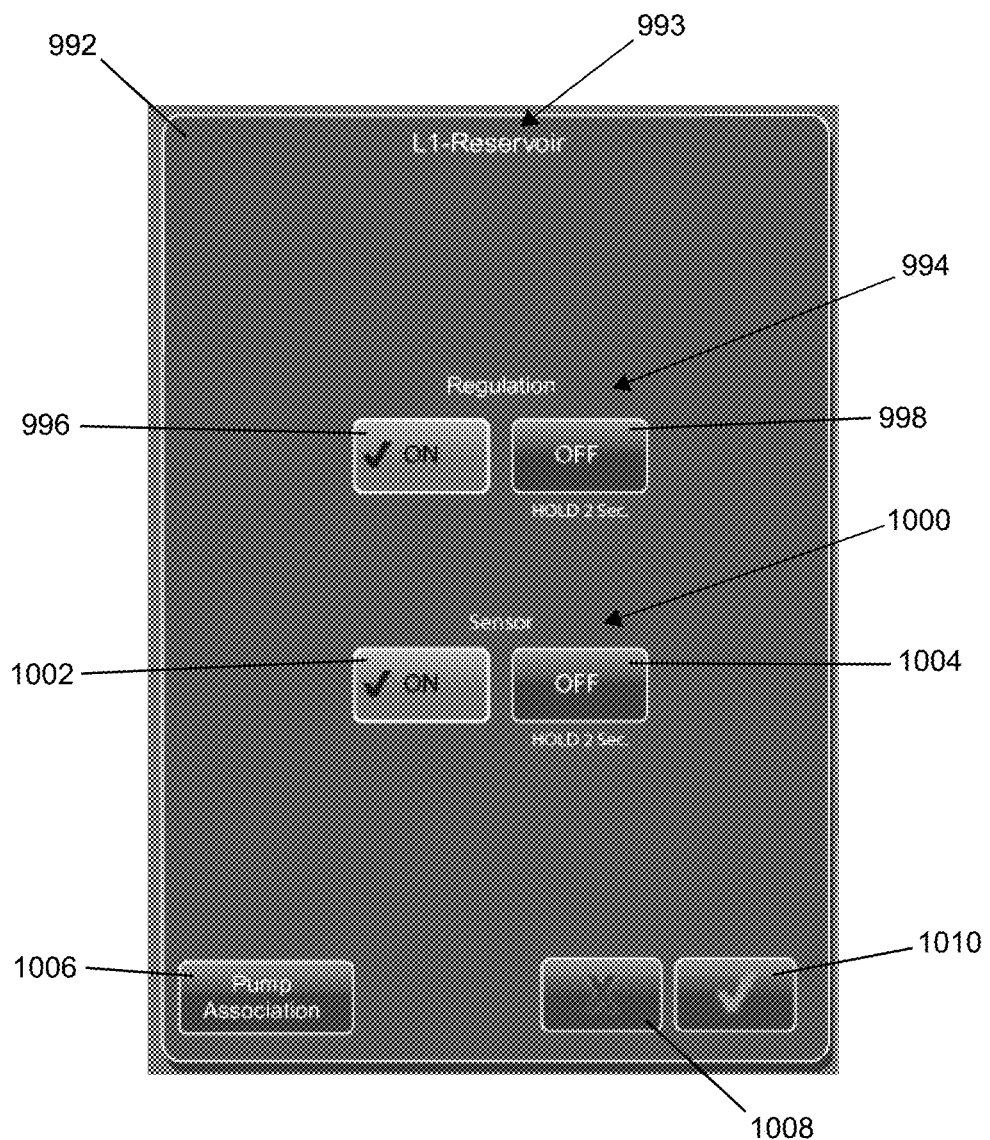
FIG. 37a illustrates an exemplary, non-limiting configuration of a module configuration menu for a level sensor module in accordance with an embodiment of this disclosure.

FIG. 37a illustrates the set-up menu interface for a level sensor module 172. Activation of the module settings menu button 124 by touch or pressure of a level sensor module 172 causes the level sensor module configuration menu interface 992 to be displayed by the graphical user interface 100. The level sensor module configuration menu interface 992 may include an alpha-numeric title field 993 that matches with the title field 174 of the associated level sensor module 172. The level sensor module configuration menu interface 992 includes a regulation interface 994 provided with a regulation-on button 996 and a regulation-off button 998. The regulation-on button 996 and the regulation-off button 998 are each touch or pressure activatable buttons; however, the regulation-on button 996 is a single action button and the regulation-off button 998 must be pressed and held for at least two seconds to activate. Activation of the regulation-on button 996 enables automatic level regulation via operation of an associated air removal pump 39 when the fluid level sensor 70 detects a low level, and activation of the regulation-off button 998 disables this automatic level regulation mechanism.

The level sensor module configuration menu interface 992 may also be provided with a level sensor activation interface 1000 that includes a sensor-on button 1002 and a sensor-off button 1004. The sensor-on button 1002 and the sensor-off button 1004 are each touch or pressure activatable buttons; however, the sensor-on button 1002 is a single action button and the sensor-off button 1004 must be pressed and held for at least two seconds to activate. Activation of the sensor-on button 1002 enables a linked reservoir fluid level sensor 70 and activation of the sensor-off button 1004 disables the linked reservoir fluid level sensor 70.

Figure 37B:
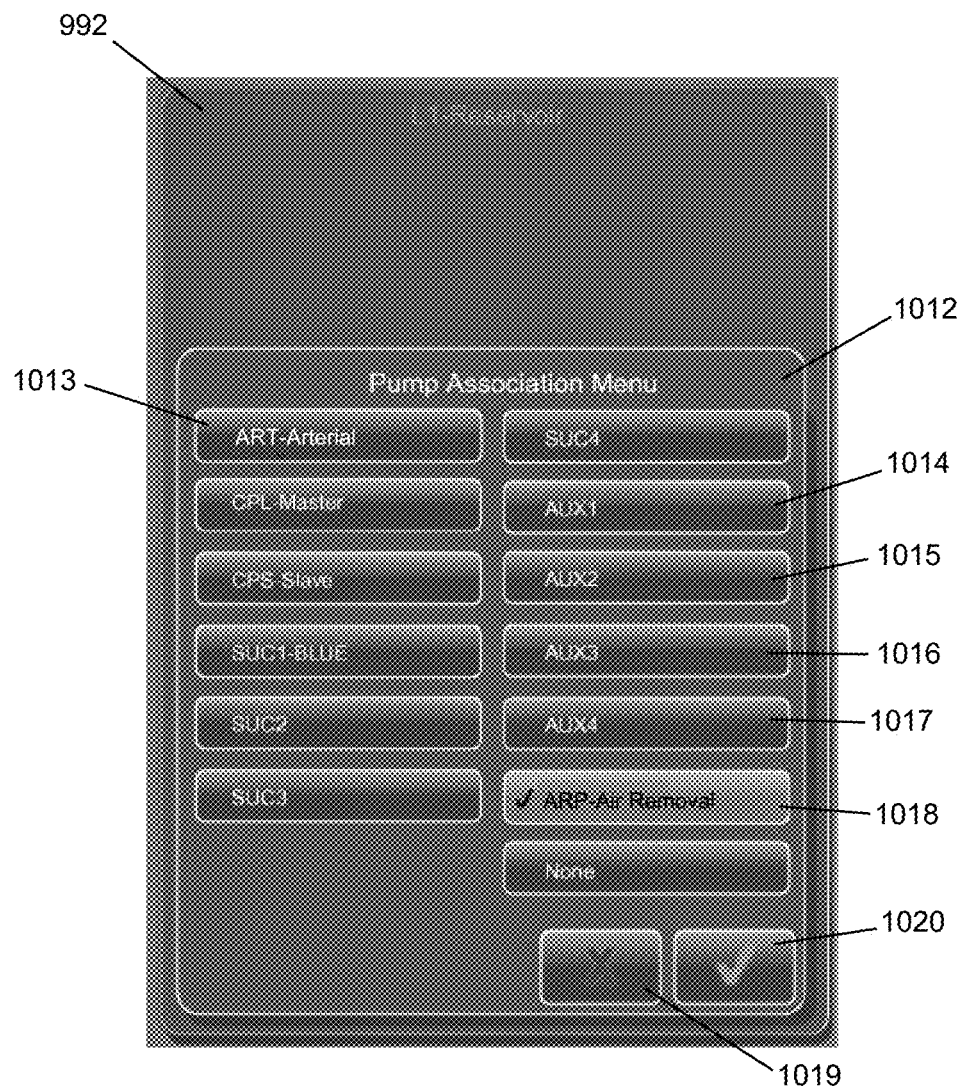
FIG. 37b illustrates an exemplary, non-limiting embodiment of an associated sub-menu interface.

The level sensor module configuration menu interface 992 may also be provided with a pump association button 1006, which is a touch or pressure activatable single action button that, when activated, results in the display of a level sensor pump association menu interface 1012 as a pop-up overlaying a portion of the level sensor module configuration menu interface 992, such as shown in FIG. 37b. The level sensor pump association menu interface 1012 allows a user to select a pump of the cardiopulmonary bypass system 1 and link it to the level sensor module 172 so that activation of the intervention button 178 by a user will affect the operation of the linked pump (i.e., the associated pump), which may be a blood pump 37, 38 or the air removal pump 39.

The level sensor pump association menu interface 1012 includes a plurality of enabled single action pump buttons 1013, 1014, 1015, 1016, 1017, 1018 corresponding to pumps available to associate with the level sensor module 172. The level sensor pump association menu interface 1012 may include not enabled single action pump buttons that pertain to those pumps not available to associate with the level sensor module 172. The level sensor pump association menu interface 1012 may be provided with a "None" button, which may be selected when no pump is to be associated with the level sensor module 172. When a pump has been selected by activation of the corresponding pump button, then the pump button displays a check icon, such as shown by pump button 1018 in the non-limiting example of FIG. 37b in which the pump associated with the level sensor module 172 is an air removal pump.

The level sensor pump association menu interface 1012 includes a settings cancel button 1019 and the settings activation button 1020, which are two touch or pressure activatable single action buttons. Activation of the settings cancel button 1019 closes the level sensor pump association menu interface 1012 without accepting any new changes to the pump associated with the level sensor module 172. Activation of the settings activation button 1020 closes the level sensor pump association menu interface 1012 while simultaneously accepting and enabling any new changes to the pump associated with the level sensor module 172 made using the level sensor pump association menu interface 1012.

The level sensor module configuration menu interface 992 may also be provided with a settings cancel button 1008 and a settings activation button 1010, which are two touch or pressure activatable single action buttons. Activation of the settings cancel button 1008 closes the level sensor module configuration menu interface 992 without accepting any new changes to the level sensor module configuration. Activation of the settings activation button 1010 closes the level sensor module configuration menu interface 992 while simultaneously accepting and enabling any new changes to the level sensor module configuration made using the level sensor module configuration menu interface 992.

Temperature Sensor Module Configuration Menu Interface

Figure 38:
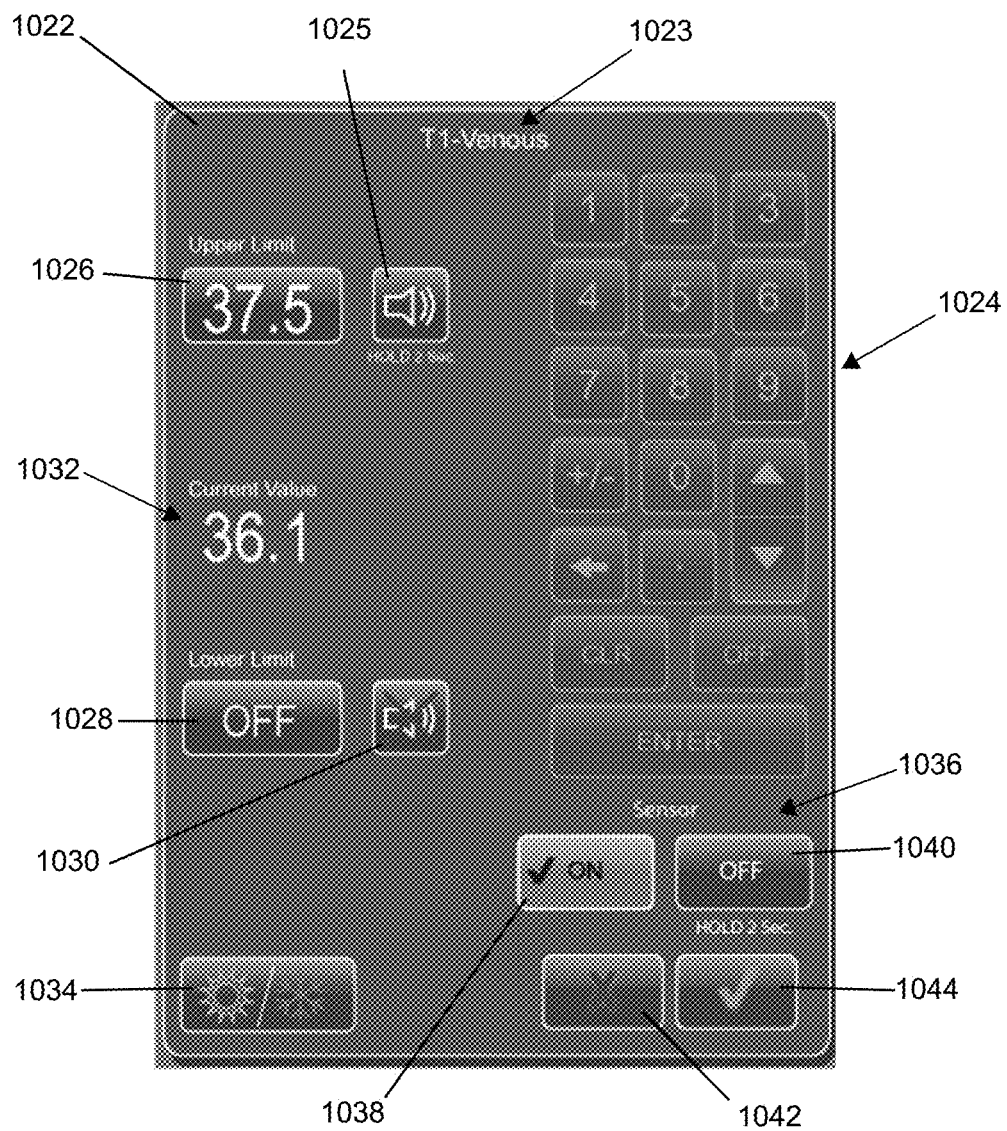
FIG. 38 illustrates an exemplary, non-limiting configuration of a module configuration menu for a temperature sensor module in accordance with an embodiment of this disclosure.

FIG. 38 illustrates the set-up menu interface for a temperature sensor module 182. Activation of the module settings menu button 124 by touch or pressure of a temperature sensor module 182 causes the temperature sensor module configuration menu interface 1022 to be displayed by the graphical user interface 100. The temperature sensor module configuration menu interface 1022 may include an alphanumeric title field 1023 that matches with the title field 184 of the associated temperature sensor module 182.

The temperature sensor configuration menu interface 1022 includes keypad 1024 that is used to enter values into various settings fields 1026, 1028 of the menu 1022. The temperature sensor configuration menu interface 1022 includes a temperature upper limit field 1026, an audio button 1025 corresponding to the upper limit, a temperature lower limit field 1028, an audio button 1030 corresponding to the lower limit, a heating-cooling unit association button 1034, a temperature sensor activation interface 1036 that includes a sensor-on button 1038 and a sensor-off button 1040, and a settings cancel button 1042 and settings activation button 1044. Each of buttons 1025, 1030, 1034, 1038, 1040, 1042 and 1044 are activatable by touch or pressure. The temperature sensor configuration menu interface 1022 may optionally be provided with a temperature display field 1032 that may display the actual temperature measured by a temperature sensor 80 linked to the temperature sensor module 182.

The temperature sensor module configuration menu interface 1022 of FIG. 38 is configured for display of temperature in units of degrees centigrade. However, the temperature sensor module configuration menu interface may also be configured for temperature display in units of degrees Fahrenheit.

The temperature upper limit field 1026 and the temperature lower limit field 1028 are used to set the temperature upper limit value and the temperature lower limit value, respectively, used by the temperature sensor module 182 to activate various temperature priority alarm states that are described above. The audio button 1025 is provided to enable and disable an audio alarm corresponding to an upper temperature alarm limit value and the audio button 1030 is provided to enable and disable an audio alarm corresponding to a lower temperature alarm limit value. The audio button 1025 is a touch or pressure activatable button that is activated when pressed for a period of at least two seconds in order to disable the corresponding audio alarm, whereas the audio button 1030 is a touch or pressure activatable single action button. In an embodiment of this disclosure, the audio button 1025 is configured as a single action button when used to enable the corresponding audio alarm and requires activation for a period of at least two seconds in order to disable this audio alarm.

The heating-cooling unit association button 1034 is a touch or pressure activatable single action button that, when activated, results in the display of a heating-cooling unit association menu interface as a pop-up overlaying a portion of the temperature sensor module configuration menu interface 1022. The heating-cooling unit association menu interface allows a user to link a heater-cooler unit 85 of the cardiopulmonary bypass system 1 with the temperature sensor 80 as appropriate when the temperature sensor 80 is disposed to measure a heating-cooling unit patient circuit external temperature or a Cardioplegia circuit external temperature, or to specify when there is no association between the temperature sensor 80 and the heater-cooler unit 85.

The sensor-on button 1038 is a single action touch or pressure activatable button and the sensor-off button 1040 is a touch or pressure activatable button that must be pressed for at least two seconds to activate. Activation of the sensor-on button 1038 enables the linked temperature sensor 80 and activation of the sensor-off button 1040 disables the linked temperature sensor 80.

The settings cancel button 1042 and the settings activation button 1044 are two touch or pressure activatable single action buttons. Activation of the settings cancel button 1042 closes the temperature sensor module configuration menu interface 1022 without accepting any new changes to the temperature sensor module configuration. Activation of the settings activation button 1044 closes the temperature sensor module configuration menu interface 1022 while simultaneously accepting and enabling any new changes to the temperature sensor module configuration made using the temperature sensor module configuration menu interface 1022.

Flow Sensor Module Configuration Menu Interface

Figure 39A:
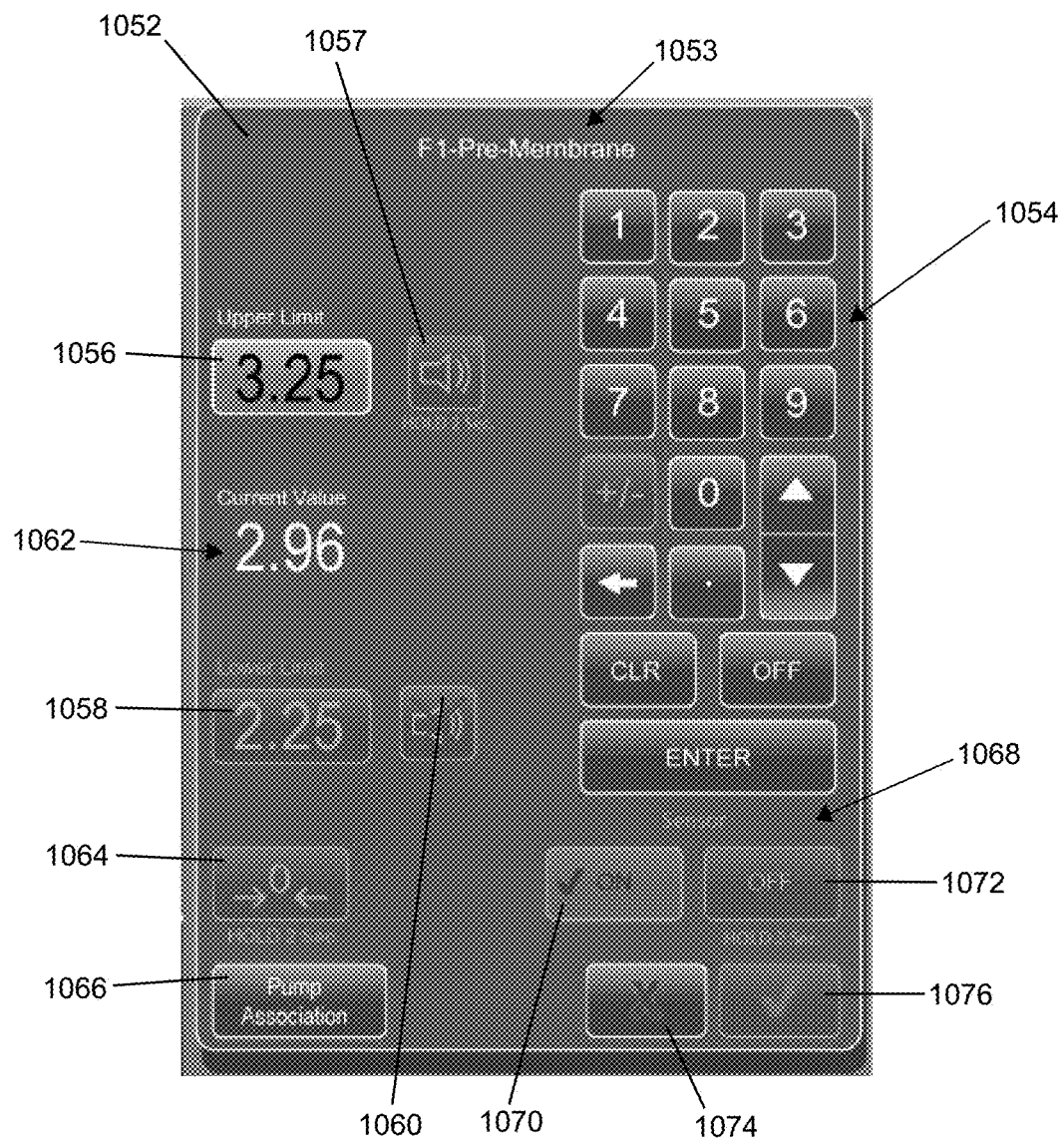
FIG. 39a illustrates an exemplary, non-limiting configuration of a module configuration menu for a flow sensor module in accordance with an embodiment of this disclosure.

FIG. 39*a* illustrates the set-up menu interface for a flow sensor module 192. Activation of the module settings menu button 124 by touch or pressure of a flow sensor module 192 causes the flow sensor module configuration menu interface 1052 to be displayed by the graphical user interface 100. The flow sensor module configuration menu interface 1052 may include an alpha-numeric title field 1053 that matches with the title field 194 of the associated flow sensor module 192. The flow sensor configuration menu interface 1052 includes keypad 1054 that is used to enter values into various settings fields 1056, 1058 of the menu interface 1052. The flow sensor configuration menu interface 1052 includes a flow upper limit field 1056, an audio button 1057 corresponding to the upper limit, a flow lower limit field 1058, an audio button 1060 corresponding to the lower limit, a zero flow button 1064, a flow sensor activation interface 1068 that includes a sensor-on button 1070 and a sensor-off button 1072, a pump association button 1066, a settings cancel button 1074 and settings activation button 1076. Each of buttons 1057, 1060, 1064, 1066, 1070, 1072, 1074 and 1076 are activatable by touch or pressure. The pressure sensor configuration menu interface 1052 may optionally be provided with a flow display field 1062 that may display the actual flow measured by a flow sensor 90 linked to the flow sensor module 192.

The flow upper limit field 1056 and the flow lower limit field 1058 are used to set the flow upper limit value and the flow lower limit value, respectively, used by the flow sensor module 192 to activate various flow priority alarm states that are described above. The audio button 1057 is provided to enable and disable an audio alarm corresponding to an upper flow alarm limit value and the audio button 1060 is provided to enable and disable an audio alarm corresponding to a lower flow alarm limit value. The audio button 1057 is a touch or pressure button that is activated when pressed for a period of at least two seconds in order to disengage the corresponding audio alarm, although the audio button 1057 may be configured as a single action button in order to enable the corresponding audio alarm, whereas the lower limit disengagement button 1060 is a touch or pressure activatable single action button for both enabling and disabling its corresponding audio alarm.

Figure 39B:
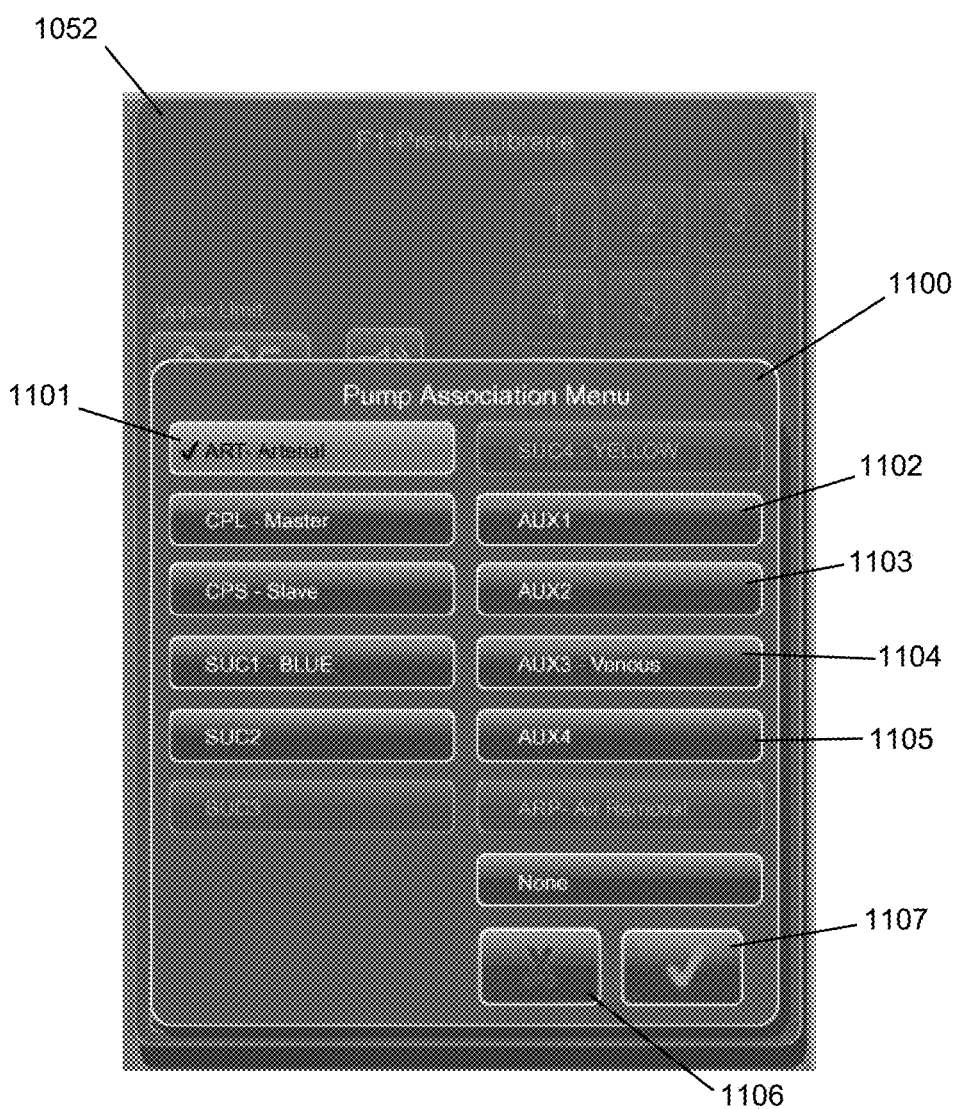
FIG. 39b illustrates an exemplary, non-limiting embodiment of an associated sub-menu interface.

The zero flow button 1064 is a touch or pressure activatable button that, when activated by pressing and holding for at least two seconds, zeros the flow sensor. The pump association button 1066 is a touch or pressure activatable single action button that, when activated, results in the display of a level sensor pump association menu interface 1100 as a pop-up overlaying a portion of the flow sensor module configuration menu interface 1052, such as shown in FIG. 39*b*. The level sensor pump association menu interface 1100 allows a user to select a centrifugal pump of the cardiopulmonary bypass system 1 and link it to the flow sensor module 192.

The flow sensor pump association menu interface 1100 includes a plurality of enabled single action pump buttons 1101, 1102, 1103, 1104, 1105 corresponding to pumps available to associate with the flow sensor module 192. The flow sensor pump association menu interface 1100 may include not enabled single action pump buttons that pertain to those pumps not available to associate with the flow sensor module 192. The flow sensor pump association menu interface 1100 may be provided with a "None" button, which may be selected when no pump is to be associated with the flow sensor module 192. When a pump has been selected by activation of the corresponding pump button, then the pump button displays a check icon, such as shown by pump button 1101 in the non-limiting example of FIG. 39*b* in which the pump associated with the level sensor module 192 may be a centrifugal blood pump.

The flow sensor pump association menu interface 1100 includes a settings cancel button 1106 and the settings activation button 1107, which are two touch or pressure activatable single action buttons. Activation of the settings cancel button 1106 closes the flow sensor pump association menu interface 1100 without accepting any new changes to the pump associated with the flow sensor module 192. Activation of the settings activation button 1107 closes the flow sensor pump association menu interface 1100 while simultaneously accepting and enabling any new changes to the pump associated with the flow sensor module 192 made using the flow sensor pump association menu interface 1100.

The sensor-on button 1070 is a single action touch or pressure activatable button and the sensor-off button 1072 is a touch or pressure activatable button that must be pressed for at least two seconds to activate. Activation of the sensor-on button 1070 enables the linked flow sensor 90 and activation of the sensor-off button 1072 disables the linked flow sensor 90.

The settings cancel button 1074 and the settings activation button 1076 are two touch or pressure activatable single action buttons of the flow sensor module configuration menu interface 1052. Activation of the settings cancel button 1074 closes the flow sensor module configuration menu interface 1052 without accepting any new changes to the flow sensor module configuration. Activation of the settings activation button 1076 closes the flow sensor module configuration menu interface 1052 while simultaneously accepting and enabling any new changes to the flow sensor module configuration made using the flow sensor module configuration menu interface 1052.

Pressure Delta Sensor Module Configuration Menu Interface

Figure 40:
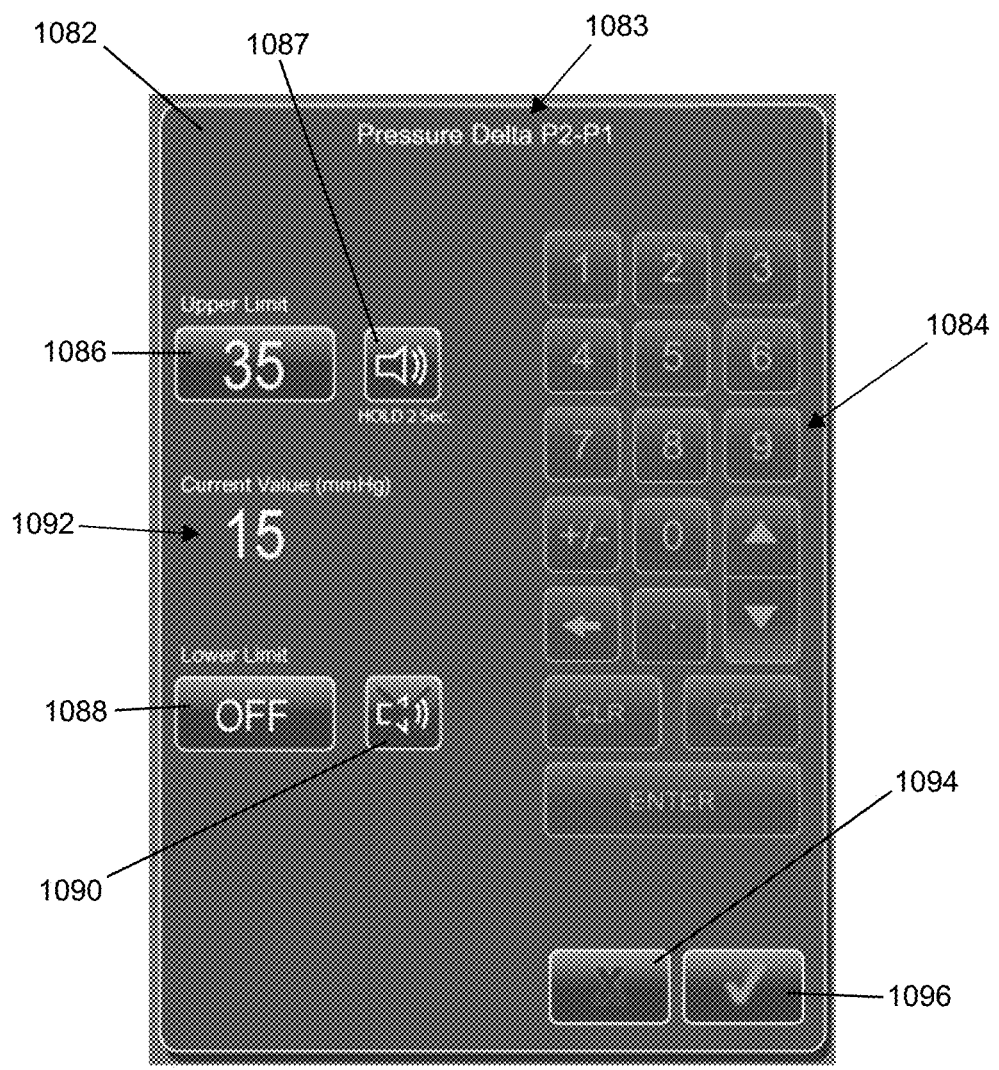
FIG. 40 illustrates an exemplary, non-limiting configuration of a module configuration menu for a pressure delta sensor module in accordance with an embodiment of this disclosure.

FIG. 40 illustrates the set-up menu interface for a pressure delta sensor module 252. Activation of the module settings menu button 124 by touch or pressure of a pressure delta sensor module 252 causes the pressure delta sensor module configuration menu interface 1082 to be displayed by the graphical user interface 100. The pressure delta sensor module configuration menu interface 1082 may include an alpha-numeric title field 1083 that matches with the title field 254 of the associated pressure delta sensor module 252. The pressure delta sensor configuration menu interface 1082 includes keypad 1084 that is used to enter values into various settings fields 1086, 1088 of the configuration menu interface 1082. The pressure delta sensor configuration menu interface 1082 includes a pressure delta upper limit field 1086, an audio button 1087 corresponding to the upper limit, a pressure delta lower limit field 1088, an audio button 1090 corresponding to the lower limit, a settings cancel button 1094 and settings activation button 1096. Each of buttons 1087, 1090, 1094 and 1096 are activatable by touch or pressure. The pressure sensor configuration menu interface 1082 may optionally be provided with a pressure delta display field 1092 that may display the actual pressure delta as derived from measured pressure values from at least two pressure sensors 50 linked to the pressure delta sensor module 252.

The pressure delta sensor module configuration menu interface 1082 of FIG. 40 is configured for display of pressure delta values in units of mmHg. However, the pressure delta sensor module configuration menu interface may also be configured for pressure delta value display in units of KPa.

The pressure delta upper limit field 1086 and the pressure delta lower limit field 1088 are used to set the pressure delta upper limit value and the pressure delta lower limit value, respectively, used by the pressure delta sensor module 252 to activate various pressure delta priority alarm states that are described above. The audio button 1087 is provided to enable and disable the audio alarm corresponding to an upper pressure delta alarm limit value. For example, touch or pressure sustained for at least two seconds on the audio button 1087 when the audio alarm is in an enabled state will cause the audio alarm to transition to a disabled state. When the audio alarm corresponding to the upper limit is disabled, then single action touch or pressure on the audio button 1087 will cause the audio alarm to transition to back to the enabled state.

The audio button 1090 is provided to enable and disable the audio alarm corresponding to a lower pressure delta alarm limit value. The audio button 1090 is a touch or pressure activatable single action button, so a single touch or press transitions the audio alarm between the enabled state to the disabled state, and between the disabled state and the enabled state.

The settings cancel button 1094 and the settings activation button 1096 are two touch or pressure activatable single action buttons. Activation of the settings cancel button 1094 closes the pressure delta sensor module configuration menu interface 1082 without accepting any new changes to the pressure delta sensor module configuration. Activation of the settings activation button 1096 closes the pressure delta sensor module configuration menu interface 1082 while simultaneously accepting and enabling any new changes to the pressure delta sensor module configuration made using the pressure delta sensor module configuration menu interface 1082.

Method Embodiment(s) Directed to User Interface Set-up

In accordance with this disclosure, a method of configuring a graphical user interface of a touchscreen prior to operation in a clinical operation mode is provided, wherein the method includes the steps of: (a) in response to a first signal, displaying a sensor module configuration menu interface associated with a tabbed display page of the graphical user interface displayed by the touchscreen; and (b) in response to a second signal, setting at least one alarm limit for a sensor module associated with the sensor module configuration menu interface associated with the tabbed display page. In this context, the clinical operation mode of the touchscreen is the mode of operation used when the graphical user interface has been configured and is operating to display and monitor data inputs from a plurality of sensors associated with a plurality of sensor modules. In accordance with an embodiment of this method, the first signal is generated as a result of activation of a touch or pressure activatable module settings menu button of the sensor module of the tabbed display page. In accordance with an embodiment of this method, the second signal is generated as a result of activation of a touch or pressure activatable button of the sensor module configuration menu interface associated with the tabbed display page. In accordance with an embodiment of this disclosure, the method may further include the step of (c), in response to a third signal, overlaying a pump association menu interface on a portion of the sensor module configuration menu interface of the tabbed display page in order to enable a selective association of a pump with the sensor module of the tabbed display page. In accordance with an embodiment of this disclosure, this third signal is generated as a result of activation of a touch or pressure activatable pump association button of the sensor module configuration menu interface.

In accordance with an embodiment of this disclosure, the method may include the steps (c), in response to a third signal, displaying a sensor module configuration menu interface on a portion of an untabbed display page of the graphical user interface displayed by the touchscreen, and (d), in response to a fourth signal, setting at least one alarm limit for a sensor module associated with the sensor module configuration menu interface associated with the untabbed display page. In accordance with an embodiment of this disclosure, this third signal may be generated as a result of activation of a touch or pressure activatable module settings menu button of the sensor module of the untabbed display page. In accordance with an embodiment of this disclosure, this fourth signal may be generated as a result of activation of a touch or pressure activatable button of the sensor module configuration menu interface of the untabbed display page. In accordance with an embodiment of this disclosure, the method may further include the step of (e), in response to a fifth signal, overlaying a pump association menu interface on a portion of the sensor module configuration menu interface of the untabbed display page in order to enable a selective association of a pump with the sensor module of the untabbed display page. In accordance with an embodiment of this disclosure, the fifth signal may be generated upon activation of a touch or pressure activatable pump association button of the sensor module configuration menu interface.

In accordance with an embodiment of this disclosure, each sensor module associated with its corresponding sensor module configuration menu interface may be independently selected from the group consisting of a pressure sensor module associated with a pressure sensor module configuration menu interface, a bubble detection sensor module associated with a bubble detection sensor module configuration menu interface, a level sensor module associated with a level sensor module configuration menu interface, a temperature sensor module associated with a temperature sensor module configuration menu interface, a flow sensor module associated with a flow sensor module configuration menu interface, and a pressure delta sensor module associated with a pressure delta sensor module configuration menu interface. In accordance with an embodiment of this disclosure, the method may include the step of activating a system configuration menu interface in order to select a predefined graphical user interface configuration, or configure at least one selectable alarm setting selected from the group consisting of brightness and alarm volume, or display an external device menu. However, the system configuration menu interface may be provided with other options employable for configuring the system.

In accordance with an embodiment of this disclosure, the method may include the step of closing the sensor module configuration menu interface of the tabbed display page so as to accept and enable the at least one alarm limit of the sensor module of the tabbed display page, and/or it may also include the step of closing the sensor module configuration menu interface of the untabbed display page in order to accept and enable the at least one alarm limit of the sensor module of the untabbed display page.

Miscellaneous Comments

Thus, according to this disclosure, a graphical user interface has been described that provides convenient customization, flexible configurations, and a modular structure, which employs an intuitive design, thereby facilitating ease of use and safety of use. Also according to this disclosure, a graphical user interface has been described with integrated alarms that enhance safety when using the graphical user interface. A graphical user interface, in accordance with this disclosure, is provided with various staged set-up mechanisms for setting up the system settings, as well as for setting up various sensor modules and non-sensor modules configured within at least one untabbed display page and a plurality of tabbed display pages.

The foregoing description provided by this disclosure has been presented for the purpose of illustration and description only and is not to be construed as limiting the scope of the invention, as claimed, in any way. The scope of the invention is to be determined from the claims appended hereto.

We claim:

1. A cardiopulmonary bypass system comprising:
a processor;
a touchscreen comprising a customizable graphical user interface operably connected to the processor to provide user input to the processor and to display measured data pertaining to one or more parameters outputted from the processor, wherein the graphical user interface is provided with a central portion divided into four sections, wherein one section displays an untabbed display page and three sections display a plurality of tabbed display pages, wherein each section is customizable by an operator of the cardiopulmonary bypass system to include selected modules, and wherein the untabbed display page comprises a plurality of sensor modules and at least one tabbed page comprises a plurality of sensor modules that are customizable by an operator of the cardiopulmonary bypass system to include selected modules, and at least one tabbed display page comprises a plurality of cardioplegia modules, wherein the at least one tabbed display page comprising the plurality of sensor modules and the at least one tabbed display page comprising the plurality of cardioplegia modules are located in different sections of the central portion; and
a plurality of sensors disposed to measure one or more parameters of an extracorporeal blood flow circuit of the cardiopulmonary bypass system, wherein the plurality of sensors are operably connected to input measured data pertaining to the one or more parameters to the processor, and wherein each sensor is linked to one of the sensor modules of either the untabbed display page or one of the tabbed display pages so that data measured by each sensor is displayable by the graphical user interface,
wherein each tabbed display page comprises a contiguous tab attached thereto, and wherein each tabbed display page is displayable in a displayed mode and in an overlaid mode so that the graphical user interface is operable to display the untabbed display page and three tabbed display pages in the displayed mode at the same time, wherein when displayed in the displayed mode all of the tabbed display page is in view, and when displayed in the overlaid mode only the contiguous tab of the tabbed display page is in view, wherein each contiguous tab is capable of transitioning to an alarm state so that when the corresponding tabbed display page is displayed in the overlaid mode and any sensor module of the corresponding tabbed display page transitions to an alarm state, the contiguous tab transitions to a viewable alarm state, and wherein at least the untabbed display page includes a plurality of sectors and at least one section of the plurality of sectors has a sensor module settings menu button used to activate a module configuration menu interface used to configure the at least one sector to display information according to specified preferences for a current sensor module being displayed, and
wherein the graphical user interface comprises a clinical parameter monitoring and simulation user interface formed by a combined simultaneous display of a patient monitor tabbed display page, a simulator keypad tabbed display page having a simulator keypad configuration, and a simulator screen tabbed display page having a simulator screen configuration, wherein, when the patient monitor tabbed display page, the simulator keypad tabbed display page, and the simulator screen tabbed display page are each displayed simultaneously in the display mode, with the patient monitor tabbed display page, the simulator keypad tabbed display page and the simulator screen tabbed display page displayed in separate sections of the central portion, these tabbed display pages are operable together as a clinical parameter monitoring and simulation interface.

2. The cardiopulmonary bypass system according to claim 1, wherein each sensor module of the untabbed page is individually selected from the group consisting of a pressure sensor module, a bubble detection sensor module, a level sensor module, a flow sensor module, a pressure delta data sensor module, and a temperature sensor module.

3. The cardiopulmonary bypass system according to claim 1, wherein the untabbed page includes at least one pressure sensor module, at least one bubble detection sensor module, and at least one level sensor module.

4. The cardiopulmonary bypass system according to claim 3, wherein each of the at least one pressure sensor module, the at least one bubble detection sensor module, and the at least one level sensor module is capable of displaying a plurality of alarm states selected from at least two of a high priority alarm state, a medium priority alarm state, and a low priority alarm state.

5. The cardiopulmonary bypass system according to claim 3, wherein the at least one pressure sensor module comprises a pressure value data field and a touch or pressure activated intervention button, wherein activation of the intervention button by touch or pressure causes operation of a pump of the cardiopulmonary bypass system to be temporarily modified.

6. The cardiopulmonary bypass system according to claim 3, wherein the at least one bubble detection sensor module comprises a bubble detection data field and a touch or pressure activated reset button, wherein the bubble detection data field displays bubble detection data obtained from a bubble detection sensor.

7. The cardiopulmonary bypass system according to claim 6, wherein the at least one bubble detection sensor module displays a high priority alarm state when the bubble detection sensor detects bubbles exceeding a preset bubble detection size value, and the bubble detection sensor module continues to display the high priority alarm state until the reset button is activated by touch or pressure and the bubbles detected by the bubble detection sensor concurrently do not exceed the preset bubble detection size value.

8. The cardiopulmonary bypass system according to claim 7, wherein the at least one bubble detection sensor module further comprises a touch or pressure activated intervention button, wherein activation of the intervention button by touch or pressure causes operation of a pump of the cardiopulmonary bypass system to be temporarily modified.

9. The cardiopulmonary bypass system according to claim 3, wherein the at least one level sensor module comprises a level data field and a touch or pressure activated intervention button, wherein the intervention button is only enabled when a blood fluid level of a blood reservoir of the cardiopulmonary bypass system is at or below a predetermined low blood fluid level.

10. The cardiopulmonary bypass system according to claim 9, wherein activation of the intervention button by touch or pressure causes operation of a pump of the cardiopulmonary bypass system to be temporarily modified so as to interrupt an automatic blood fluid level correction mechanism initiated by the processor.

11. The cardiopulmonary bypass system according to claim 1, wherein the graphical user interface includes a header portion and a footer portion, wherein the central portion is disposed between the header portion and the footer portion.

12. The cardiopulmonary bypass system according to claim 1, wherein the plurality of tabbed display pages includes a patient monitor tabbed display page having a patient monitor configuration.

13. The cardiopulmonary bypass system according to claim 12, wherein the patient monitoring configuration includes a data value field that displays blood lactate level, and optionally the untabbed display page includes a timer module.

14. A cardiopulmonary bypass system comprising:
a processor;
a touchscreen comprising a customizable graphical user interface operably connected to the processor to provide user input to the processor and to display measured data pertaining to one or more parameters outputted from the processor, wherein the graphical user interface is provided with a central portion divided into four sections, wherein one section displays an untabbed display page and three sections display a plurality of tabbed display pages, wherein each section is customizable by an operator of the cardiopulmonary bypass system to include selected modules, and wherein the untabbed display page comprises a plurality of sensor modules and at least one tabbed page comprises a plurality of sensor modules that are customizable by an operator of the cardiopulmonary bypass system to include selected modules, and at least one tabbed display page comprises a plurality of cardioplegia modules, wherein the at least one tabbed display page comprising the plurality of sensor modules and the at least one tabbed display page comprising the plurality of cardioplegia modules are located in different sections of the central portion;
a plurality of sensors disposed to measure one or more parameters of an extracorporeal blood flow circuit of the cardiopulmonary bypass system, wherein the plurality of sensors are operably connected to input measured data pertaining to the one or more parameters to the processor, and wherein each sensor is linked to one of the sensor modules of either the untabbed display page or one of the tabbed display pages so that data measured by each sensor is displayable by the graphical user interface, and
a clinical parameter monitoring and simulation user interface formed by the combined simultaneous display of the patient monitor tabbed display page in a second section of the four sections, a simulator keypad tabbed display page having a simulator keypad configuration in a third section of the four sections and a simulator screen tabbed display page having a simulator screen configuration in a fourth section of the four sections, wherein when the patient monitor tabbed display page, the simulator keypad tabbed display page and the simulator screen tabbed display page are displayed simultaneously, the patient monitor tabbed display page, the simulator keypad tabbed display page and the simulator screen tabbed display page are operable together,
wherein each tabbed display page comprises a contiguous tab attached thereto, and wherein each tabbed display page is displayable in a displayed mode and in an overlaid mode so that the graphical user interface is operable to display the untabbed display page and three tabbed display pages in the displayed mode at the same time, wherein when displayed in the displayed mode all of the tabbed display page is in view, and when displayed in the overlaid mode only the contiguous tab of the tabbed display page is in view, wherein each contiguous tab is capable of transitioning to an alarm state so that when the corresponding tabbed display page is displayed in the overlaid mode and any sensor module of the corresponding tabbed display page transitions to an alarm state, the contiguous tab transitions to a viewable alarm state, and
wherein the plurality of tabbed display pages includes a patient monitor tabbed display page having a patient monitor configuration.

15. A cardiopulmonary bypass system comprising:
a processor; and
a touchscreen comprising a graphical user interface operably connected to the processor to provide user input to the processor and to display measured data pertaining to one or more parameters outputted from the processor, wherein the graphical user interface is provided with a central portion divided into four sections, wherein one section displays an untabbed display page and three sections display a plurality of tabbed display pages, wherein each tabbed display page comprises a portion from which a tab extends and each tabbed display page is displayable in a displayed mode and in an overlaid mode, and wherein the untabbed display page comprises a first plurality of sensor modules and at least one tabbed page comprises a second plurality of sensor modules and at least one tabbed page comprises a plurality of cardioplegia modules, wherein the untabbed page includes at least one pressure sensor module, at least one bubble detection sensor module, and at least one level sensor module, and wherein the at least one pressure sensor module comprises a pressure value data field and a touch or pressure activated first intervention button, wherein activation of the first intervention button by touch or pressure causes operation of a first pump of the cardiopulmonary bypass system to be temporarily modified, and wherein the at least one bubble detection sensor module further comprises a touch or pressure activated second intervention button, wherein activation of the second intervention button by touch or pressure causes operation of a second pump of the cardiopulmonary bypass system to be temporarily modified, and wherein the at least one level sensor module comprises a level data field and a touch or pressure activated third intervention button, wherein the third intervention button is only enabled when a blood fluid level of a blood reservoir of the cardiopulmonary bypass system is at or below a predetermined low blood fluid level, and activation of the third intervention button by touch or pressure causes operation of a third pump of the cardiopulmonary bypass system to be temporarily modified so as to interrupt an automatic blood fluid level correction mechanism initiated by the processor, and wherein the at least one tabbed page comprising the second plurality of sensor modules and the at least one tabbed page comprising the plurality of cardioplegia modules are located in different sections of the central portion so as to enable display of both the second plurality of sensor modules and the plurality of cardioplegia modules in a display mode at the same time, and wherein at least the untabbed display page includes a plurality of sectors and at least one section of the plurality of sectors has a sensor module settings menu button used to activate a module configuration menu interface used to configure the at least one sector to display information according to specified preferences for a current sensor module being displayed, wherein the graphical user interface comprises a clinical parameter monitoring and simulation user interface formed by a combined simultaneous display of a patient monitor tabbed display page, a simulator keypad tabbed display page having a simulator keypad configuration, and a simulator screen tabbed display page having a simulator screen configuration, wherein, when the patient monitor tabbed display page, the simulator keypad tabbed display page, and the simulator screen tabbed display page are each displayed simultaneously in the display mode, with the patient monitor tabbed display page, the simulator keypad tabbed display page, and the simulator screen tabbed display page displayed in separate sections of the central portion, these tabbed display pages are operable together as a clinical parameter monitoring and simulation interface.

16. The cardiopulmonary bypass system according to claim 15, wherein when displayed in the displayed mode all of the tabbed display page is viewable, and when displayed in the overlaid mode only the tab of the tabbed display page is viewable.

17. The cardiopulmonary bypass system according to claim 16, wherein only one tabbed display page of each section that displays the plurality of tabbed display pages is displayed in the displayed mode at a time, and the rest of the tabbed display pages are displayed in the overlaid mode.

18. The cardiopulmonary bypass system according to claim 17, wherein each tab is activatable by touch or pressure exerted on the touch screen by the user, wherein activation of the tab by touch or pressure causes the associated tabbed display page to be displayed in the displayed mode and the rest of the tabbed display pages to be displayed in the overlaid mode.

19. A cardiopulmonary bypass system comprising:
a processor; and
a touchscreen comprising a customizable graphical user interface operably connected to the processor to provide user input to the processor and to display measured data pertaining to one or more parameters outputted from the processor, wherein the graphical user interface is provided with a central portion divided into four sections, wherein one section displays an untabbed display page and three sections display a plurality of tabbed display pages, and wherein the untabbed display page comprises a plurality of sensor modules and at least one tabbed page comprises a plurality of sensor modules, wherein each tabbed display page comprises a contiguous tab attached thereto, and wherein each tabbed display page is displayable in a displayed mode and in an overlaid mode, wherein when displayed in the displayed mode all of the tabbed display page is in view, and when displayed in the overlaid mode only the contiguous tab of the tabbed display page is in view, and wherein each contiguous tab is capable of transitioning to an alarm state so that when the corresponding tabbed display page is displayed in the overlaid mode and any sensor module of the corresponding tabbed display page transitions to an alarm state, the contiguous tab transitions to a viewable alarm state, wherein the graphical user interface comprises a clinical parameter monitoring and simulation user interface formed by the combined simultaneous display of a patient monitor tabbed display page, a simulator keypad tabbed display page having a simulator keypad configuration and a simulator screen tabbed display page having a simulator screen configuration, wherein when the patient monitor tabbed display page, the simulator keypad tabbed display page and the simulator screen tabbed display page are each displayed simultaneously in the display mode, with the patient monitor tabbed display page, the simulator keypad tabbed display page and the simulator screen tabbed display page displayed in separate sections of the central portion, these tabbed display pages are operable together as the clinical parameter monitoring and simulation interface.

* * * * *